US008618509B2

(12) United States Patent
Vo-Dinh et al.

(10) Patent No.: US 8,618,509 B2
(45) Date of Patent: Dec. 31, 2013

(54) UP AND DOWN CONVERSION SYSTEMS FOR PRODUCTION OF EMITTED LIGHT FROM VARIOUS ENERGY SOURCES

(71) Applicant: Immunolight, LLC, Detroit, MI (US)

(72) Inventors: Tuan Vo-Dinh, Chapel Hill, NC (US); Jonathan P. Scaffidi, Durham, NC (US); Venkata Gopal Reddy Chada, Durham, NC (US); Benoit Lauly, Durham, NC (US); Yan Zhang, Durham, NC (US); Molly K. Gregas, Durham, NC (US); Ian Nicholas Stanton, Durham, NC (US); Joshua T. Stecher, Durham, NC (US); Michael J. Therien, Durham, NC (US); Frederic A. Bourke, Jr., Greenwich, CT (US); Zak Fathi, Raleigh, NC (US); Jennifer Ann Ayres, Raleigh, NC (US); Zhenyuan Zhang, Durham, NC (US); Joseph H. Simmons, Tucson, AR (US); Stephen John Norton, Cary, NC (US)

(73) Assignees: Immunolight, LLC, Detroit, MI (US); Duke University, Durham, NC (US)

( * ) Notice: Subject to any disclaimer, the term of this patent is extended or adjusted under 35 U.S.C. 154(b) by 0 days.

(21) Appl. No.: 13/732,882

(22) Filed: Jan. 2, 2013

(65) Prior Publication Data

US 2013/0171060 A1 Jul. 4, 2013

Related U.S. Application Data

(63) Continuation of application No. 12/725,108, filed on Mar. 16, 2010, now Pat. No. 8,389,958.

(60) Provisional application No. 61/161,328, filed on Mar. 18, 2009, provisional application No. 61/259,940, filed on Nov. 10, 2009.

(51) Int. Cl.
   *G01J 1/58* (2006.01)

(52) U.S. Cl.
   USPC ........................................ 250/459.1

(58) Field of Classification Search
   USPC ........................................ 250/459.1
   See application file for complete search history.

(56) References Cited

U.S. PATENT DOCUMENTS

| 3,688,124 | A | * | 8/1972 | Freund et al. ................. 359/330 |
| 4,608,222 | A | | 8/1986 | Brueckner |

(Continued)

FOREIGN PATENT DOCUMENTS

| WO | WO 2007/089564 A2 | 8/2007 |
| WO | WO 2008/118234 A2 | 10/2008 |

OTHER PUBLICATIONS

Feng Wang, et al., "Luminescent Nanomaterials for Biological Labelling", Nanotechnology, vol. 17, No. 1, 2006, pp. R1-R13.

Shaopeng Wang et al., "Nanoparticle Luminescence Thermometry", Journal of Physical Chemistry B, vol. 106, No. 43, Oct. 25, 2002, pp. 11203-11209.

(Continued)

*Primary Examiner* — David Porta
*Assistant Examiner* — Hugh H Maupin
(74) *Attorney, Agent, or Firm* — Oblon, Spivak, McClelland, Maier & Neustadt, L.L.P.

(57) ABSTRACT

A system for energy upconversion and/or down conversion and a system for producing a photostimulated reaction in a medium. These systems include 1) a nanoparticle configured, upon exposure to a first wavelength $\lambda_1$ of radiation, to generate a second wavelength $\lambda_2$ of radiation having a higher energy than the first wavelength $\lambda_1$ and 2) a metallic structure disposed in relation to the nanoparticle. A physical characteristic of the metallic structure is set to a value where a surface plasmon resonance in the metallic structure resonates at a frequency which provides a spectral overlap with either the first wavelength $\lambda_1$ or the second wavelength $\lambda_2$, or with both $\lambda_1$ and $\lambda_2$. The system for producing a photostimulated reaction in a medium includes a receptor disposed in the medium in proximity to the nanoparticle which, upon activation by the second wavelength $\lambda_2$, generates the photostimulated reactio

76 Claims, 44 Drawing Sheets

(56) References Cited

U.S. PATENT DOCUMENTS

| | | | |
|---|---|---|---|
| 5,773,609 | A | 6/1998 | Robinson et al. |
| 6,924,921 | B2 | 8/2005 | Lewis, III et al. |
| 7,112,306 | B2 | 9/2006 | Obee et al. |
| 7,604,523 | B1 | 10/2009 | Wedding et al. |
| 2002/0119485 | A1 | 8/2002 | Morgan |
| 2004/0014060 | A1 | 1/2004 | Hoheisel et al. |
| 2004/0181344 | A1 | 9/2004 | Stephanopoulos et al. |
| 2004/0196538 | A1* | 10/2004 | Burgener et al. .......... 359/341.5 |
| 2005/0186565 | A1 | 8/2005 | Malak |
| 2007/0059705 | A1 | 3/2007 | Lu et al. |
| 2009/0116753 | A1* | 5/2009 | Midgley et al. ............... 382/219 |
| 2010/0224821 | A1 | 9/2010 | Mandelbaum et al. |

OTHER PUBLICATIONS

International Search Report issued Oct. 20, 2010, in PCT/US10/27373 filed Mar. 16, 2010.

T.V. Teperik, et al., "Strong Terahertz Absorption Bands in a Scaled Plasmonic Crystal", Applied Physics Letters, 90, 251910, Jun. 19, 2007, pp. 90-92.

Serena Eley et al., "A Study of Optical Properties of ZBLAN Microspheres Produced in Microgravity", NASA reduced Gravity Student Flight Opportunities Program 2002 Competition, 2002, pp. 1-18.

International Search Report and Written Opinion issued Mar. 28, 2011, in PCT/US2010/056178 filed Nov. 10, 2010.

\* cited by examiner

PLASMONICS PHOTO-ACTIVE PROBES

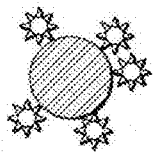

PA MOLECULES BOUND TO
METAL NANOPARTICLE

*Fig. 4A-A*

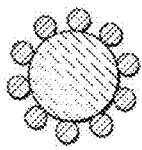

PA-CONTAINING NANO-
PARTICLE COVERED WITH
METAL NANOPARTICLES

*Fig. 4A-B*

 PHOTO-ACTIVE (PA)
MOLECULE
(PHOTOSENSITIZER)

METAL (e.g. Au, Ag)

MATERIAL
CONTAINING PA

 PROTECTIVE
COATING

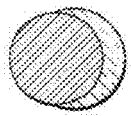

METAL NANOPARTICLE
COVERED WITH PA NANOCAP

*Fig. 4A-C*

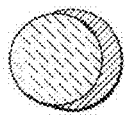

PA-CONTAINING NANO-
PARTICLE COVERED WITH
METAL NANOCAP

*Fig. 4A-D*

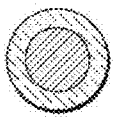

METAL NANOPARTICLE
COVERED WITH PA NANOSHELL

*Fig. 4A-E*

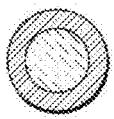

PA-CONTAINING NANO-
PARTICLE COVERED WITH
METAL NANOSHELL

*Fig. 4A-F*

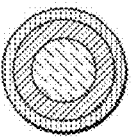

PA-CONTAINING NANO-
PARTICLE COVERED WITH
METAL NANOSHELL WITH
PROTECTIVE COATING LAYER

*Fig. 4A-G*

Y₂O₃ = Y₂O₃, Y₂O₃:Ln; sub 5-nm.
Au(Ag,Pt)shell = monolayer to $x$ nm

PLASMONICS PHOTO-ACTIVE PROBES

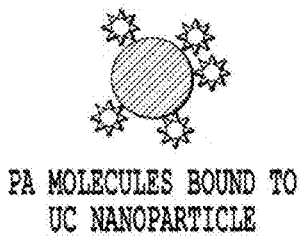
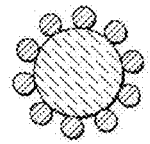

☆ PHOTO-ACTIVE (PA) MOLECULE (PHOTOSENSITIZER)

▨ METAL (e.g. Au, Ag)

▨ UPCONVERTING MATERIAL (UCm)

▨ PROTECTIVE COATING

PA MOLECULES BOUND TO UC NANOPARTICLE

*Fig. 6A-A*

UCm-CONTAINING NANO-PARTICLE COVERED WITH METAL NANOPARTICLES

*Fig. 6A-B*

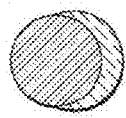
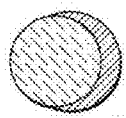

METAL NANOPARTICLE COVERED WITH UCm NANOCAP

*Fig. 6A-C*

UCm-CONTAINING NANO-PARTICLE COVERED WITH METAL NANOCAP

*Fig. 6A-D*

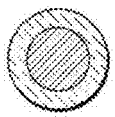
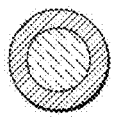
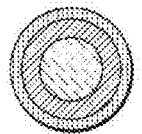

METAL NANOPARTICLE COVERED WITH UCm NANOSHELL

*Fig. 6A-E*

UCm-CONTAINING NANO-PARTICLE COVERED WITH METAL NANOSHELL

*Fig. 6A-F*

UCm-CONTAINING NANO-PARTICLE COVERED WITH METAL NANOSHELL WITH PROTECTIVE COATING LAYER

*Fig. 6A-G*

PLASMONICS PHOTO-ACTIVE PROBES WITH
ENERGY UPCONVERTING MATERIALS

☆ PHOTO-ACTIVE (PA) MOLECULE (PHOTOSENSITIZER)

▨ METAL (e.g. Au,Ag)

▧ UPCONVERTING MATERIAL (UCm)

▦ PROTECTIVE COATING

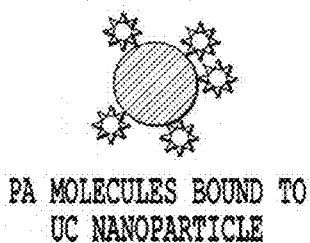

PA MOLECULES BOUND TO UC NANOPARTICLE

*Fig.6B-A*

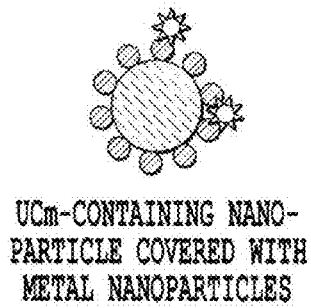

UCm-CONTAINING NANO-PARTICLE COVERED WITH METAL NANOPARTICLES

*Fig.6B-B*

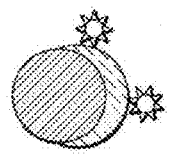

METAL NANOPARTICLE COVERED WITH UCm NANOCAP

*Fig.6B-C*

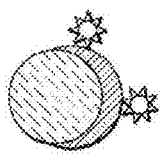

UCm-CONTAINING NANO-PARTICLE COVERED WITH METAL NANOCAP

*Fig.6B-D*

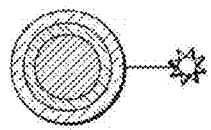

METAL NANOPARTICLE COVERED WITH DIELECTRIC LAYER AND UCm NANOSHELL

*Fig.6B-E*

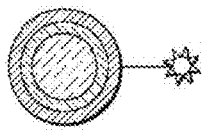

METAL NANOPARTICLE COVERED WITH DIELECTRIC LAYER AND METAL NANOSHELL

*Fig.6B-F*

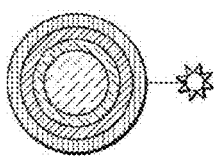

METAL NANOPARTICLE COVERED WITH DIELECTRIC LAYER AND METAL NANOSHELL WITH PROTECTIVE COATING LAYER

*Fig.6B-G*

PLASMONICS-ACTIVE METAL STRUCTURES

METAL NANOPARTICLE

*Fig. 6C-A*

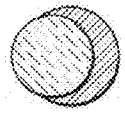

DIELECTRIC NANOPARTICLE CORE COVERED WITH METAL NANOCAP

*Fig. 6C-B*

▨ METAL 1 (e.g. Au, Ag)
▨ METAL 2 (e.g. Au, Ag)
▨ UPCONVERSION MATERIAL
▨ PROTECTIVE COATING

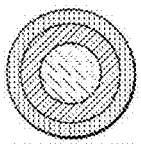

SPHERICAL METAL NANOSHELL COVERING UCm SPHEROID CORE

*Fig. 6C-C*

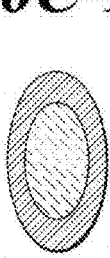

OBLATE METAL NANO-SHELL COVERING UCm SPHEROID CORE

*Fig. 6C-D*

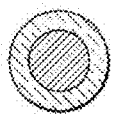

METAL NANOPARTICLE CORE COVERED WITH UCm NANOSHELL

*Fig. 6C-E*

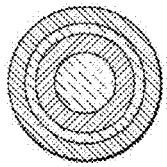

METAL NANOSHELL WITH UCm CORE AND PROTECTIVE COATING LAYER

*Fig. 6C-F*

MULTI-LAYER METAL NANOSHELLS COVERING UCm CORE AND NANOSHELL

*Fig. 6C-G*

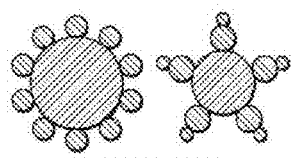

MULTI-NANO-PARTICLE STRUCTURES

*Fig. 6C-H*

METAL NANOCUBE AND NANO-TRIANGLE/NANO-PRISM

*Fig. 6C-I*

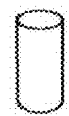

METAL CYLINDER

*Fig. 6C-J*

PLASMONICS PHOTO-ACTIVE PROBES
WITH ENERGY UPCONVERTING MATERIALS

☆ PHOTO-ACTIVE (PA) MOLECULE (PHOTOSENSITIZER)

▨ METAL (e.g. Au, Ag)

▨ UPCONVERTING MATERIAL (UCm)

▨ PROTECTIVE COATING

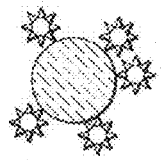

PA MOLECULES BOUND TO UC NANOPARTICLE

*Fig. 6D-A*

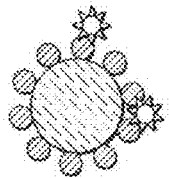

UCm-CONTAINING NANO-PARTICLE COVERED WITH METAL NANOPARTICLES

*Fig. 6D-B*

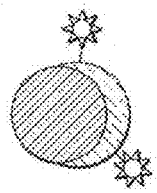

METAL NANOPARTICLE COVERED WITH UCm NANOCAP

*Fig. 6D-C*

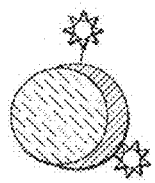

UCm-CONTAINING NANOPARTICLE COVERED WITH METAL NANOCAP

*Fig. 6D-D*

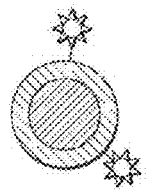

METAL NANOPARTICLE COVERED WITH UCm NANOSHELL

*Fig. 6D-E*

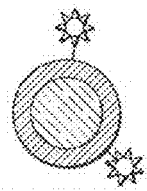

UCm-CONTAINING NANOPARTICLE COVERED WITH METAL NANOSHELL

*Fig. 6D-F*

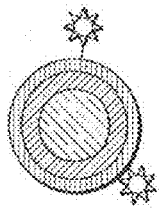

UCm-CONTAINING NANOPARTICLE COVERED WITH METAL NANOSHELL WITH PROTECTIVE COATING LAYER

PLASMONICS PHOTO-ACTIVE UCm PROBES WITH BIORECEPTORS

- ☆ PHOTO-ACTIVE (PA) MOLECULE (PHOTOSENSITIZER)
- ⊂ BIORECEPTOR (Ab, DNA, etc.)
- ▨ METAL (e.g. Au, Ag)
- ▨ UPCONVERTING MATERIAL (UCm)
- ▨ PROTECTIVE COATING

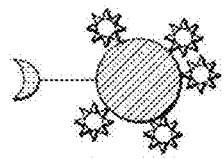

PA MOLECULES BOUND TO METAL NANOPARTICLE

*Fig. 8A-A*

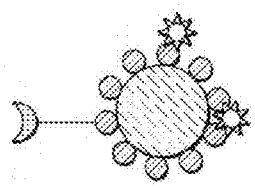

A-LINKED UCM NANO-PARTICLE COVERED WITH METAL NANOPARTICLES

*Fig. 8A-B*

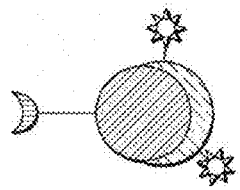

METAL NANOPARTICLE COVERED WITH UCm NANOCAP WITH LINKED PA

*Fig. 8A-C*

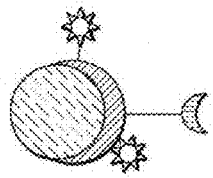

UCm NANOPARTICLE COVERED WITH METAL NANOCAP AND LINKED PA

*Fig. 8A-D*

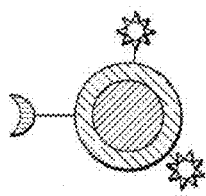

METAL NANOPARTICLE COVERED WITH UCm NANOSHELL WITH PA

*Fig. 8A-E*

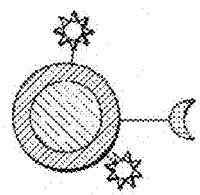

UCm NANOPARTICLE COVERED WITH METAL NANOSHELL

*Fig. 8A-F*

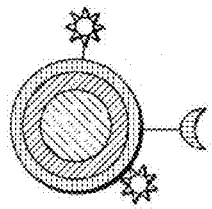

UCm NANOPARTICLE COVERED WITH METAL NANOSHELL WITH PROTECTIVE COATING LAYER

*Fig. 8A-G*

PLASMONICS PHOTO-ACTIVE PROBES
UCm-PA SYSTEMS WITH BIORECEPTORS

☆ PHOTO-ACTIVE (PA) MOLECULE (PHOTOSENSITIZER)

⊂ OPTIONAL BIORECEPTOR (Ab,DNA,etc.)

▨ PLASMONICS-ACTIVE METAL (e.g. Au,Ag)

▧ ENERGY UPCONVERTING MATERIAL (UCm)

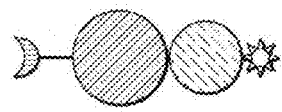

PA MOLECULES BOUND TO UCm AND TO PLASMONIC METAL NANOPARTICLE

*Fig. 8B-A*

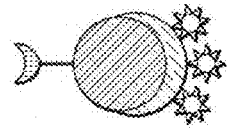

PLASMONIC METAL NANO-PARTICLE WITH UCm NANOCAP COVERED WITH PA MOLECULES

*Fig. 8B-B*

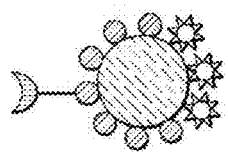

PA-COVERED UCm NANOPARTICLE WITH PLASMONIC METAL NANOPARTICLES

*Fig. 8B-C*

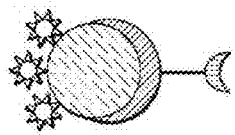

UCm-CONTAINING NANOPARTICLE COVERED WITH PA MOLECULES AND PLASMONIC METAL NANOCAP

*Fig. 8B-D*

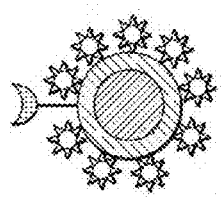

PLASMONIC METAL NANOPARTICLE CORE WITH UCm NANOSHELL COVERED WITH PA MOLECULE

*Fig. 8B-E*

Inside the cell, photon radiation releases PA which can go to target area (e.g., nucleus)

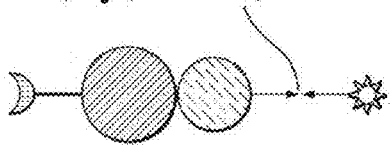

PA MOLECULE BOUND TO UCm (ATTACHED TO PLASMONICS METAL NANOPARTICLE) NANOPARTICLE BY DETACHABLE BIOCHEMICAL BOND

*Fig. 8B-F*

UP AND DOWN CONVERSION SYSTEMS FOR PRODUCTION OF EMITTED LIGHT FROM VARIOUS ENERGY SOURCES

CROSS REFERENCE TO RELATED APPLICATIONS

This application is a continuation of U.S. Ser. No. 12/725,108 filed Mar. 16, 2010. This application is related to and claims priority under 35 U.S.C. 119 to U.S. provisional patent application 61/161,328, filed Mar. 18, 2009 and to U.S. provisional patent application 61/259,940, filed Nov. 10, 2009, the entire disclosures of which are hereby incorporated by reference.

This application is related to Provisional Application Ser. Nos. 60/954,263, filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. Nos. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and 12/059,484, filed Mar. 31, 2008; U.S. patent application Ser. No. 12/389,946, filed Feb. 20, 2009; U.S. patent application Ser. No. 12/417,779, filed Apr. 3, 2009, the entire disclosures of which are hereby incorporated by reference.

BACKGROUND OF THE INVENTION

1. Field of Invention

The invention relates to methods and systems for producing light from lower and higher energy activation sources. The invention also relates to systems and methods for broad band up conversion from the microwave and RF regime to electromagnetic radiation of higher photonic energy in the UV, VIS, and IR regime.

2. Discussion of the Background

Presently, light (i.e., electromagnetic radiation from the radio frequency through the visible to the X-ray wavelength range) is used in a number of industrial, communication, electronic, and pharmaceutical processes. Light in the infrared and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules). Both processes play a role in the glowing filament of incandescent lamps, whereas the latter process (electrons within atoms) occurs in fluorescent lamps.

The duality nature of light (or more generally electromagnetic radiation) is such that light is both a wave (characterized by a wavelength and amplitude) and a discrete parcel of energy or photon (characterized by its frequency times the Planck constant (denoted h). The higher the frequency the higher the quantized energy carried by the radiation. All energy above the visible is considered in many circumstances to be ionizing radiation as its photons carry sufficient energy to ionize matter.

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in $W/m^2$ ($lm/m^2$ or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

With the development of infrared radiation sources, infra-red radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many, if not all, of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence and fluorescence, which is the ability of certain solids to emit light when driven or charged by an external energy source. Many well-known phosphors and fluorescers are triggered by high-energy electrons or photons and emit photons of lower energy. There is a type of phosphor which can store energy for long periods of time in certain energy states. Relaxation from these energy states at a later time can be stimulated by less energetic photons. Relaxation from these energy states results in photon emission. The effect of this phenomenon is that energy is stored in the form of trapped electron-hole pairs for later use. Materials which exhibit this phenomenon will be referred to as electron trapping, or electron trapping phosphors, and materials in which emission of light is activated by infrared lumination are called infrared phosphors.

It has been recognized recently that certain infrared phosphors can actually operate at high speeds and are capable of converting pulsed infrared light to the visible range (violet through red). This "upconversion" occurs at the expense of the original charging illuminating light and can actually exhibit optical gain. It has been observed that phosphorescence can continue for as long as several days before a new short recharge are required.

Up conversion and down conversion of electromagnetic radiations are very relevant to various industrials fields. Photo-activated chemical reactions find broad use in the industry from catalyzing reactions to Bio-modulation of therapeutic agents. However, UV radiation suffers from a lack of depth of penetration in matter especially biological media, polymers and most solids). For this reason, UV based photo-initiation is limited by direct line of site which prevents volumetric applications.

UV has been limited to reactions taking place on the outer surfaces of materials may they be solids or liquids; organic or inorganic; biological organs, living tissues and composites thereof, structural composites, materials residing inside chemical tanks/reactors for food processing or hydrocarbon chains fractionation (to name a few examples).

SUMMARY OF THE INVENTION

In one embodiment, there is provided a system for energy upconversion. The system includes a nanoparticle configured, upon exposure to a first wavelength $\lambda_1$ of radiation, to generate a second wavelength $\lambda_2$ of radiation having a higher energy than the first wavelength $\lambda_1$. The system includes a metallic structure disposed in relation to the nanoparticle. A physical characteristic of the metallic structure is set to a value where a surface plasmon resonance in the metallic structure resonates at a frequency which provides spectral overlap with either the first wavelength $\lambda_1$ or the second wavelength $\lambda_2$.

In another embodiment, there is provided a system for producing a photostimulated reaction in a medium. The system includes a nanoparticle configured, upon exposure to a first wavelength $\lambda_1$ of radiation, to generate a second wavelength $\lambda_2$ of radiation having a higher energy than the first wavelength $\lambda_1$. The system includes a metallic structure disposed in relation to the nanoparticle and includes a receptor disposed in the medium in proximity to the nanoparticle. The receptor upon activation by the second wavelength $\lambda_2$ generates the photostimulated reaction. A physical characteristic of the metallic structure is set to a value where a surface plasmon resonance in the metallic structure resonates at a frequency which provides spectral overlap with either the first wavelength $\lambda_1$ or the second wavelength $\lambda_2$.

In yet another embodiment, there is provided a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structure to enhance upconversion of light from a first wavelength $\lambda_1$ to a second wavelength $\lambda_2$.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 4A-1 is an UV-visible absorption spectra of cubic $Y_2O_3$ and gold-coated $Y_2O_3$ dispersed using 10 mM tri-arginine;

FIG. 5A-1 is a schematic depicting an $Y_2O_3$ dielectric particle coated with a sub 5 nm metallic coating;

FIG. 5A-2 is a micrograph showing ~15 nm cubic $Y_2O_3$ dielectric particles generated through the combustion method;

FIG. 6A is a schematic illustration of other various upconverter structures of the invention;

FIG. 6B is another schematic illustration of other various upconverter structures of the invention;

FIG. 6C is a schematic illustration of plasmonics-active upconverter structures of the invention;

FIG. 6D is a schematic illustration of photo-active molecules linked to plasmonics-active upconverter structures of the invention;

FIG. 8A is a schematic illustration of other various upconverter structures of the invention where the dielectric core has appended thereon or attached by linkages a bioreceptor molecule;

FIG. 8B is a schematic illustration of still other various upconverter structures of the invention where the dielectric core has appended thereon or attached by linkages a bioreceptor molecule;

DETAILED DESCRIPTION OF THE INVENTION

Figure 1:
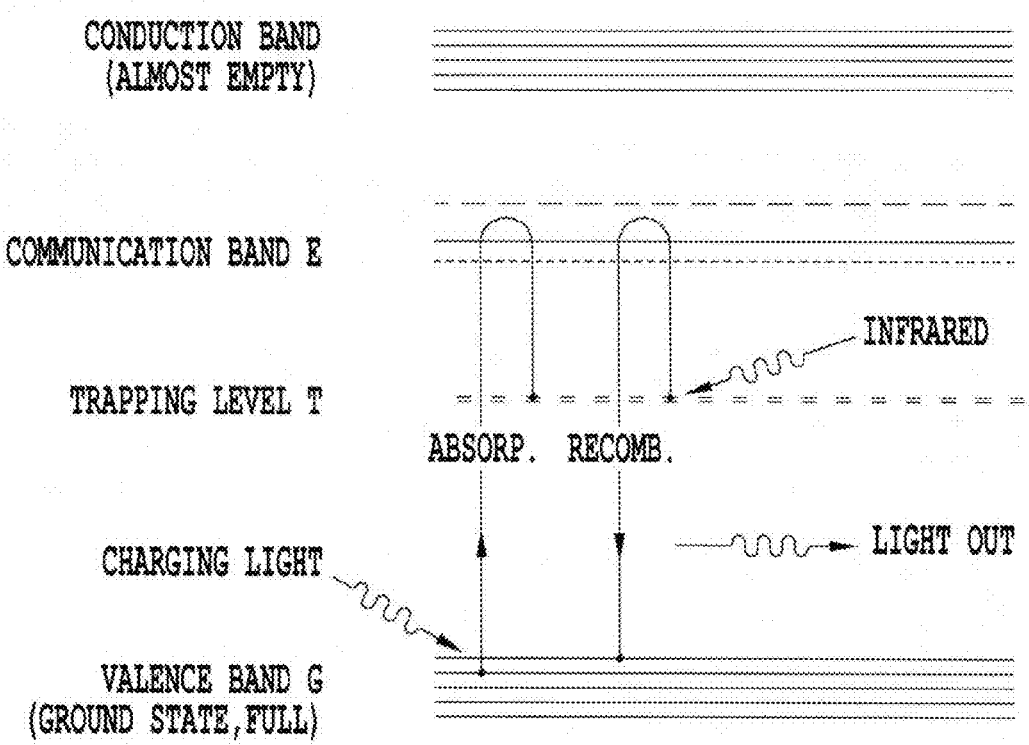
FIG. 1 is an energy diagram of an infrared phosphor system.

The invention is directed to methods and systems for producing electromagnetic radiation having desirable frequency windows (at least one frequency within a desirable frequency range) from other electromagnetic radiation having lower or higher frequency ranges using up converting transitional media or down converting transitional media as the case may apply. In various embodiments of the invention, the produced electromagnetic radiation is then be used to activate an agent in a medium where the up converting transitional media or down converting transitional media are disposed. In various embodiments, the applied energy is considered to be up converted, as the photon energy carried by radiation 1 has an energy level equal to $hv_1$ (the product of Planck constant and frequency 1) is converted to a higher energy $hv_2$, where $hv_1$ is less than $hv_2$. In various embodiments, the applied energy is considered to be down converted, as energy at $hv_1$, is converted to a lower energy $hv_2$, where $hv_1$ is greater than $hv_2$.

In various embodiments of the invention, there are provided systems and methods for broad band up conversion from the microwave and RF regime to electromagnetic radiation of higher photonic energy in the UV, VIS, and IR regime. The invention can encompasses a variety of applications where the up and down conversions are conducted inside biological media (or) inside human and animal bodies; in chemical reactors and/or in semiconductors and solar cells to name but a few.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of having a size less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

U.S. Pat. No. 4,705,952 (the contents of which are hereby incorporated herein by reference) describes an infrared-triggered phosphor that stored energy in the form of visible light of a first wavelength and released energy in the form of visible light of a second wavelength when triggered by infrared light. In some cases, U.S. Pat. No. 4,705,952 describes that "the upconversion continues for as long as several days before a new short recharge is required." The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention.

The energy relations present in the upconverter in U.S. Pat. No. 4,705,952 are shown in the energy diagram of FIG. 1, where energy states E and T are introduced by two selected impurities. Excitation of these states by absorption of light having a minimum energy of E minus G will cause electrons to be raised to the band at energy state E. When charging illumination ceases, many of the excited electrons will fall to energy state T and remain trapped there. The trapping phenomenon is illustrated at the left of FIG. 1. Later exposure to triggering illumination of infrared light can supply E minus T energies, permitting the infrared-triggered phosphor in excited state T to transition to level E, as shown at the right of FIG. 1. A photon is emitted during this transition process. The resulting light emission is characterized by a wavelength associated with E minus G.

If the depth of the trap is several times higher than the thermal energy, more than 99% of the electrons are in the electron-hole trap. If the depth of the traps is about 1 eV, then in the dark, most of the traps are filled, band E is almost empty and electron hole recombination is negligible. In some cases, U.S. Pat. No. 4,705,952 describes that "the storage times become extremely long, on the order of years." The material is thus adapted to receive infrared photons and to emit higher energy photons in a close to 1:1 relation. With storage times this long, these infrared-triggered phosphors can be used in various embodiments of the invention as a viable mechanism for both medical and non-medical applications where commercial IR lasers are used to activate phosphorescence in a medium, thereby internally in a medium or in a patient generating visible or ultraviolet light.

Considerable effort has gone into the synthesis of luminescent nanoparticles, and numerous investigations of the optical properties have been performed. The synthesis of oxide nanoparticles such as those that are based on the lanthanides have been achieved by a number of processes including solid-gel (sol-gel) techniques, gas phase condensation or colloidal chemical methods. While efforts to make concentrated colloidal solutions of highly uniform size luminescent nanoparticles have met with some technical difficulties, synthesis of useful amounts of some 5 nanometer sized lanthanide doped oxides have been achieved as shown in a paper by Bazzi et al entitled *Synthesis and luminescent properties of sub 5-nm lanthanide oxide particles*, in the Journal of Luminescence 102 (2003) pages 445-450, the entire contents of which are incorporated herein by reference. Materials such as these and the other materials discussed below are useful materials for upconversion although the prior art to date has not concentrated on particular application of these materials for materials, chemical, medical, pharmaceutical, or industrial processing. Indeed, the work by Bazzi et al concentrated on understanding the properties on lanthanide oxide nanonparticles with an emphasis on the microstructural properties and optical emission properties (i.e. concentrated on the fluorescence and down conversion properties of these materials). Nevertheless, the materials described by Bazzi et al are useful in various embodiments of the invention.

The present inventors have realized that such upconversion materials can be used in various materials, chemical, medical, pharmaceutical, or industrial processing. In one example of others to be described below, a nanoparticle of a lanthanide doped oxide can be excited with near infrared laser light such as 980 nm and 808 nm to produce both ultraviolet, visible, and near infrared light depending on the dopant trivalent rare earth ion(s) chosen, their concentration, and the host lattice. The ultraviolet, visible, and/or near infrared light can then be used to drive photoactivatable reactions in the host medium containing the lanthanide doped oxide.

Other work reported by Suyver et al in *Upconversion spectroscopy and properties of NaYF$_4$ doped with Er$^{3+}$, Tm$^{3+}$ and or Yb$^{3+}$*, in Journal of Luminescence 117 (2006) pages 1-12, the entire contents of which are incorporated herein by reference, recognizes in the NaYF$_4$ material system upconversion properties. Yet, there is no discussion as to the quality or quantity of upconverted light to even suggest that the amount produced could be useful for various materials, chemical, medical, pharmaceutical, or industrial processing. The materials described by Suyver et al are useful in various embodiments of the invention.

Reference will now be made in detail to a number of embodiments of the invention, examples of which are illustrated in the accompanying drawings, in which like reference characters refer to corresponding elements.

Figure 2:
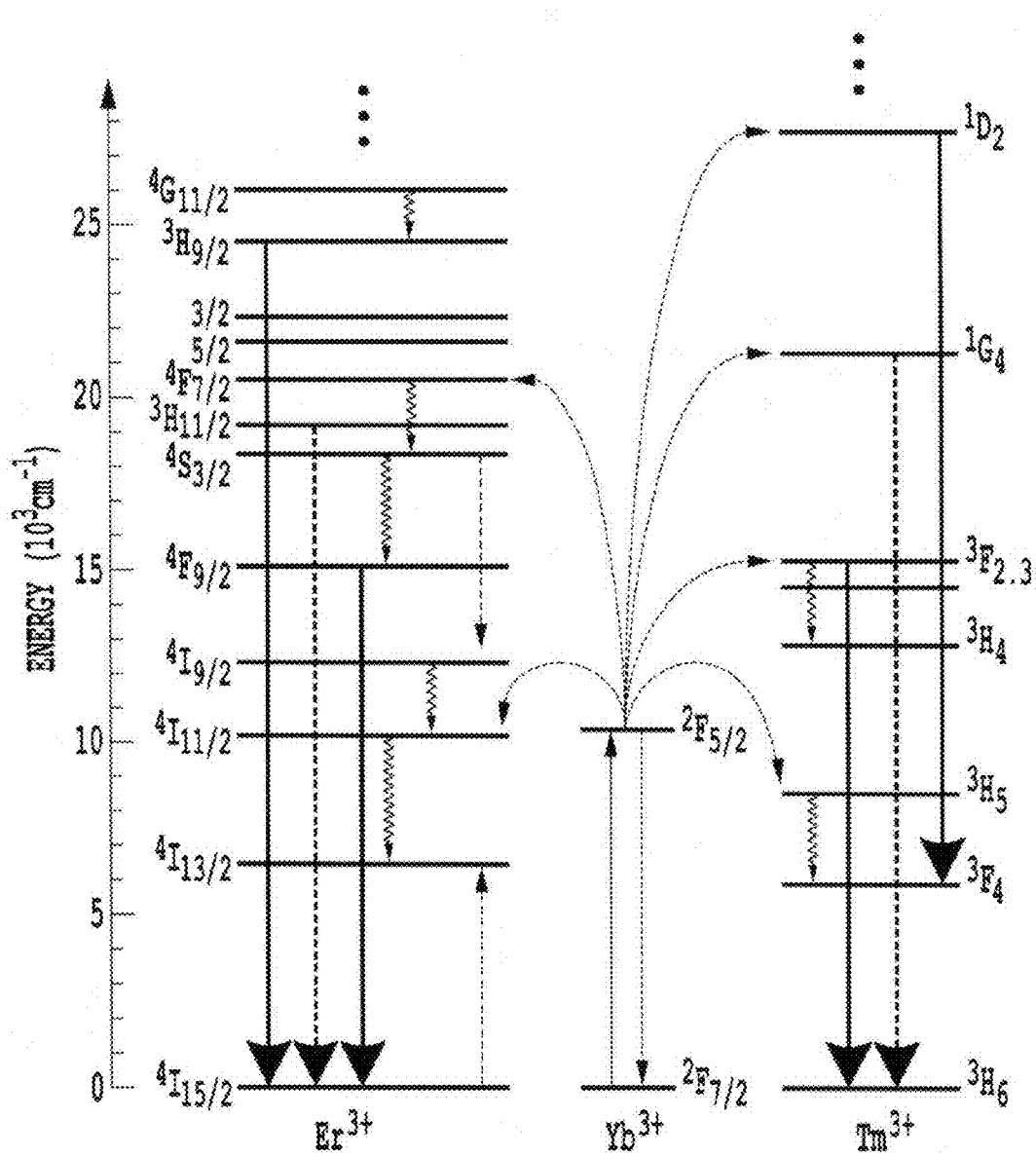
FIG. 2 is a schematic energy level diagram showing upconversion excitation and visible emissions schemes for $Er^{3+}$, $Tm^{3+}$ and or $Yb^{3+}$ ions.

FIG. 2 is a schematic reproduced from Suyver et al showing a schematic energy level diagram of upconversion excitation and visible emissions schemes for Er$^{3+}$, Tm$^{3+}$ and or Yb$^{3+}$ ions. Full, dotted, dashed, and curly arrows indicate respectively radiative, non-radiative energy transfer, cross relaxation and other relaxation processes.

The lanthanide doped oxides differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the NaYF$_4$ such that the Yb$^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the Yb$^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

Figure 3:
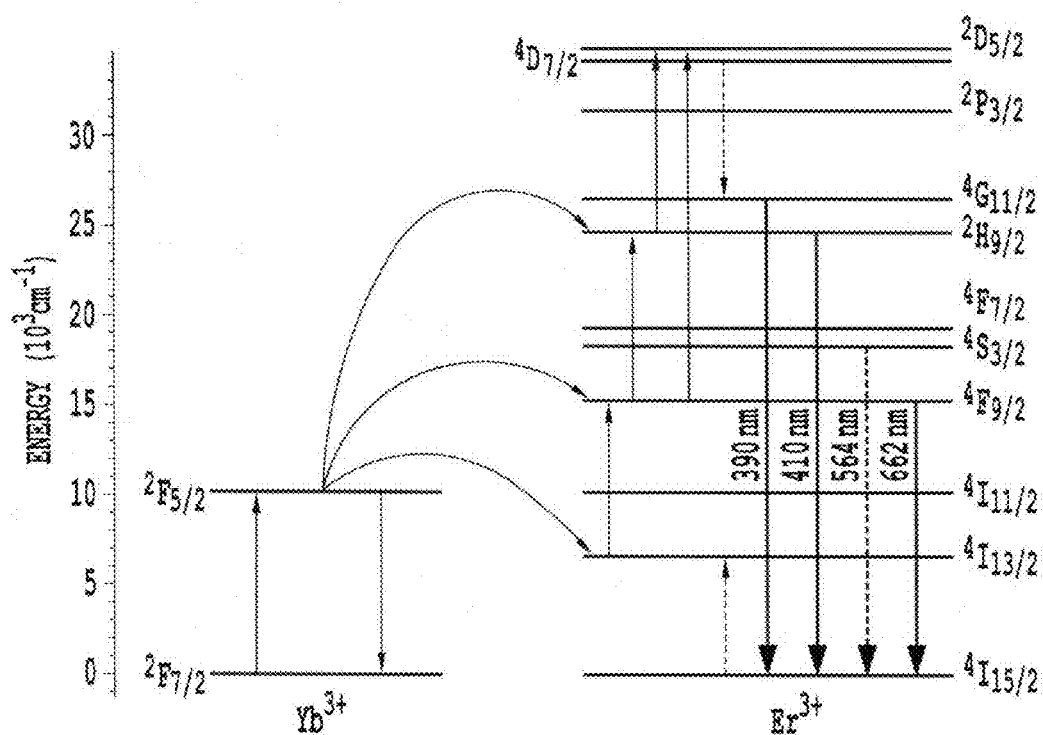
FIG. 3 is an energy diagram showing energy states for a four-photon upconversion process in $Y_2O_3$ nanocrystals.

Chen et al have described a four-photon upconversion in *Four-photon upconversion induced by infrared diode laser excitation in rare-earth-ion-doped Y$_2$O$_3$ nanocrystals*, Chemical Physics Letters, 448 (2007) pp. 127-131 In that paper, emissions at 390 nm and at 409 nm were associated with a four-photon upconversion process in the Y$_2$O$_3$ nanocrystals. FIG. 3 reproduced below from Chen et al shows a ladder of states by which an infrared light source can progressively pump until the $^4D_{7/2}$ state is reached. From this upper state, transitions downward in energy occur until the $^4G_{1/2}$ state is reached, where a transition downward in energy emits a 390 nm photon. The materials described by Chen et al are useful in various embodiments of the invention.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as Er$^{3+}$ doped BaTiO$_3$ nanoparticles and Yb$^{3+}$ doped CsMnCl$_3$) are suitable in various embodiments of the invention.

Further, materials specified for up conversion in the invention include CdTe, CdSe, ZnO, CdS, Y$_2$O$_3$, MgS, CaS, SrS and BaS. Such up conversion materials may be any semiconductor and more specifically, but not by way of limitation, sulfide, telluride, selenide, and oxide semiconductors and their nanoparticles, such as Zn$_{1-x}$Mn$_x$S$_y$, Zn$_{1-x}$Mn$_x$Se$_y$, Zn$_{1-x}$Mn$_x$Te$_y$, Cd$_{1-x}$MnS$_y$, Cd$_{1-x}$Mn$_x$Se$_y$, Cd$_{1-x}$Mn$_x$Te$_y$, Pb$_{1-x}$Mn$_x$S$_y$, Pb$_{1-x}$Mn$_x$Se$_y$, Pb$_{1-x}$Mn$_x$Te$_y$, Mg$_{1-x}$MnS$_y$, Ca$_{1-x}$Mn$_x$S$_y$, Ba$_{1-x}$Mn$_x$S$_y$ and Sr$_{1-x}$, etc. (wherein, 0<x≤1, and 0<y≤1). Complex compounds of the above-described semiconductors are also contemplated for use in the invention—e.g. (M$_{1-z}$ $N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; 0<x≤1, 0<y≤1, 0<z≤1). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn, Yb; MgS; Mn, Yb; CaS; Mn, Yb etc., and their complex compounds: $(M_{1-z}N_z)_{1-x}(Mn_qR_{1-q})_xA_{1-y}B_y$, (M=Zn, Cd, Pb, Ca, Ba, Sr, Mg; N=Zn, Cd, Pb, Ca, Ba, Sr, Mg; A=S, Se, Te, O; B=S, ... 0<z≤1, o<q≤1).

Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er3^+$; $ZnS:Mn^{2+}$; ZnS:Mn, $Er^{3+}$ are known in the art to function for both down-conversion luminescence and upconversion luminescence.

Because upconversion stimulates or produces emission at shorter wavelengths, there are applications directed to medicine where the longer wavelength light is more capable than a shorter wavelength light of penetrating deep into biological tissue. Accordingly, with upconverter materials pre-positioned inside for example a biological tissue or an aqueous solution, the longer wavelength light (such as from a commercial IR laser) can be used in one embodiment to image deep skin tissue (with the upconverter materials emitting visible or NIR light for detection), and/or the longer wavelength light in one embodiment can be used to excite the upconverters in the biological tissue and thereafter produce shorter wavelength light (e.g., ultraviolet light) to drive photochemical or pharmaceutical reactions in the body. Details of these particular applications will be discussed in more detail later.

Figures 1, 4A:
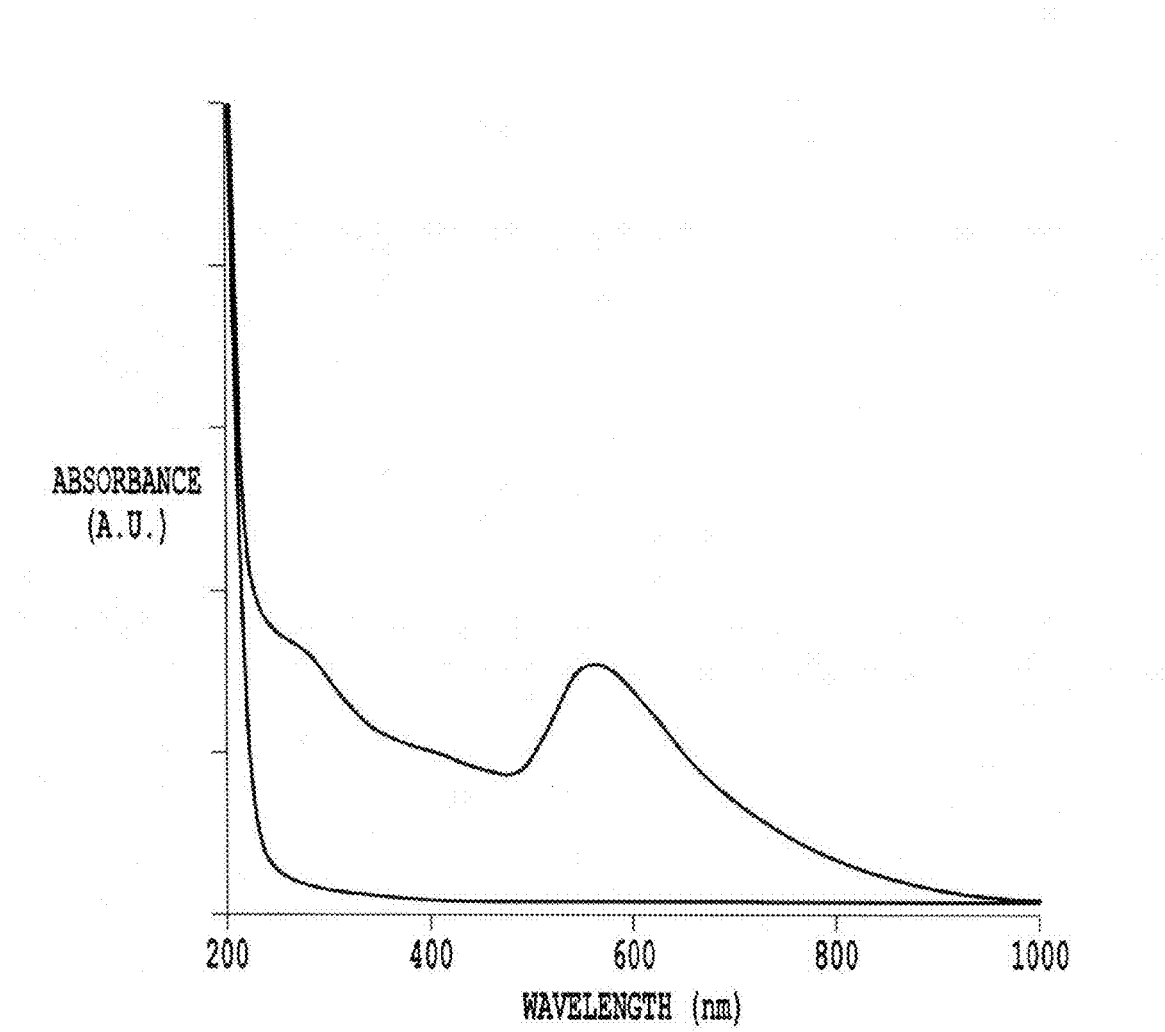
FIG. 4A is a schematic illustration of various upconverter structures of the invention.

FIG. 4A is a schematic of a depiction of an upconverter material (i.e., a photoactive material) according to one embodiment of the invention. FIG. 4A shows a number of structural configurations for placement of a dielectric core upconverter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 4A, when a wavelength $\lambda_1$ interacts with a dielectric material core, three separate processes are well understood for the upconversion process involving trivalent rare earth ions. These three processes are:

1) excited state absorption whereby two photons are absorbed sequentially by the same ion to excite and populate one or more states;
2) energy transfer upconversion which is a transfer of excitation from one ion to another already in an excited state; and
3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by the NIR source to generate the resultant emission $\lambda_2$. While many of these materials have been studied in the past in the bulk state, prior to the invention, the targeted use of these materials in the noncrystalline and nanosize range for various materials, chemical, medical, pharmaceutical, or industrial processing have not been exploited, especially at the size of dielectric cores and with the application of metallic shells.

Hence, the invention in one embodiment provides a nanoscale upconversion system for producing a photostimulated reaction in a medium. The system includes a nanoparticle configured, upon exposure to a first wavelength $\lambda_1$ of radiation, to generate a second wavelength $\lambda_2$ of radiation having a higher energy than the first wavelength $\lambda_1$. The system includes a metallic structure disposed in relation to the nanoparticle (e.g. a metallic shell covering a fraction of the nanoparticle) and includes a receptor disposed in the medium in proximity to the nanoparticle. The receptor upon activation by the second wavelength $\lambda_2$ generates directly or indirectly the photostimulated reaction. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and oboid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and oboid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multilayer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

Figure 4B:
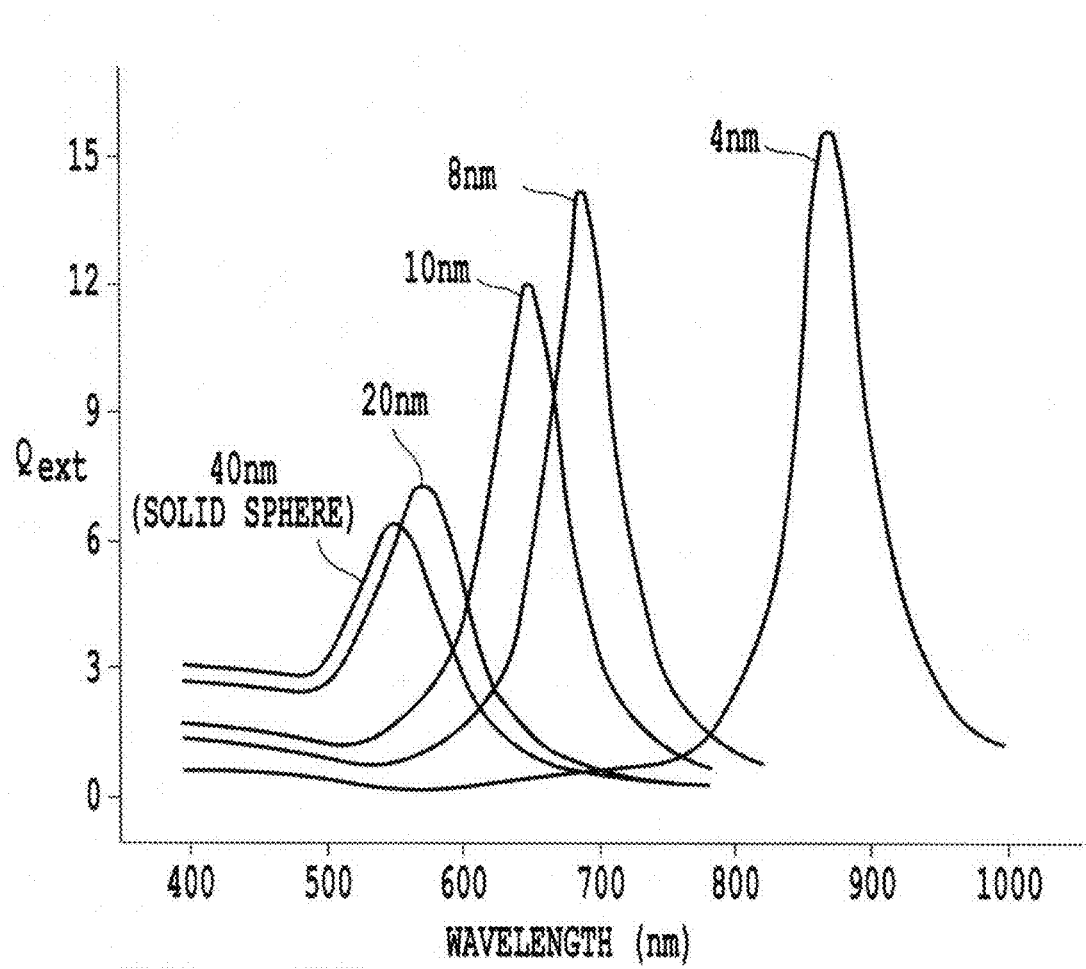
FIG. 4B is a schematic illustration of plasmon resonance as a function of shell thickness.

Such a plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanolett*. 2007, 7(9), 2854 the entire contents of which are incorporated herein by reference.) FIG. 4B is reproduced from Jain et al and illustrates the capability in the invention to "tune" the metal shell to have a spectral overlap with the excitation and/or emission radiation wavelengths. This capability of matching or tuning of the frequencies provides an enhancement of the absorption which would not be present with a dielectric core alone.

In one embodiment of the invention, the metallic structures can be an alloy such as for example a Au:Ag alloy. The alloy content can be set to adjust the frequency of the surface plasmon resonance. For instance, the alloy content may be one factor providing a surface plasmon resonance at 365 nm. In one embodiment, specifically a silver concentration of 65 to 75%, and more specifically a silver concentration of 67% is used for a 365 nm surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a surface plasmon resonance at 365 nm and specifically having a zinc sulfide concentration of 65 to 75%, and more specifically a zinc sulfide concentration of 67%. In one embodiment of the invention, the zinc sulfide and cadmium sulfide nanoparticle alloy can have an alloy content is set to provide a surface plasmon resonance at 365 nm and specifically having a zinc sulfide concentration of 65 to 75%, and more specifically a zinc sulfide concentration of 67%.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the nanoparticle can be a dielectric or semiconductor configured to generate the wavelength $\lambda_2$. In one embodiment of the invention, the nanoparticle can include multiple dielectrics or semiconductors respectively configured to emit at different wavelengths for $\lambda_2$. In one embodiment of the invention, multiple nanoparticles having different dielectrics or semiconductors can be included in a mixture of the nanoparticles dispersed in the medium.

In one embodiment of the invention, a quantum dot mixture can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted.

Specifically, in one embodiment of the invention, a quantum dot mixture (QDM) coating can be deposited using CVD and or sol-gel techniques using standard precipitation techniques. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

In one embodiment of the invention, the thickness of the metal shell is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process. FIGS. 8C-8G (discussed below) show details as to these phenomena.

Additionally, plasmon-phonon coupling may be used to reduce a resonance frequency through the tuning of the bands to a degree off resonance. This may be useful in optimizing resonance energy transfer processes for the purpose of coupling the core-shell nanoparticles to sensitive chromophores or drug targets. Accordingly, when a recipient 4 is outside of the shell, the recipient 4 will receive enhanced light $\lambda_2$ by the above-described plasmonic effect than would occur if the shell were absent from the structure.

In one example, FIG. 4A-1 shows UV-visible absorption spectra of cubic $Y_2O_3$ (lower trace) and gold-coated $Y_2O_3$ (upper trace) dispersed using 10 mM tri-arginine. Details of the preparation of the nanoparticle system are provided below. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$ (upper trace), on the other hand, exhibit a strong absorption band at 546 nm, which is characteristic of the plasmonics resonance band due to the gold shell around the $Y_2O_3$ cores. This feature is a plasmon band. If this feature were due to solid gold nanoparticles in solution, this feature would be centered at or below 530 nm. Moreover, red-shifting of the plasmon absorption to 546 nm is consistent with the presence of a gold shell around a dielectric core.

In one embodiment of the invention, the materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence. suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) $4f^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above with regard to FIG. 3. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teachings of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell 4, to enhance electron-phonon coupling and thereby increase upconversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. Further, in one embodiment of the invention, the coating can be a polymer. In one embodiment, this coating is provided on NaYF$_4$:Ln/NaYF$_4$ dielectric core. Such coatings can increase the upconversion efficiency relative to an uncoated upconverter.

In another embodiment of the invention, phonon modes of an undoped host-lattice (e.g., Y$_2$O$_3$) nanocrystals are modulated, for example, by Au, Ag, Pt, and Pd shells 4 of varying thicknesses. In various embodiments of the invention, the upconverter dielectric core and the shell system includes as upconverting nanocrystals Y$_2$O$_3$:Ln with NaYF$_4$ shells, Y$_2$O$_3$:Ln with Au(Ag,Pt) shells, NaYF$_4$:Ln with Y$_2$O$_3$ shells, NaYF$_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter. These core up converter or a core down converter structures offer advantages for biocompatibility as the core materials can be surrounded in a gold biocompatible shell.

Figure 4C:
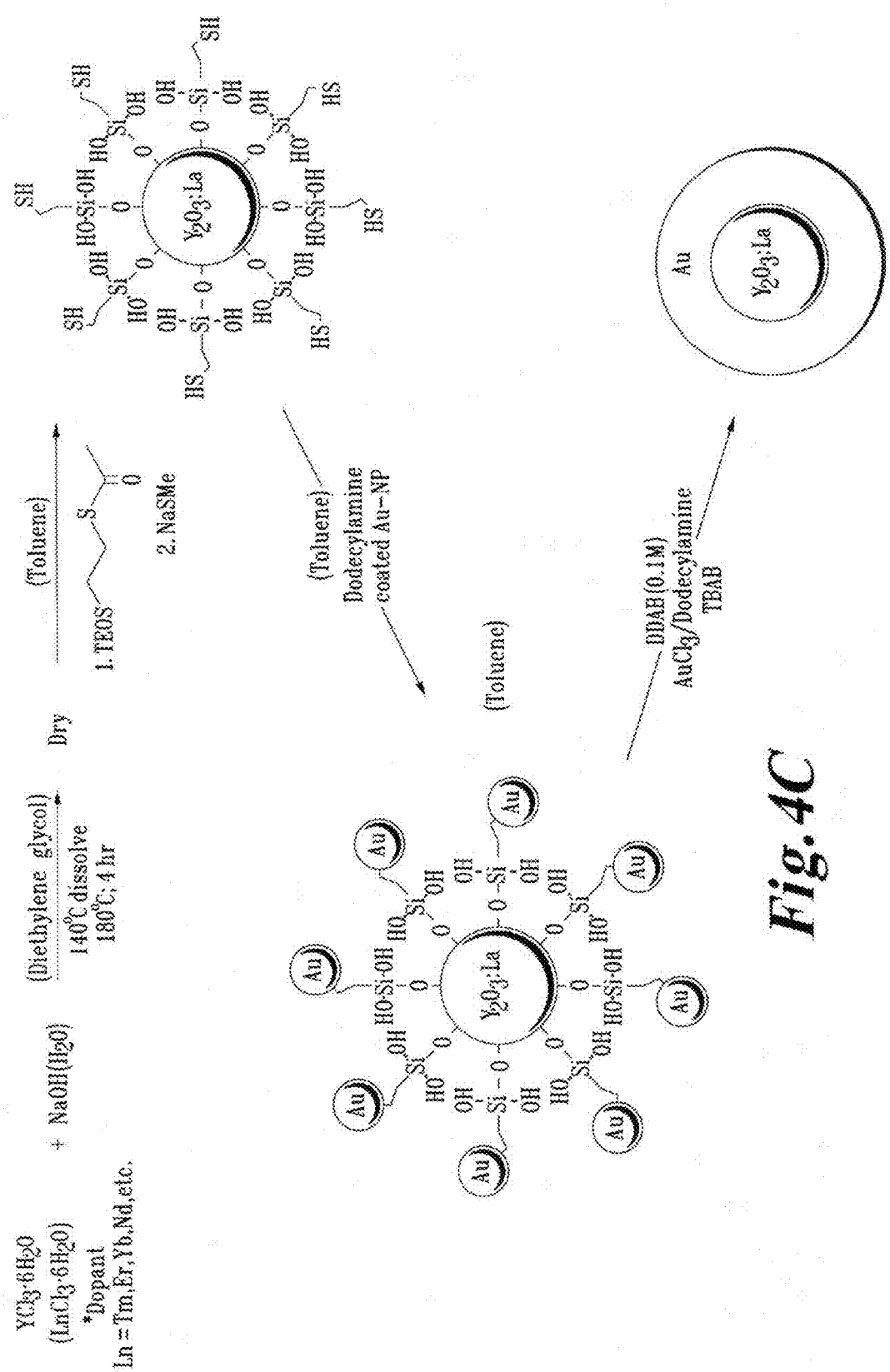
FIG. 4C is a schematic illustration of a process for forming and a resultant Ln-doped $Y_2O_3$ core with a Au shell.
Figures 1, 5A:
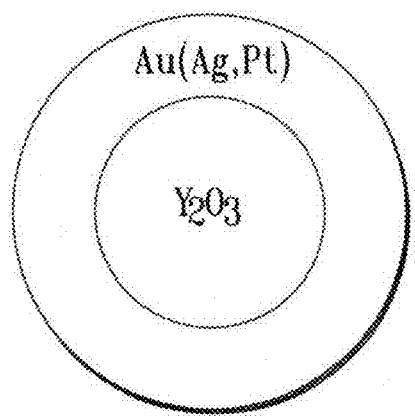
Figures 2, 5A:
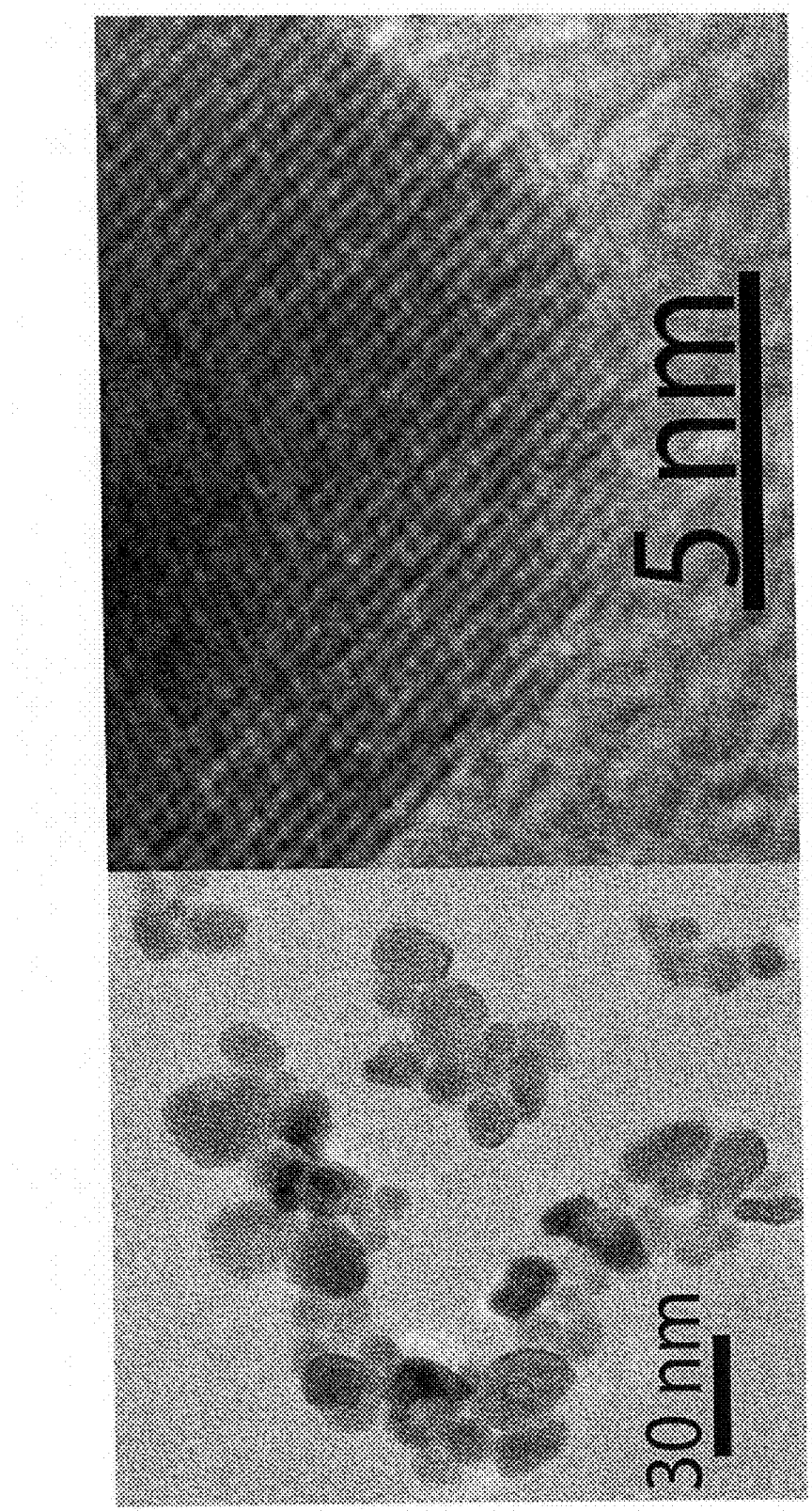

FIG. 4C is a schematic illustration of a process for forming and a resultant Ln-doped Y$_2$O$_3$ core with a Au shell. FIG. 5A-1 is a schematic depicting an Y$_2$O$_3$ dielectric particle coated with a sub 5 nm metallic coating. One illustrative method for producing sub-10 nm Ln-doped Y$_2$O$_3$ nanoparticles with a metal shell can be achieved through the polyol method. See Bazzi, R. et al. *Journal of Luminescence,* 2003, 102-103, 445-450, the entire contents of which are incorporated by reference. In this approach, yttrium chloride hexahydrate and lanthanum-series chloride hexahydrates are combined in an appropriate ratio with respect to their cation concentration into suspension with diethylene glycol (0.2 mol chloride per liter of DEG). To this suspension is added a solution of NaOH and water (0.2 mol/L and 2 mol/L, respectively). The suspension is heated to 140° C. in a solvent recondensing/reflux apparatus for a period of 1 hour. Upon completion of the 1 hour of heating the solution has become transparent and nucleation of the desired nanoparticles has occurred. The temperature is then increased to 180° C., and the solution is boiled/refluxed for 4 hours yielding Y$_2$O$_3$:Ln nanoparticles. This solution is then dialyzed against water to precipitate the nanoparticles or solvent is distilled off and excess water added to precipitate the same. The nanoparticles are collected through centrifugation and dried in vacuo.

The dried nanoparticles are then calcined at 800° C. for 2 hours to afford single phase, cubic Y$_2$O$_3$ nanocrystals with lanthanide dopants equally distributed through the Y$_2$O$_3$ nanocrystal. This methodology may be modified to allow for synthesis in a pressurized environment, thereby allowing for complete expression in the cubic phase, allowing for a shorter calcining times and lower temperatures leading to less nanoparticle agglomeration and size growth.

Figure 4D:
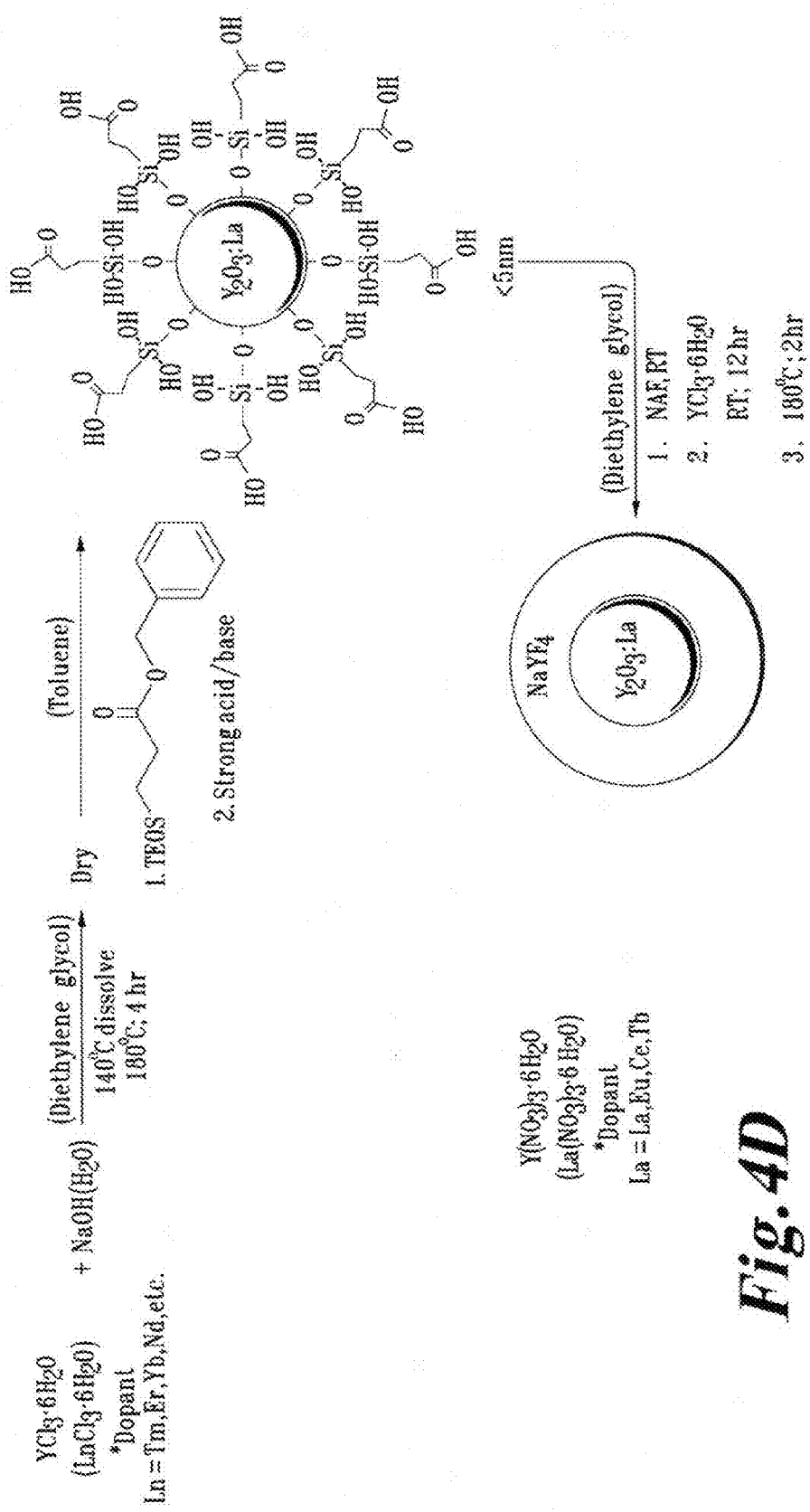
FIG. 4D is a schematic illustration of a process for forming and a resultant Ln-doped $Y_2O_3$ core with a $NaYF_4$ shell.

FIG. 4D is a schematic illustration of a process for forming and a resultant Ln-doped Y$_2$O$_3$ core with a NaYF$_4$ shell. In this embodiment of the invention, Ln-doped Y$_2$O$_3$ cores for example may be shelled with NaYF$_4$, Nd$_2$O$_3$, Ga$_2$O$_3$, LaF$_3$, undoped Y$_2$O$_3$, or other low phonon mode dielectric material using a secondary polyol approach following silyl protection of the core nanocrystal. It has been shown that low phonon mode host lattices (such as Y$_2$O$_3$, NaYF$_4$, etc.) are useful for aiding in the upconversion process. This has been attributed to the nature of electron-phonon coupling to low phonon modes and the removal of non-radiative decay processes within the host-lattice/ion crystal. Accordingly, in one embodiment of the invention, the dielectric core materials are made of low mode phonon host lattices (such as Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$, or alloys or combinations thereof, etc.).

Different sized Y$_2$O$_3$ NPs can also be synthesized via a combustion method developed by Song et al. In this method, Y(NO$_3$)$_3$ and glycine solution were heated to evaporate excess water until spontaneous ignition occurred. Cubic Y$_2$O$_3$ NPs can be obtained upon 2 hr of annealing at 500° C. One advantage of this method is that the Y$_2$O$_3$ particle size can be changed by varying the ratio between Y(NO$_3$)$_3$ and glycine. Another advantage is that different ratios of dopants (e.g. Yb and Er) can be added in the Y$_2$O$_3$ precursor solution and different doped Y$_2$O$_3$ NPs which have different emission properties can thus be synthesized. Due to insolubility, Y$_2$O$_3$ NPs are known to form precipitate in water. Upon functionalization with glutamic acid, Y$_2$O$_3$ NPs can result in a good suspension in water and the well-dispersed NPs shown in FIG. 5A-2. XRD measurement showed that the as-synthesized Y$_2$O$_3$ NPs have a cubic structure and this crystal structure is further proved by the lattice spacing as shown in FIG. 5A-2. Ligand substitution with excess 3-mercaptopropionic acid or 3-mercaptopropylphosphonic acid in the presence of refluxing diethylene glycol can then be used to functionalize these particles with Au nanoparticles in similar fashion to treatment with mercaptoalkylsilanes, as is described below.

Nanocrystals are then resuspended in toluene with sonication and treated with 2-triethoxysilyl-1-ethyl thioacetate (300 mM) in toluene. Volatile components of the reaction mixture are removed in vacuo and the remaining residue is resuspended in toluene and treated with NaSMe. Volatile components of the reaction mixture are again removed in vacuo and the remaining residue is purified through reprecipitation, centrifugation, and drying. The thiol-terminated, surface-modified nanocrystals are then resuspended in 0.1 M DDAB (didodecylammonium bromde) in toluene and a solution of colloidal gold nanoparticles (~1 nm in diameter) coated in dodecylamine (prepared as per Jana, et al. *J. Am. Chem. Soc.* 2003, 125, 14280-14281, the entire contents of which are incorporated herein by reference) is added. The gold shell is then completed and grown to the appropriate shell thickness through additions of AuCl$_3$ and dodecylamine in the presence of reducing equivalents of tetrabutylammonium borohydride. Thiol terminated organic acids may then be added to allow for increased water solubility and the completed gold metal shell, Ln-doped, Y$_2$O$_3$ nanoparticles may be separated in the presence of water through extraction or dialysis.

Dried Y$_2$O$_3$ nanoparticles are resuspended in toluene with sonication and treated with 2-triethoxysilyl-1-propionic acid, benzyl ester (300 mM) in toluene. Volatile components of the reaction mixture are removed in vacuo and the remaining residue is resuspended in toluene and treated with a strong base. Volatile components of the reaction mixture are again removed in vacuo and the remaining residue is purified through reprecipitation, centrifugation, and drying. The carboxyl-terminated, surface-modified nanocrystals are then resuspended in a solution of sodium fluoride in DEG and treated with yttrium nitrate hexahydrate at room temperature, stirring for 12 hours (for $NaYF_4$ exemplar). The reaction mixture is then brought to 180° C. for 2 hours to grow the $NaYF_4$ shell through Ostwald ripening. Nanoparticles are purified through reprecipitation, as described previously. Organic acid terminated polymers, polyethylene glycol, polyethynyleneimine, or other FDA approved, bioavailable polymer may then be added to allow for increased water solubility and the completed $NaYF_4$ shell, Ln-doped, $Y_2O_3$ nanoparticles may be resuspended in water for medical use.

In various embodiments of the invention, the upconverter dielectric core can be coated with thiol-terminated silanes to provide a coating of $SiO_2$ about the core of similar reactivity to $Y_2O_3$. These thiolated nanoparticles are then exposed to colloidal Au (1-2 nm) which associates to the nanoparticle surface and, with addition of $HAuCl_4$ and a reducing agent, Ostwald ripening coalesces the Au surface into a uniform shell of a designated thickness. Solubility enhancement of $NaYF_4$ and other $CaF_2$ lattices can be increased by the use of coupled trioctylphosphine-oleic acid, polyethylene glycol, and polyethyleneimine surfactants. These surfactants associate to the surface of the nanoparticles with functional head groups and are soluble in either organic or aqueous solvents to permit colloidal suspension of the nanoparticles.

In one embodiment of the invention, the above-described methodology is used to synthesize novel upconverting core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these novel material systems, the tuned ratio of core-to-shell diameter may permit a plasmon-phonon resonance which should amplify absorption of NIR light and/or upconverted emission. In these novel material systems, control of the core and shell diameters is one factor determining the size dependent effect and subsequent tuning of plasmon-phonon resonance.

In one embodiment of the invention, this methodology is used to synthesize novel mixed core-shell materials can include semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and trioctylphospine-oleic amine ($NaYF_4$ shell). All core-shell nanoparticles may further be solublized into a colloidal suspension with the addition of triarginine peptide, polyethylene glycol, and polyethyleneimine surfactants.

Since $Y_2O_3$ nanocrystals have a scintillation emission (down conversion) optimal for exciting drug derivatives of potential clinical importance, smaller nanocrystals offer advantages for biological targeting applications. Given the permeability of biological tissues to X-ray irradiation, down conversion from X-rays to visible light through $Y_2O_3$ nanocrystals offers a means of detecting the presence of nanoparticles coupled to biological malignancies (e.g. cancer, autoimmune degenerated tissue, foreign contaminants) through antibodies, Fab fragments, or cell-surface receptor specific peptides linked to the nanoparticle surface. Subsequently, down converting nanoparticles offer a means of generating UV/VIS/NIR light for photoactive drug activation directly at the treatment site, deep within biological tissue where UV and VIS light (if applied externally) would likely not penetrate. Furthermore, upconverting $Y_2O_3$:Ln nanocrystals can be utilized in one embodiment of the invention for their absorption and emissive properties within the NIR window applicable for medical imaging.

In one embodiment of the invention, small nanocrystals of these materials are prepared using rare-earth (RE) precursors (e.g. chloride, nitrate, alkoxides) which are mixed with a defined amount of water in a high boiling polyalcohol (e.g., diethylene glycol) solvent. The dehydrating properties of the alcohol and the high temperature of the solution promote a non-aqueous environment for the formation of oxide particles, as opposed to hydroxide, particles. Other solvents which can be used include: ethylene glycol, triethylene glycol, propylene glycol, dipropylene glycol, tripropylene glycol, etc. (thereby providing solvents with different boiling points). With these procedures, one expects sub-5 nm nanocrystals to be coated with Au, Ag, Pt, Pd (or combinations or alloys thereof) layers. FIGS. 5A-1 and 5A-2 illustrate respectively a schematic and an example of one such coated sub-5 nm nanocrystal. In other embodiments as discussed below, the metal structure can exist interior the dielectric and the relative position of the metal structure to the dielectric structure can enhance plasmon resonance.

Accordingly the synthesis of these nanocrystals and other dielectric core elements can follow the methods described below.

In particular, one method of forming yttrium oxide nanocrystals according to the present invention is to obtain precursors of the yttrium and rare earth ions in their salt forms, preferably in a chloride salt of the hexahydrate form, which is more soluble than non-hexahydrate forms. These salts are then combined in the correct molar ratios as listed below to create a yttrium oxide containing solution in a high boiling polyalcohol solvent with an added base of the correct proportion. An initial cation concentration of 0.2 moles per liter is mixed with a sodium hydroxide solution in water (0.2 moles per liter of sodium hydroxide per liter of reaction solution; 2 moles of $H_2O$ per liter per solution). The precursors were added together in the polyalcohol solvent, stirred for one hour at 140° C. After the salts are completely dissolved, the solution is brought to reflux at 180° C. and heated for four hours. The reaction is then cooled to room temperature yielding a transparent colloidal suspension of rare earth doped, yttrium oxide nanocrystals. The purification of this colloid produces the basic nanometer size of dielectric core shown in FIG. 5A-1. The metallic shell can then be prepared using the processes described below.

Similar methods can be employed for the preparation of the other upconversion materials described above, such as for example for the preparation of 1) nanoparticles of 2% neodymium and 8% ytterbium doped yttrium oxide, 2) europium and ytterbium doped yttrium oxide, and 3) any combination of rare earth trivalent ions doped into a neodymium oxide nanocrystal.

Figure 5B:
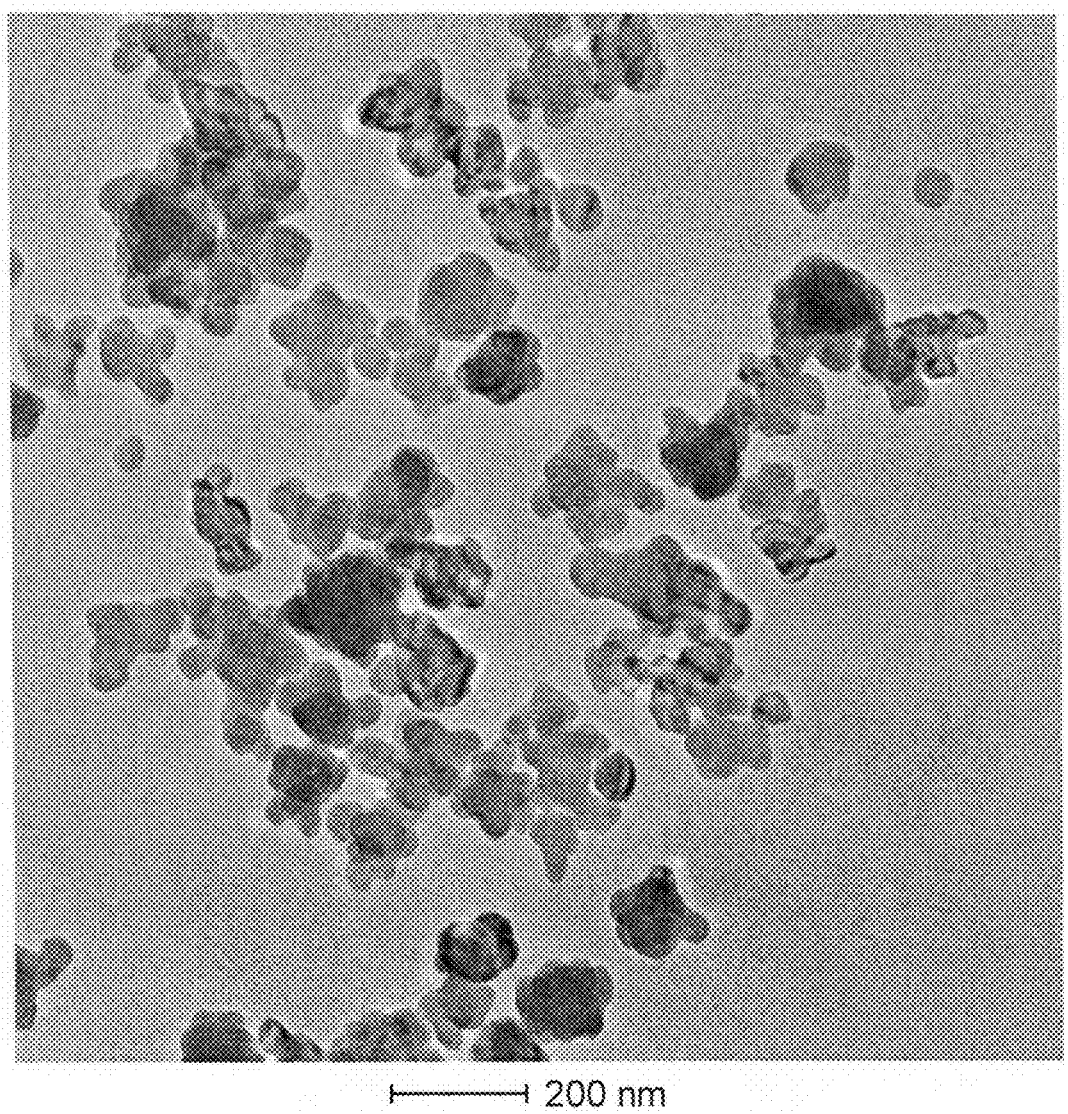
FIG. 5B is a micrograph showing $NaYF_4$ dielectric particles in the size range of ~70-200 nm range.

In another embodiment of the invention, $NaYF_4$ dielectric particles have been fabricated with individual particles in the ~70-200 nm size range as shown in FIG. 5B. To produce these particles NaCl, $TmCl_3$, $YCl_3$ and $YbCl_3$ stock solutions (0.2M) were prepared by dissolving the corresponding chlorides in water. A PEI stock solution (5%) was prepared by dissolving PEI ($M_n$~10,000) in water. 10 mL NaCl solution, 8 mL $YCl_3$ solution, 1.8 mL $YbCl_3$ solution and 0.2 mL $TmCl_3$ solution were added to a round-bottom flask containing 60 mL of ethanol and 20 mL of PEI solution. After stirring at room temperature for approximately 10 minutes, 2 mmol of $NH_4F$ was added and the solution was stirred for an additional 10 minutes. The solution was then transferred to a Teflonlined autoclave which was placed in an oven at 200° C. for 24 hours. After cooling to room temperature, the particles were isolated by centrifugation and then washed three times using 50/50 H$_2$O-ethanol. A white powder was obtained after rotary evaporation.

Figure 5C:
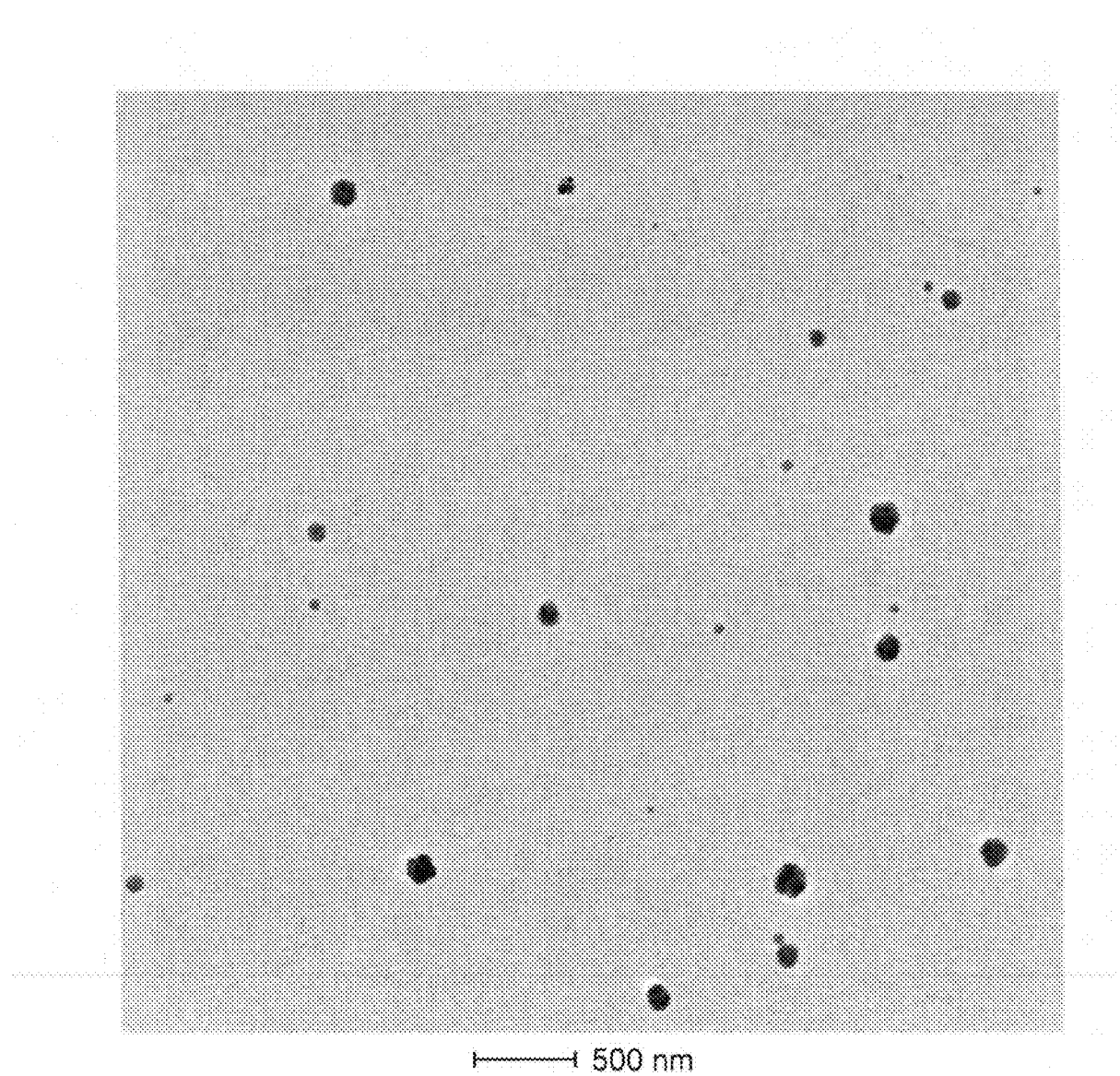
FIG. 5C is a micrograph showing $NaYF_4$ dielectric particles with two size distributions of ~50 nm and ~150 nm.
Figure 5D:
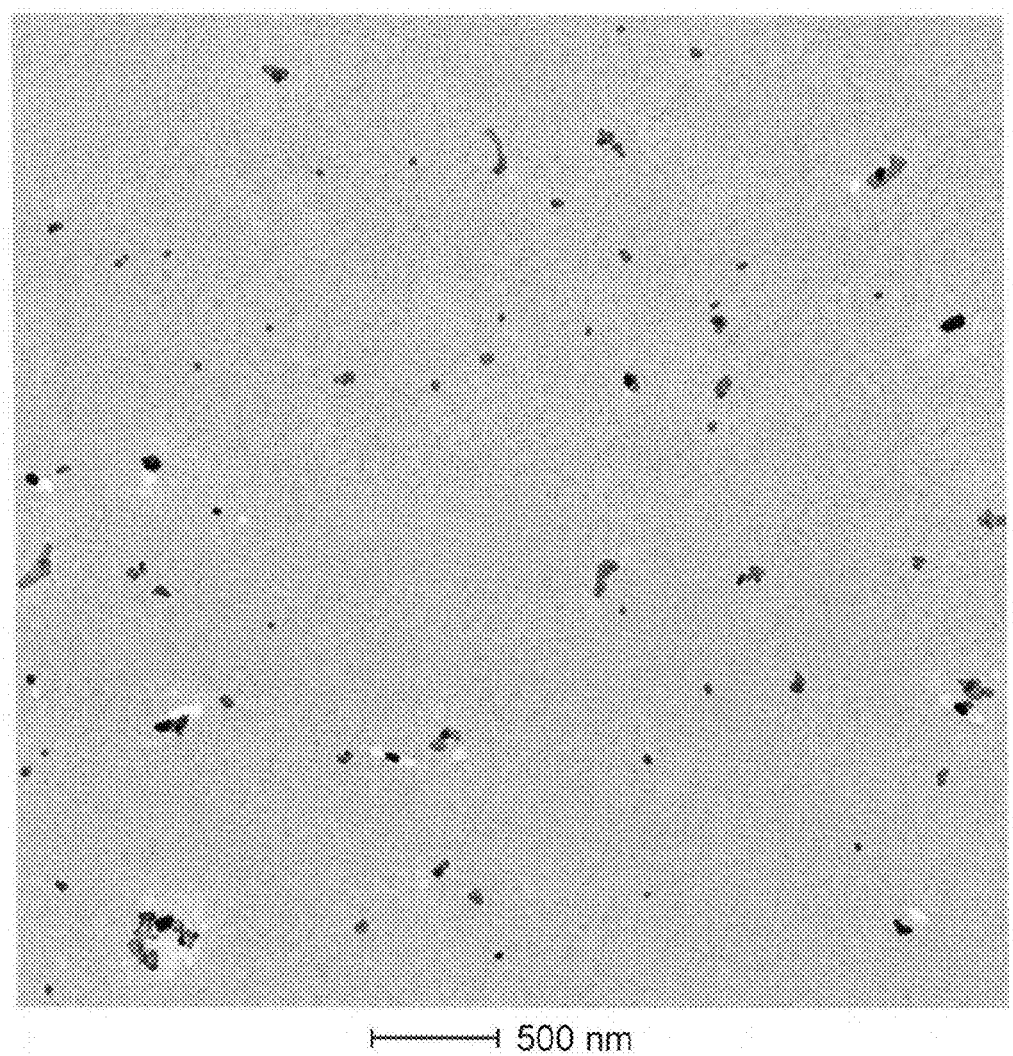
FIG. 5D is a micrograph showing $YbF_3$ dielectric particles of a size of 35 nm+/−5 nm.
Figure 5E:
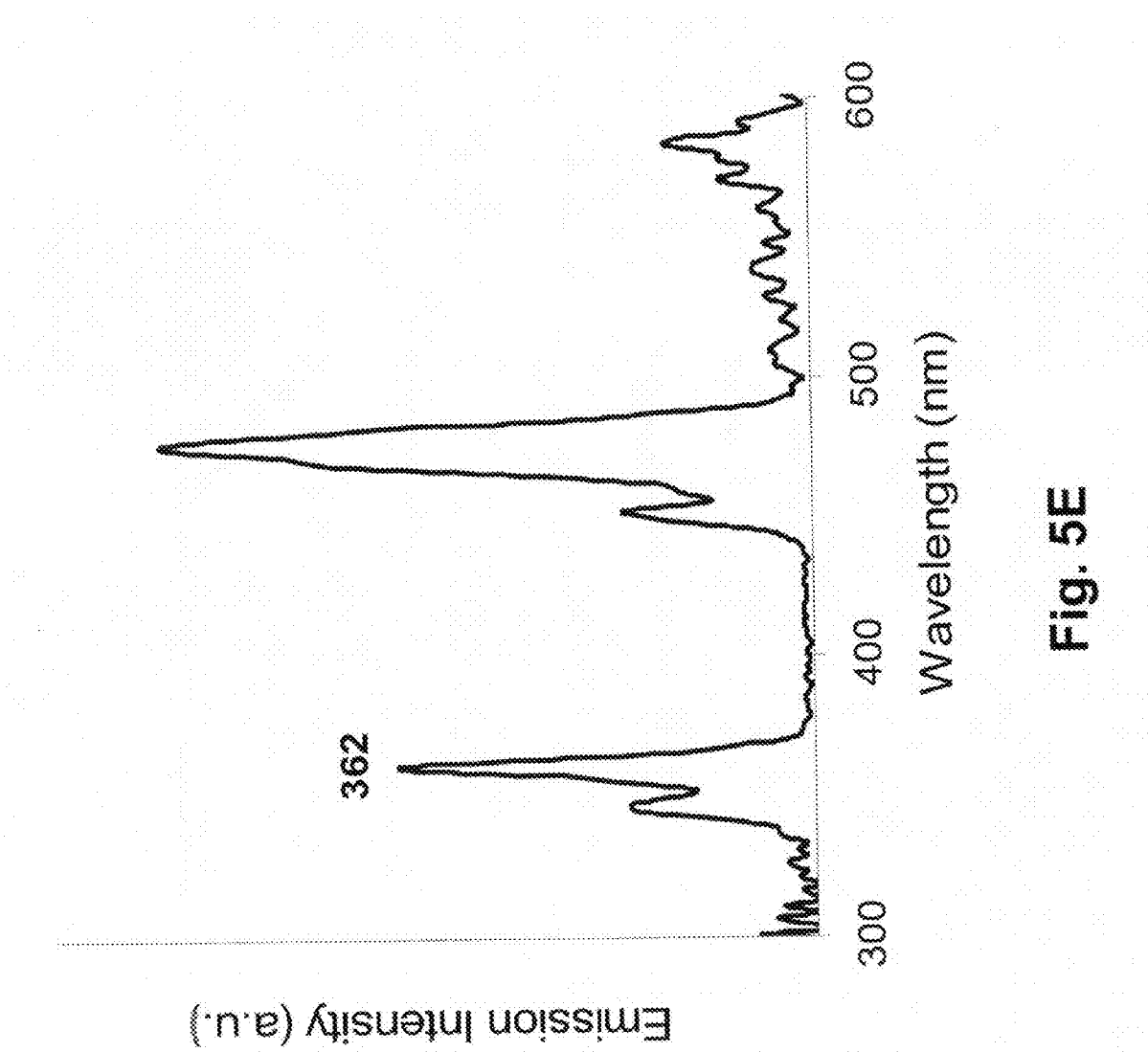
FIG. 5E is an optical emission spectrum from $YbF_3$; Tm (2%) dielectric particles, excited at 980 nm.
Figure 5F:
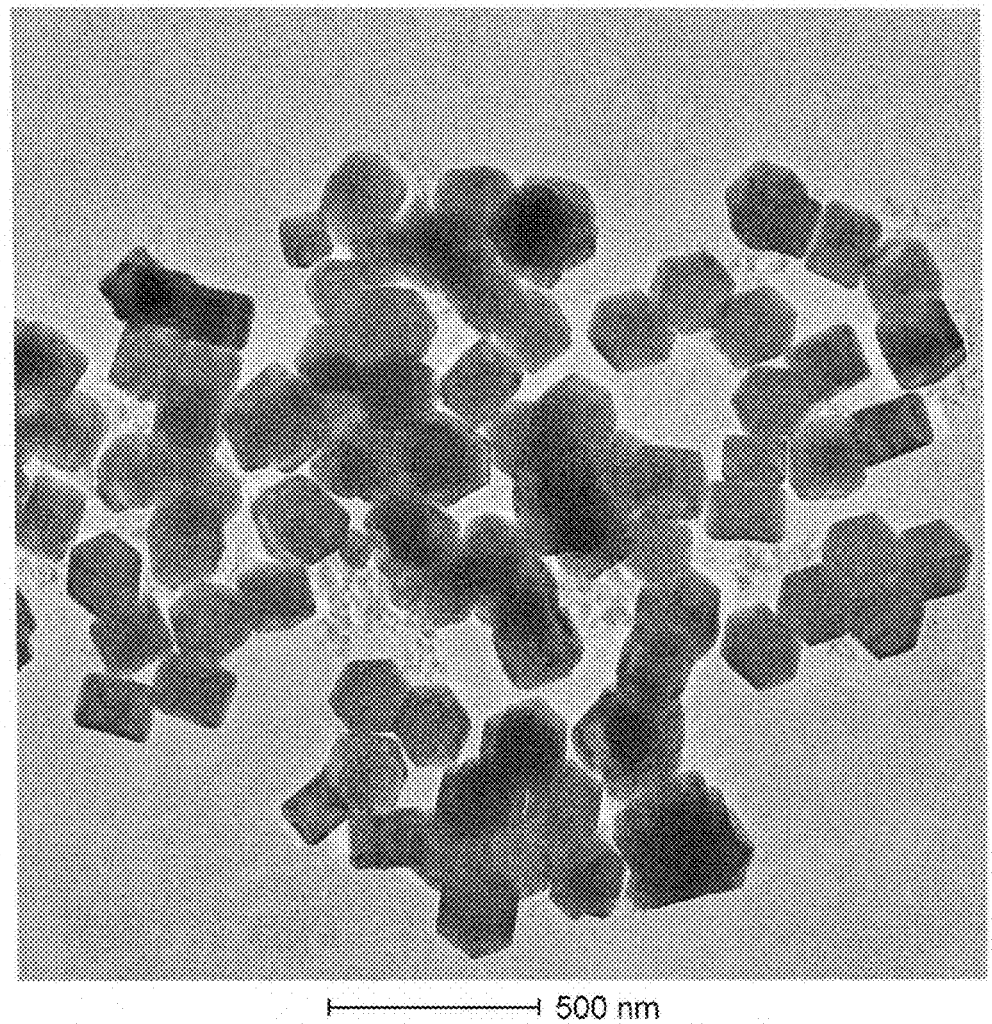
FIGS. 5F-5I are micrographs showing $NaYbF_4$ dielectric particles in the ~20-150 nm size range.
Figure 5G:
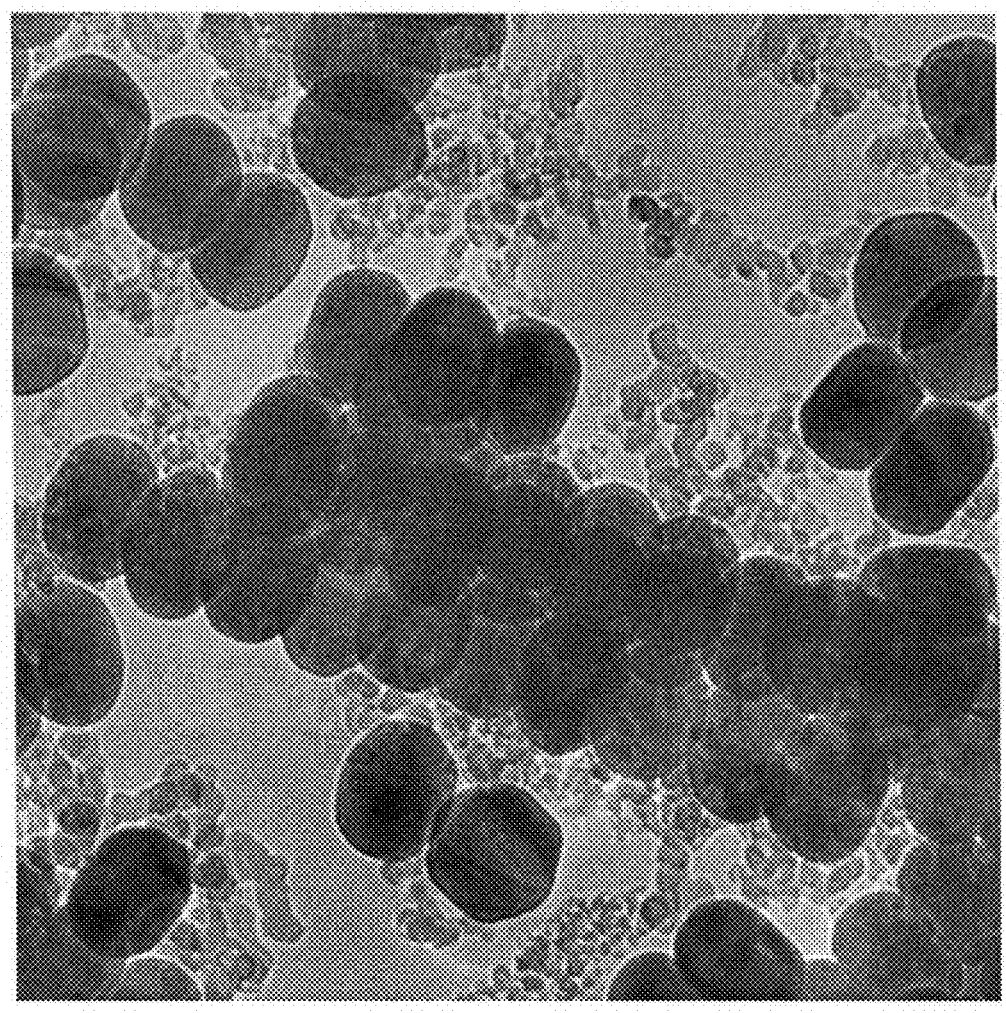
Figure 5H:
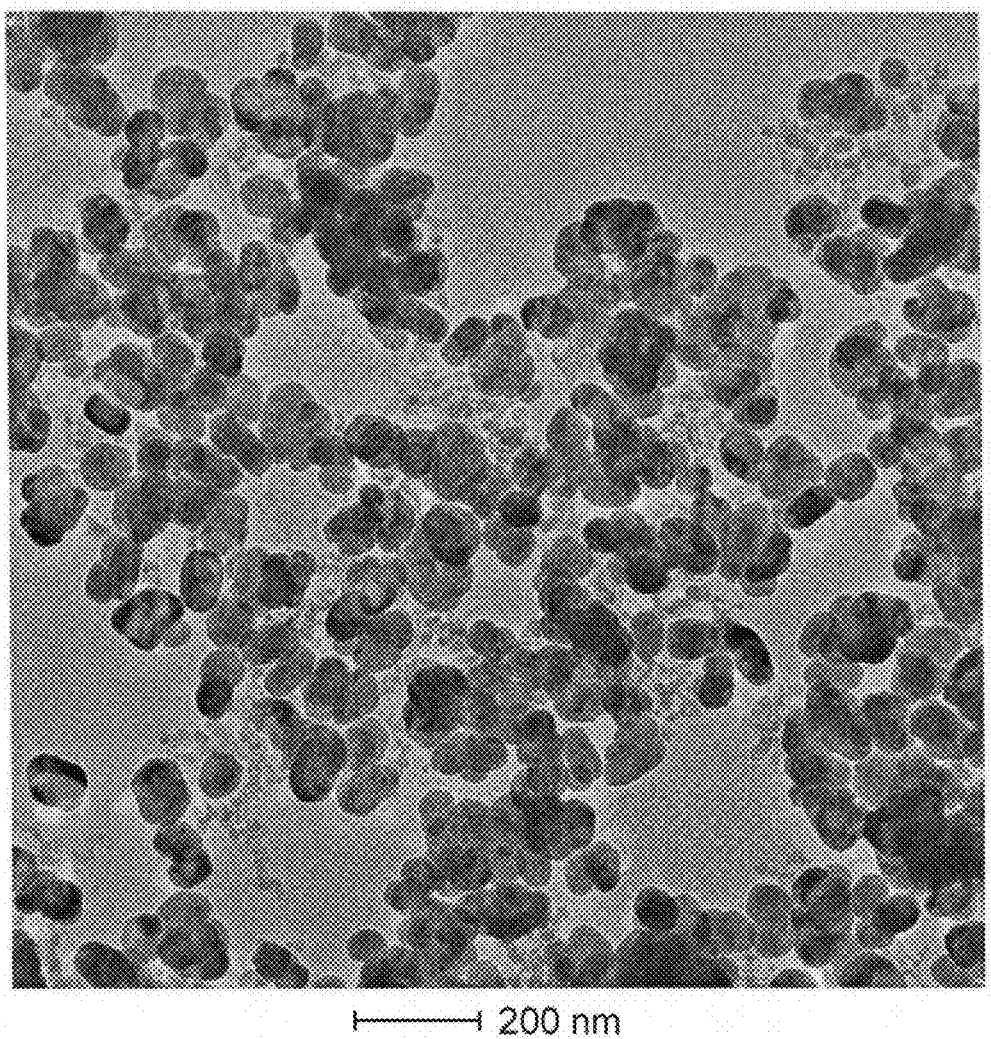
Figure 5I:
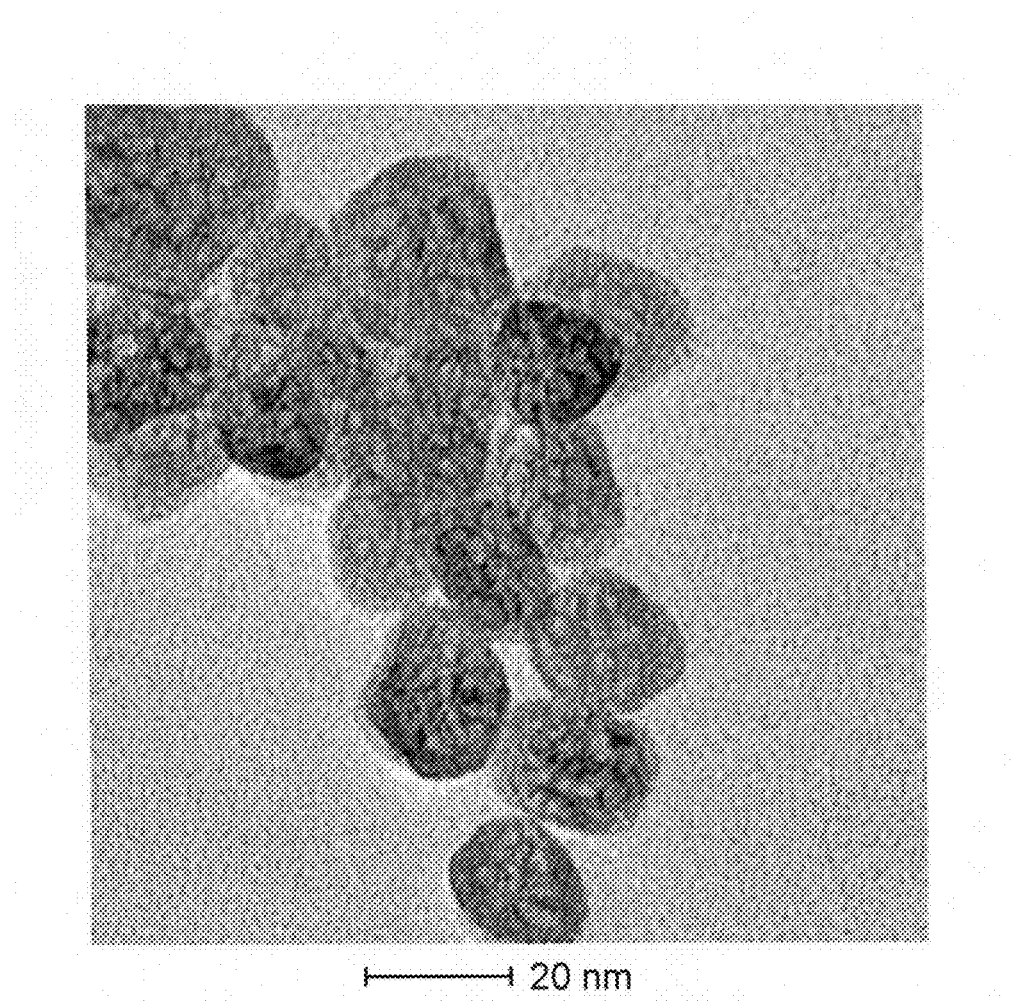

Further, NaYF$_4$ dielectric particles have been produced and isolated into dispersed particles with two size distributions of ~50 nm and ~150 nm, as shown in FIG. 5C. The procedure to generate these particles is the same as that listed above, except that the YbCl$_3$ stock solution was prepared by dissolving Yb$_2$O$_3$ in HCl. Further, YbF$_3$ dielectric particles have been produced and isolated into homogeneous particles of a size of 35 nm+/−5 nm, as shown in FIG. 5D. Generation of these particles was similar to that listed above, except that the concentrations of all the salts were halved (the PEI concentration remaining constant), and YbCl$_3$ was used instead of YCl$_3$. As such, two YbCl$_3$ stock solutions (0.1 M) were prepared; the first by dissolving YbCl$_3$.6H$_2$O in water and the second by dissolving Yb$_2$O$_3$ in concentrated hydrochloric acid. The remainder of the synthetic methodology remained the same. An optical emission spectrum from these NaYF$_4$ dielectric core particles, excited at 980 nm, is shown in FIG. 5E.

In another embodiment of the invention, NaYbF$_4$ dielectric particles have been fabricated with individual particles in the ~20-200 nm size range as shown in FIGS. 5F, 5G, 5H, and 5I. These particles were generated through a thermal decomposition method based on the work of Boyer, J-C. et al. *Nano Lett.*, 2007, 7(3), 847-852 and Shan, J. et al. *Nanotechnology*, 2009, 20, 275603-275616, the entire contents of which are incorporated by reference. The particles were prepared by composing a slurry of NaTFA (2.5-4 mmol), 34 mL 1-octadecene, and 6 mL oleic acid, Y(TFA)$_3$, Yb(TFA)$_3$, and Ln(TFA)$_3$ (Ln=Tm) in given proportion totaling 2 mmol of trifluoroacetate salt. The slurry was heated under vigorous stirring to 125° C. in a 100 mL, 2-neck round bottom flask with magnetic stir bar and reflux condenser until full dissolution occurred and any residual water was removed through a vent needle. 6 mL trioctylphosphine or oleic acid was then added. The reaction apparatus was then transferred to a molten salt bath (KNO$_3$:NaNO$_3$; 50:50 by mol %) held at temperatures varying from 350-414° C. and held at temperature for 15-60 minutes. The reaction was then cooled to RT, poured into an equivalent volume of absolute ethanol, sonicated, vortexed, and centrifuged at 21 k rcf (approx. 14 k RPM) for 30 minutes. The resulting pellet was resuspended and centrifuged in similar fashion with hexanes, followed by two washes of 50:50; water:ethanol, and a final wash of absolute ethanol. The purified nanocrystals were then dried in air overnight.

Figure 6E:
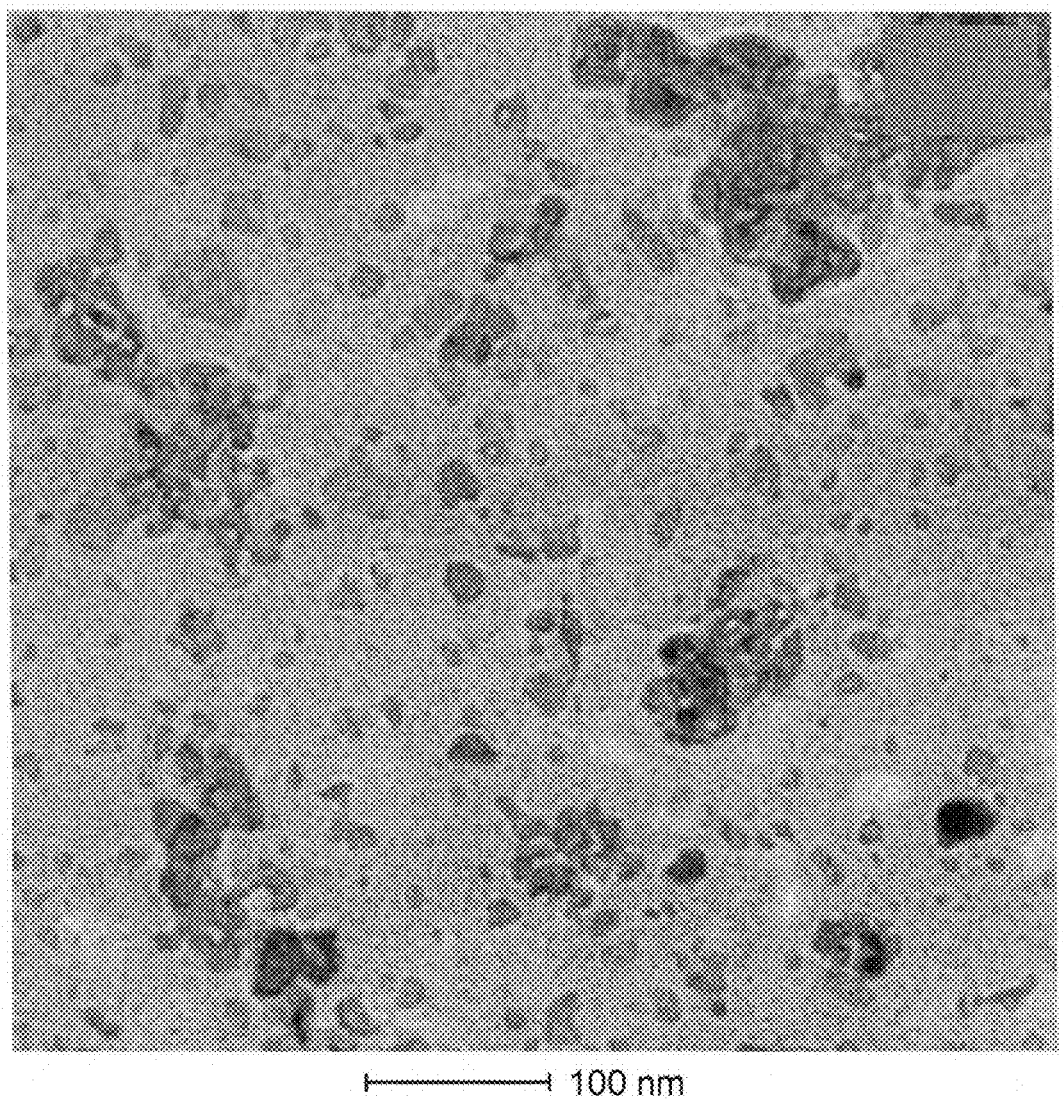
FIG. 6E is a TEM micrograph of uncoated $Y_2O_3$ nanoparticles.

FIG. 6A shows some of the various embodiments of the upconverter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer. The configurations (while shown in the FIG. 6 series with UC-containing materials) would be applicable for enhancement for down converting materials. Moreover, in one embodiment of the invention, dielectric spacers (for examples silicates as discussed below) can be used with the structure of FIG. 6A-*b* to space apart the particle type metallic structures. In another embodiment of the invention, dielectric spacers can be used with the structure of FIG. 6A-*d*, f to space apart the metal layers, whether or not these layers are partial metal layers as in FIG. 6A-*d* or continuous metal layers as in FIG. 6A-*f*. See FIGS. 6B-*b*, d, and f.

The plasmonic properties of various metallic structures, which have been investigated in the art and are suitable for the invention, include metallic nanoshells of spheroidal shapes [S. J. Norton and T. Vo-Dinh, "*Plasmonic Resonances of Nanoshells of Spheroidal Shape*", IEEE Trans. Nanotechnology, 6, 627-638 (2007)], oblate metal nanospheres [S. J. Norton, T. Vo-Dinh, "*Spectral bounds on plasmon resonances for Ag and Au prolate and oblate nanospheroids*", J. Nanophotonics, 2, 029501 (2008)], linear chains of metal nanospheres [S. J. Norton and T. Vo-Dinh, "*Optical response of linear chains of metal nanospheres and nanospheroids*", J. Opt. Soc. Amer., 25, 2767 (2008)], gold nanostars [C. G. Khoury and T. Vo-Dinh, "*Gold Nanostars for Surface-Enhanced Raman Scattering: Synthesis, Characterization and Applications*", J. Phys. Chem C, 112, 18849-18859 (2008)], nanoshell dimmers [C. G. Khoury, S. J. Norton, T. Vo-Dinh, "*Plasmonics of 3-D Nanoshell Dimers Using Multipole Expansion and Finite Element Method, ACS Nano*, 3, 2776-2788 (2009)], and multi-layer metallic nanoshells [S. J. Norton, T. Vo-Dinh, "*Plasmonics enhancement of a luminescent or Raman-active layer in a multilayered metallic nanoshell*", Applied Optics, 48, 5040-5049 (2009)]. The entire contents of each of the above noted references in this paragraph are incorporated herein by reference. In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$ This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 6A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

FIG. 6B shows yet other embodiments of upconversion structures that have a dielectric layer between the metal and the UC materials.

FIG. 6C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi layer metal nanoshells covering an UC spheroid core, (h) multi-nanoparticle structures, (i) a metal nanocube and nanotriangle/nanoprism, and (j) a metal cylinder.

FIG. 6D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 6D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (I) an UC material-containing nanoparticle covered with metal nanoshell, (g) an UC material-containing nanoparticle covered with metal nanoshell with protective coating layer.

Gold Nanoshell Preparations with Dielectric Cores:

The invention can utilize a wide variety of synthesized metallic-coated core-shell nanoparticles prepared from a number of wet chemical procedures. The techniques described below are provided for the purposes of illustration and not for the purpose of limiting the invention to these particular techniques. In the invention, gold nanoshells can be prepared using the method or similar methods described in Hirsch L R, Stafford R J, Bankson J A, Sershen S R, Rivera B, Price R E, Hazle J D, Halas N J, West J L (2003) *Nanoshell-mediated near infrared thermal therapy of tumors under MR Guidance*. Proc Natl Acad Sci 100:13549-13554, the entire contents of which are incorporated herein by reference. This method uses a mechanism involving nucleation and then successive growth of gold nanoparticles around a dielectric core. Dielectric nanoparticles of sizes less than for example 100, 200, or 300 nm, as well as larger sizes, used for the core of the nanoshells, can then be monodispersed in a solution of 1% APTES in EtOH. The gold "seed" colloid can then be synthesized using the Frens method (see details below) and deposited onto the surface of the dielectric nanoparticles via molecular linkage of silyl terminated amine groups. The gold "seed" covers the aminated nanoparticle surface, first as a discontinuous gold metal layer and gradually growing forming a continuous gold shell.

Additionally, various photochemical methods have been reported for the fabrication of gold nanoparticles and gold films [Refs: A. Pal, T. Pal, D. L. Stokes, and T. Vo-Dinh, "*Photochemically prepared gold nanoparticles: A substrate for surface-enhanced Raman scattering*", Current Science, 84, 1342-1346 (2003; A. Pal, D. L. Stokes and T. Vo-Dinh, "*Photochemically Prepared Gold Metal film in a Carbohydrate-based Polymer: a Practical Solid substrate for Surface-enhanced Raman Scattering*, Current Science, 87, 486-491 (2004)]. These articles in their entirety are incorporated herein by reference. The invention in various embodiments utilizes a class of core-shell nanoparticles based on rare earth oxide (REO) cores having noble metal shells. A number of nanoparticle/metal shell systems can be fabricated using the photochemical procedures described below or other suitably modified procedures.

The REO core material is a well-suited core material for the invention due to doping for either upconversion- or downconversion-based fluorescence, and due to the fact that the plasmonically-active metal shells can be easily functionalized with targeting peptides, fluorophores, or SERS-active molecules using well-established techniques. For the purpose of illustration, the design and fabrication of one such hybrid nanoparticle system is described below where the nanoparticle system includes an yttrium oxide ($Y_2O_3$) core, a gold (Au) shell, and a short arginine and lysine-rich peptide, e.g., transactivator of transcription (TAT) residues 49-57, functionalized with various fluorescent dyes using N-hydroxysuccinimide (NHS) coupling chemistry. This peptide and similar molecules can show greatly enhanced cellular uptake and nuclear localization of DNA, nanoparticles, liposomes, peptides and proteins. Further, this particular portion of the TAT sequence has been shown to be non-toxic, making the resulting fluorescently-labeled nanoparticles potentially suitable for in vivo imaging applications.

Materials:

Yttrium oxide nanoparticles (e.g., 99.9% purity, 32-36 nm average diameter, cubic crystal structure) were obtained from Nanostructured and Amorphous Materials, Inc. (Houston, Tex.). Tri-arginine (H-Arg-Arg-Arg-OH) acetate was obtained from Bachem (Torrance, Calif.), and gold tribromide ($AuBr_3$) was obtained from Alfa Aesar (Ward Hill, Mass.). Dimethyl sulfoxide (DMSO) was purchased from CalBioChem (La Jolla, Calif.) and was used as received. A cysteine-modified version of the TAT peptide (residues 49-57, sequence Arg-Lys-Lys-Arg-Arg-Arg-Gln-Arg-Arg-Cys-$CONH_2$, molecular weight 1442 g/mol, hereafter referred to as "TAT") was obtained from SynBioSci (Livermore, Calif.). Succinimidyl-[4-(psoralen-8-yloxy)]butyrate (SPB) was obtained from Pierce (Rockford, Ill.), and Marina Blue, Alexa 350 and Alexa 546 NHS esters were obtained from Invitrogen (Carlsbad, Calif.). Ultrapure 18.2 MΩ/deionized (DI) water purified with a Millipore Synergy filtration system (Millipore, Billerica, Mass.) was used to make all solutions.

Yttrium Oxide Dispersion:

Tip sonication was used to disperse autoclaved $Y_2O_3$ nanoparticles at 10 mg/mL in 10 mM tri-arginine solution which had been pre-filtered at 0.22 microns. Following moderate mixing in a sealed, sterile container on a stir plate for 24 hours to allow tri-arginine attachment and improved $Y_2O_3$ dispersion, the solution was centrifuged at 8200 relative centrifugal force (RCF) to remove fused particles and large aggregates.

Gold Shell Formation:

Supernatant from the initial $Y_2O_3$ dispersion was diluted 1:1 (v/v) with 5.7 mM $AuBr_3$ dissolved in sterile DI water and pre-filtered at 0.22 microns, then exposed to high-intensity fluorescent light (Commercial Electric, Model 926) for 16 hours in a sealed, sterile glass container with moderate mixing. During the time course of this photochemical process, the reddish-brown $AuBr_3$ solution turned yellow immediately after addition of the $Y_2O_3$ in tri-arginine; became clear and visually colorless; then developed an intense purple color as Au shells formed on the $Y_2O_3$ cores. In the absence of the $Y_2O_3$ cores, neither the intense purple color associated with plasmonic absorption by gold nanoshells nor the deep red color associated with solid gold nanoparticles appears. Use of heat rather than light in the presence of $Y_2O_3$ particles tends to produce a large number of solid gold nanoparticles rather than or in addition to core-shell structures, as evidenced by strong absorption at ~530 nm.

Particle Functionalization with TAT:

Gold-coated $Y_2O_3$ nanoparticles were centrifuged at 16 k RCF for 15 minutes, and the pellet was re-dispersed in a 50% volume of sterile DI water by a short tip sonication. The particles were further purified by two additional centrifugations at 16 k RCF for 15 minutes each, with redispersion in a 100% volume of sterile DI water following the second centrifugation and final redispersion in a 100% volume of 1 mg/mL (0.7 mM) TAT peptide dissolved in sterile DI water and pre-filtered at 0.22 microns.

This solution was vigorously mixed at room temperature for one hour to allow thiol anchoring to the gold shell via the c-terminal cysteine residue. Variations in the TAT concentration, temperature and reaction time can all change the extent of surface coverage and the potential for further functionalization.

Peptide Functionalization with Dye Molecules:

The TAT-functionalized, gold-coated $Y_2O_3$ particles were purified by triplicate centrifugation at 16 k RCF, with the first two re-dispersions in sterile DI water and the final re-dispersion in sterile 100 mM bicarbonate buffer at pH 9.0. Each NHS ester (SPB, Alexa 350, Marina Blue and Alexa 546) was dissolved at 10 mg/mL in dimethyl sulfoxide (DMSO), and 100 microliters of a given NHS-functionalized dye were added to a 1 mL aliquot of TAT-functionalized, gold-coated $Y_2O_3$. The solutions were reacted for one hour at room temperature in the dark with vigorous mixing to allow attachment of dye molecules to primary amines along the TAT peptide (such as the attachment of N terminus and the lysine side chains).

The psoralen-functionalized nanoparticles were centrifugally cleaned using a 1:1 volume of DMSO in water to remove any residual SPB crystals, then all dye-functionalized core-shell nanoparticles were purified by triplicate centrifugation at 16 k RCF for 15 minutes. Each centrifugation step was followed by re-dispersion in a 100% volume of sterile DI water. Presuming removal of 95+% of non-attached dye molecules during each centrifugation step, no more than 0.01% of the unbound dye is estimated to remain in the final solution.

Figure 6F:
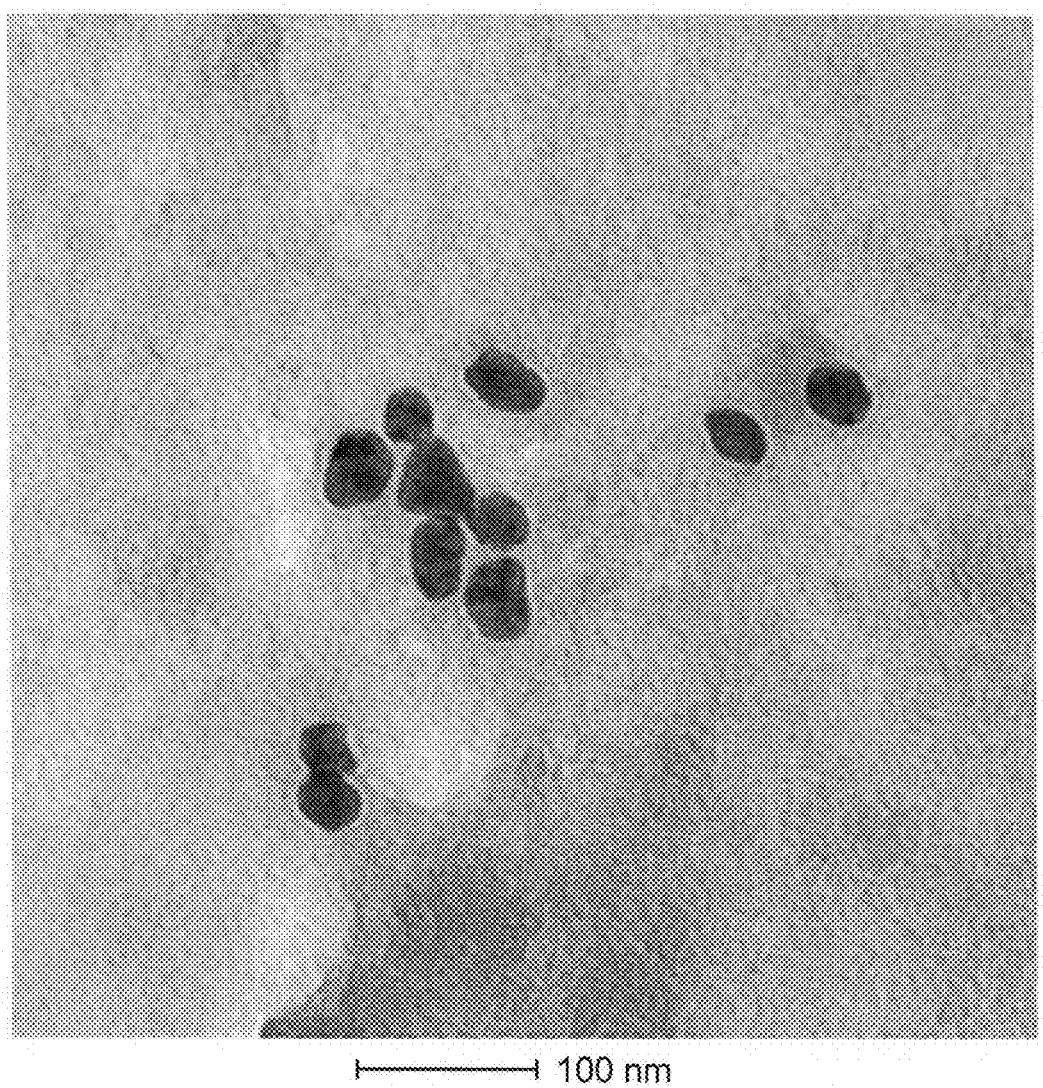
FIG. 6F is a TEM micrograph of gold coated $Y_2O_3$ nanoparticles of the invention.

Nanoparticle Characterization:

Transmission electron microscopy (TEM) provides additional evidence for the presence of gold-coated $Y_2O_3$ particles. FIG. 6E, for example, shows a representative TEM image of as purchased $Y_2O_3$ nanoparticles. The particles are quite polydisperse, but exhibit an average diameter of approximately 35 nm. FIG. 6F shows similar images for $Y_2O_3$ particles coated with a gold shell using the synthetic procedure described above. Like the underlying $Y_2O_3$ cores, the gold-coated yttrium oxide particles are somewhat polydisperse with an average diameter of approximately 50 nm.

Figure 6G:
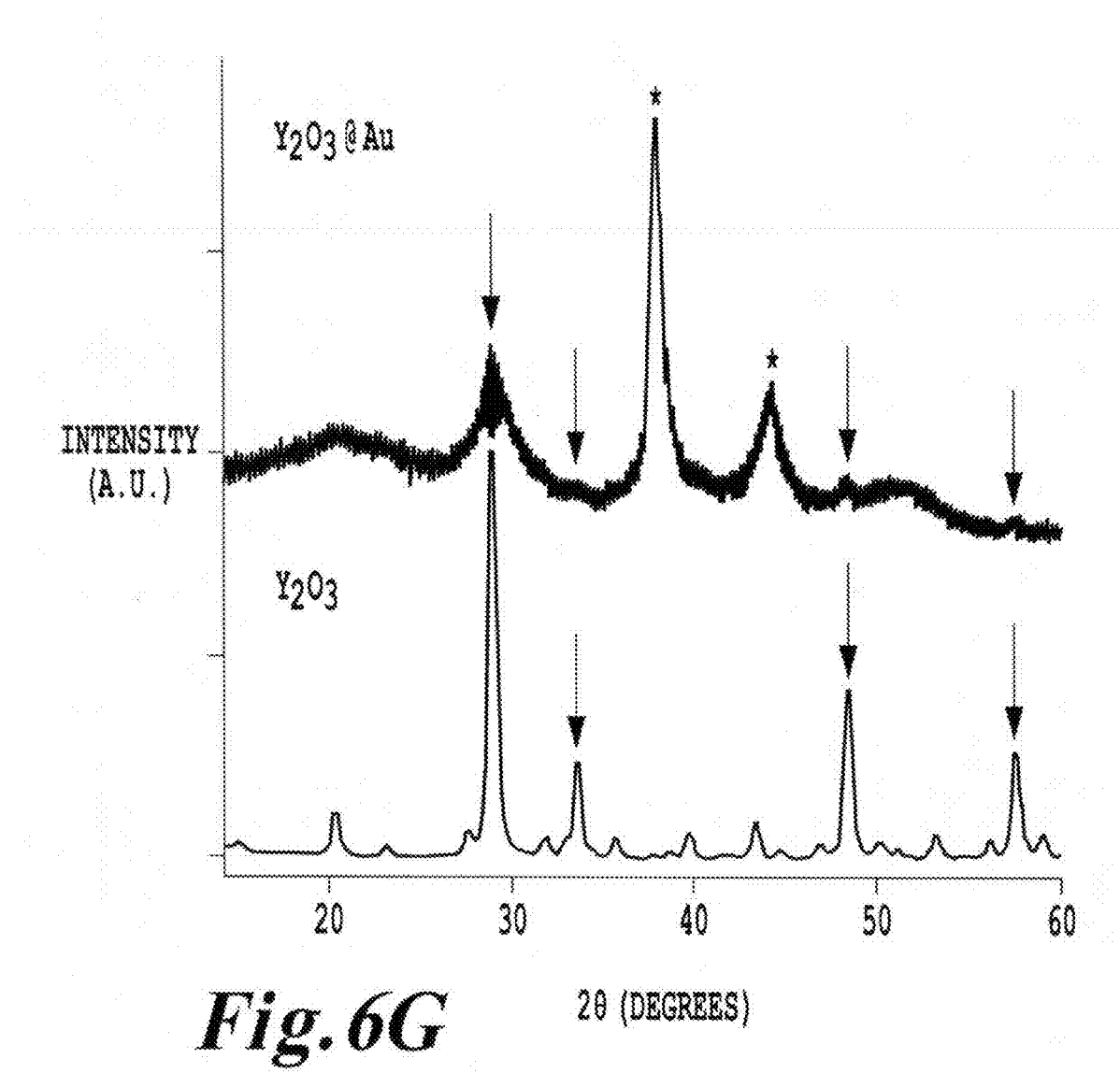
FIG. 6G is an X-ray diffraction data from gold coated $Y_2O_3$ nanoparticles of the invention.

Perhaps the most conclusive demonstration that these nanoparticles are in fact gold-coated $Y_2O_3$ comes from comparison of X-ray diffraction data (XRD). FIG. 6G shows diffractograms for both the initial cubic $Y_2O_3$ nanoparticles (lower trace) and the final gold-coated core-shell particles (upper trace). Strong peaks at $2\theta=29$, 33.7, 48.5 and 57.5 degrees in the lower trace are indicative of cubic $Y_2O_3$. The most pronounced features in the upper trace are two gold-associated peaks at $2\theta=38.2$ and 44.4 degrees. In addition, the four strongest cubic $Y_2O_3$ peaks at $2\theta=29$, 33.7, 48.5 and 57.5 degrees are also visibly superimposed on the baseline diffractogram from the gold nanoshells. The reason for the broadening of the $Y_2O_3$ peak at $2\theta=29$ degrees is not definite, but may be a result of gold-$Y_2O_3$ interactions or, alternatively, the preferential size-selection of small $Y_2O_3$ particles during the 8200 RCF centrifugation used to remove large $Y_2O_3$ particles and aggregates.

Gold Colloidal Nanoparticles

In various embodiments of the invention, gold nanoparticles without a dielectric core are used in the medium being irradiated to enhance either the intensity of the initiation energy (i.e., the primary source: for example an IR laser for upconversion or an xray beam for down conversion) or to enhance the light generated from the upconverting or down converting nanoparticles). The techniques described below for the fabrication of metal nanoparticles with and without cores and with and without additional layers and linkages are provided for the purposes of illustration and not for the purpose of limiting the invention to these particular techniques. Indeed, the invention can utilize a wide variety of synthesized metallic, multi-layer core-shell nanoparticles prepared from a number of wet chemical procedures. Exemplary parameters and procedures for producing these nanoparticles systems are described below. Starting materials included ultrapure water (deionized), $HAuCl_4*3H_2O$, $AgNO_3$, $Y_2O_3$, NaOH, $NH_4OH$, sodium citrate, hydroxylamine hydrochloride, hydrazine monohydrate, sodium borohydride, aminopropyltrimethoxy silane (APTMS), sodium silicate, tetraethyl orthosilicate (TEOS), methanol, ethanol, isopropanol, oleic acid, and oleylamine.

a. Synthesis of Gold Nanoparticles

The Frens method (see G. Frens, Nat. Phys. Sci. 241 (1973) 20, the entire contents of which are incorporated herein by reference) can be used to synthesize gold nanoparticles. In this process, $5.0 \times 10^{-6}$ mol of $HAuCl_4$ was dissolved in 19 mL of deionized water. The resulting solution was faintly yellow. The solution was heated and vigorously stirred in a rotary evaporator for 45 minutes. One mL of 0.5% sodium citrate was added, and the solution was stirred for an additional 30 minutes. Addition of sodium citrate has multiple purposes. First, citrate acts as a reducing agent. Second, citrate ions that adsorb onto the gold nanoparticles introduce surface charge that stabilizes the particles through charge repulsion, thus preventing nanocluster formation.

b. Synthesis of Gold Nanoparticles having 15-nm Diameter

Figure 6H:
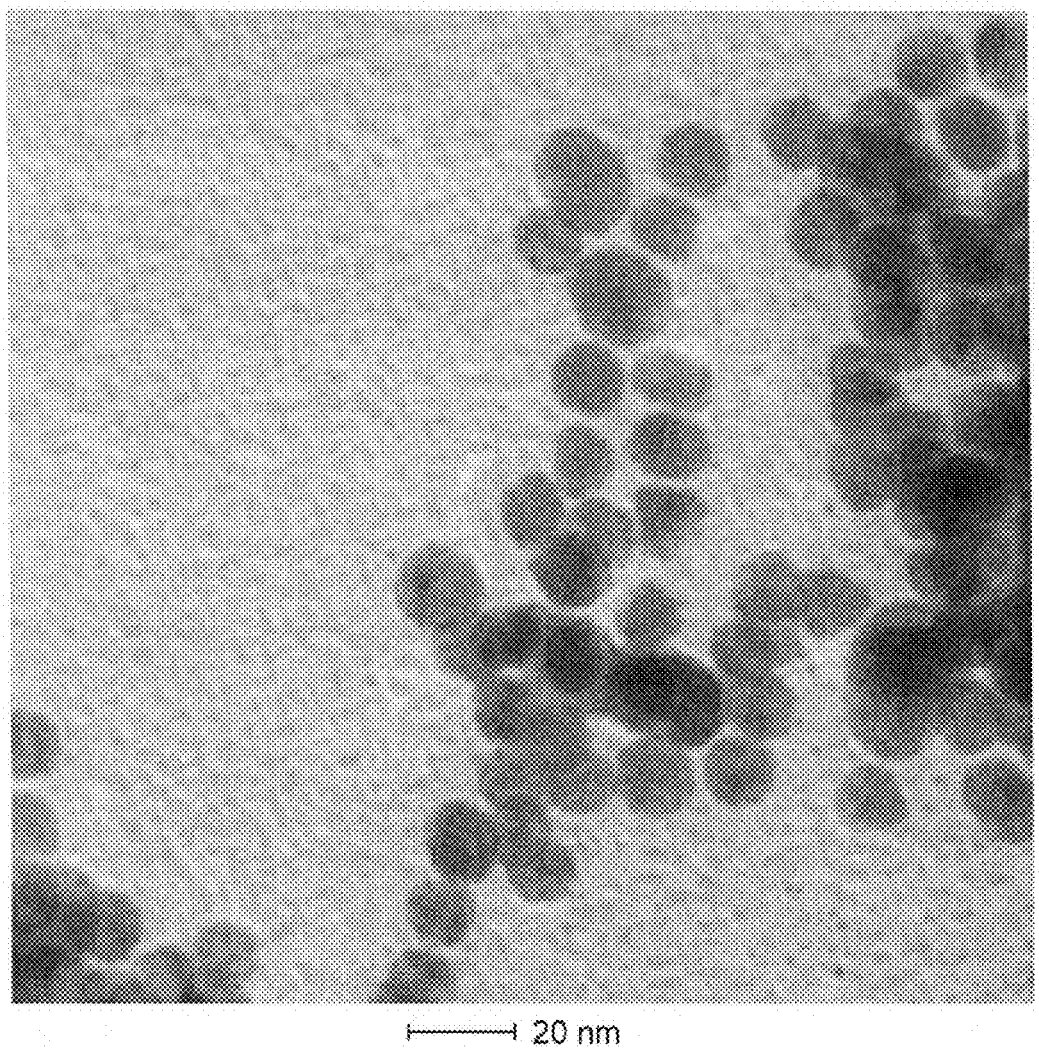
FIG. 6H is a TEM micrograph of 15-nm gold nanoparticles prepared according to one embodiment of the invention using the citrate reduction technique.

Two mL of 1% gold chloride in 90 mL DI water was heated to 80° C. for 15 minutes, then 80 mg sodium citrate in 10 ml DI water was added. The solution was boiled and vigorously stirred for 30 minutes. FIG. 6H shows pictures of ~15-nm gold nanoparticles prepared using citrate reduction.

c. Synthesis of 30-nm Gold Nanoparticles

Figure 6I:
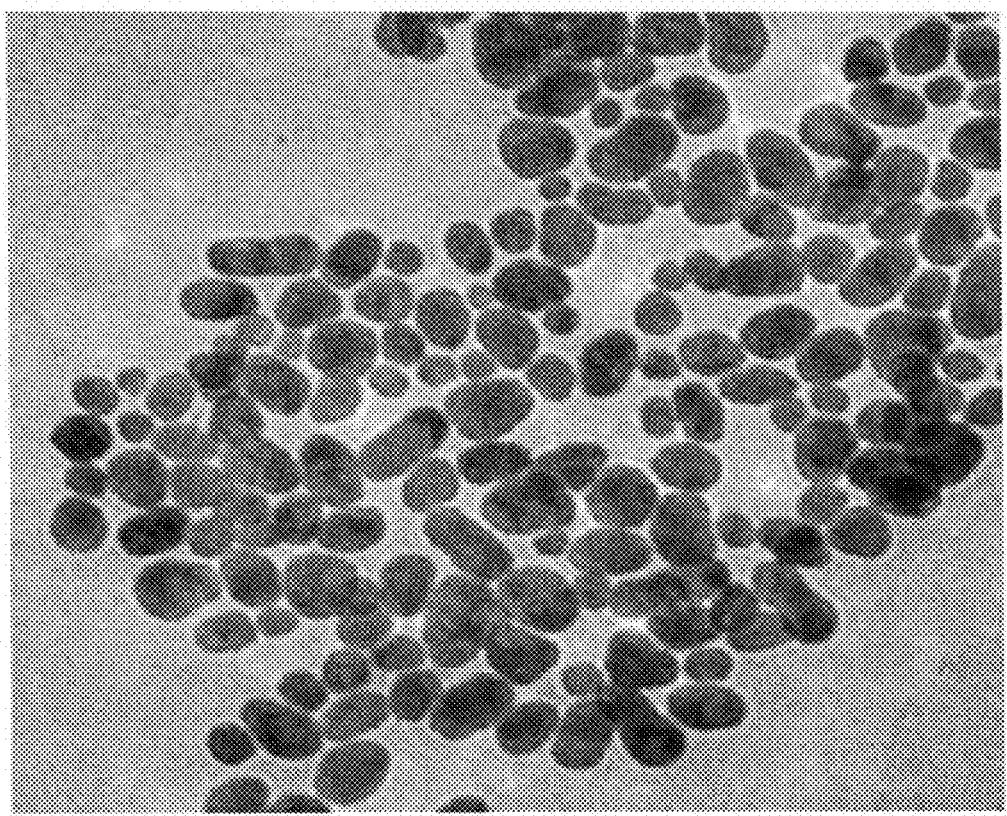
FIG. 6I is a TEM micrograph of 30-nm gold nanoparticles prepared according to one embodiment of the invention using the citrate reduction technique.

Two mL of 1% $HAuCl_4$ solution in a 100-mL round-bottom flask were mixed with 20 mg of sodium citrate, then boiled and vigorously stirred for 30 minutes. FIG. 6I shows TEM images of 30-nm gold nanoparticles prepared using the citrate reduction technique.

d. Synthesis of 60-nm Gold Nanoparticles

Figure 6J:
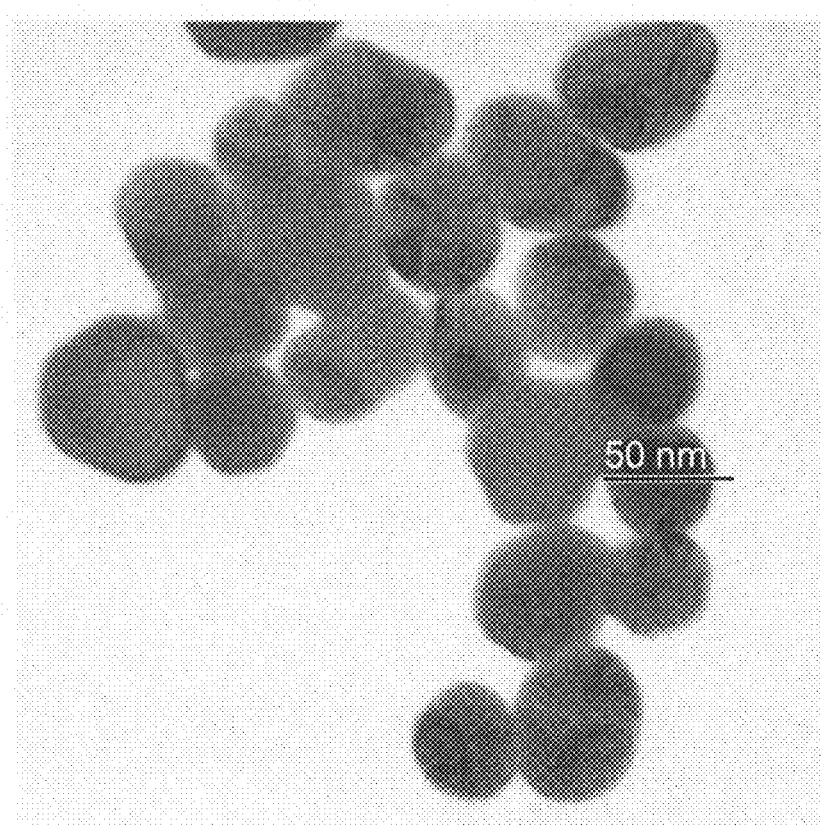
FIG. 6J is a TEM micrograph of 60-nm gold nanoparticles prepared according to one embodiment of the invention using the citrate reduction technique.
Figure 6K:
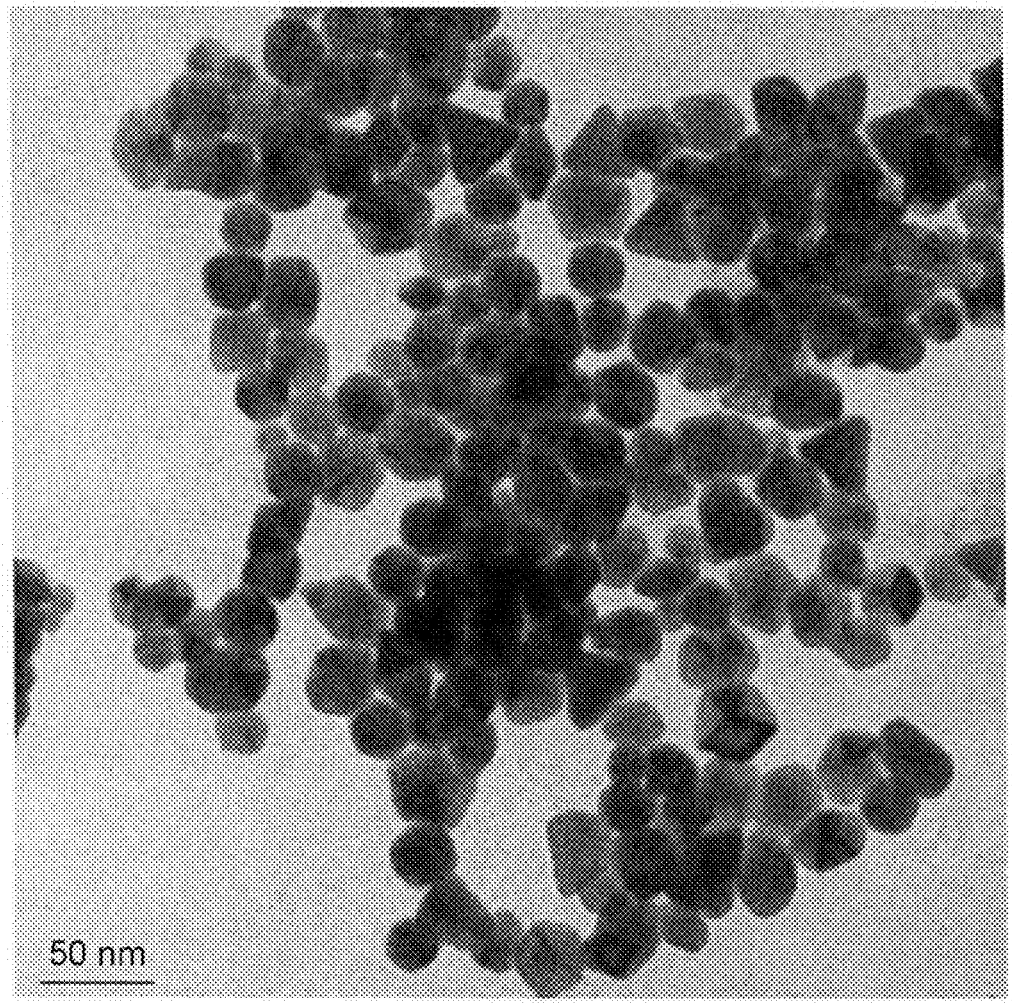
FIG. 6K is a TEM micrograph of 30-nm gold nanoparticles prepared according to one embodiment of the invention using the hydrazine monohydrate reduction technique.

Two mL of 1% $HAuCl_4$ in 100 mL of water were mixed with 10 mg of sodium citrate. The solution was boiled and vigorously stirred for 30 minutes. FIG. 6J shows TEM pictures of 60-nm gold nanoparticles prepared using the citrate reduction technique.

e. Use of Hydrazine Monohydrate as a Reducing Agent:

100 microliters (0.1 mL) of 12 millimolar gold chloride solution was diluted with 80 ml $H_2O$ in a beaker. The initial pH of the gold solution was 3.67. The temperature of the solution was increased to 80° C. for 30 minutes, at which point 0.3 mL hydrazine monohydrate was added to the gold solution. The solution pH shifted to 7.64. Over time, gold solution changed to a very light pink color. FIG. 6K shows TEM pictures of ~30-nm gold nanoparticles prepared using the hydrazine monohydrate reduction technique.

Colloidal Silver Nanoparticles

Figure 6L:
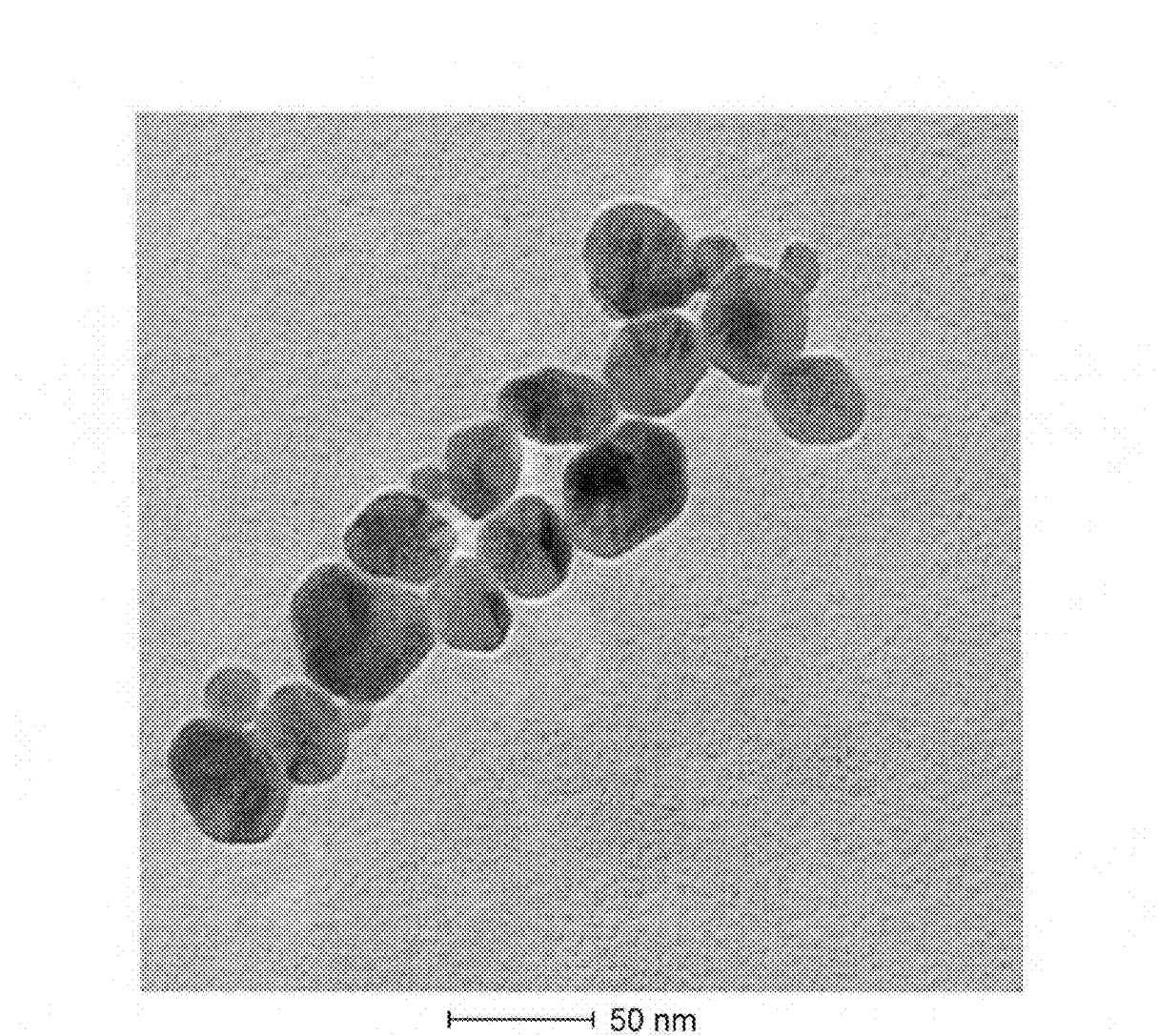
FIG. 6L is a TEM micrograph of silver nanoparticles formed by and used in the invention.

Silver nanoparticles, like the gold nanoparticles described above, can be used in the invention to enhance either the intensity of the initiation energy (i.e., the primary source: for example an IR laser for upconversion or an X-ray beam for down conversion) or to enhance the light generated from the upconverting or down-converting nanoparticles). Silver nanoparticles have been prepared from $AgNO_3$ using a variety of reducing agents. FIG. 6L shows a TEM image of silver nanoparticles prepared using the procedures described below.

Use of Sodium Citrate as a Reducing Agent:

In this method, 50 mL of a $10^{-3}$ M $AgNO_3$ aqueous solution was heated to boiling. Then, 1 mL of a 1% trisodium citrate ($C_6H_5O_7Na_3$) was added to the solution, and the solution was maintained at boiling for 1 hour before being allowed to cool. The resultant colloidal mixture exhibited a dark grey color.

Use of Hydroxylamine Hydrochloride as a Reducing Agent:

A colloidal solution was formed by dissolving 0.017 g of silver nitrate ($AgNO_3$) in 90 mL water. 21 mg of hydroxylamine hydrochloride ($NH_2OH \cdot HCl$) was dissolved in 5 mL water and 4.5 ml of 0.1 M sodium hydroxide was added. This mixture was added to the $AgNO_3$ solution. In just in a few seconds, a grey-brown solution appeared.

Use of Sodium Borohydride as a Reducing Agent:

Aqueous solutions containing 10 mL $10^{-3}$ M $AgNO_3$ and 30 mL $10^{-3}$ M $NaBH_4$ were mixed under ice-cooled conditions. The $AgNO_3$ solution was added dropwise to the $NaBH_4$ solution with vigorous stirring. The resultant mixture was allowed to age 1 hour before stirring the resultant mixture again for 10 minutes.

Metallic/Dielectric, Multi-Layer, Core-Shell Nanoparticles

As seen in FIGS. 6A-6D, the invention in various embodiments can utilize multilayer dielectric/metal structures.

Au Nanoparticles Coated with Ag or Ag Nanoparticles Coated with Au:

Core-shell nanoparticles such as gold-coated silver nanoparticles and silver-coated gold nanoparticles have been synthesized in an aqueous medium using CTAB as a surfactant and ascorbic acid as a reducing agent. Core nanoparticles (i.e. Au or Ag) were prepared using the above procedures, then coated with secondary, tertiary, etc. shells.

Figure 6M:
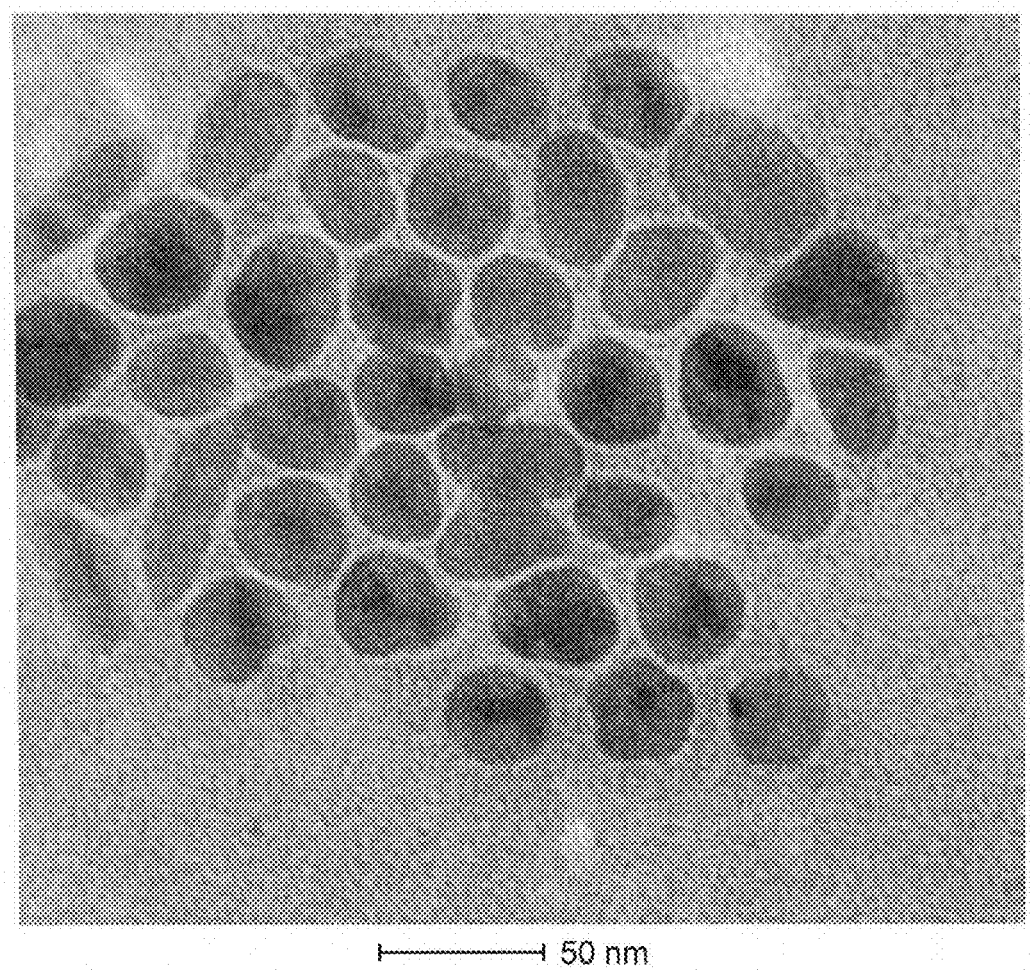
FIG. 6M is a TEM micrograph of Au coated with Ag nanoparticles formed by and used in the invention.

For example, spherical gold nanoparticles (~15 nm) were prepared by boiling $HAuCl_4$ in the presence of sodium citrate. For coating gold with a layer of silver, 1 mL of 0.1 M ascorbic acid solution, 0.5 mL of 10 mM $AgNO_3$ solution, and 0.5 mL of the previously formed Au colloid were sequentially added to 20 mL of a 50 mM CTAB solution. Subsequently, 0.1 mL of 1.0 M NaOH was added dropwise, which led to a fast color change (from red to yellow). FIG. 6M shows TEM images of Au nanoparticles coated with Ag.

A similar procedure was used to prepare Ag nanoparticles coated with Au. The use of solutions of a mixture of $AgNO_3$ and $HAuCl_4$ would yield an alloy of Ag and Au.

Au@Ag@Au@Ag Multi Shell Nanoparticles:

Multishell nanoparticles such as Au@Ag@Au@Ag were prepared using CTAB as a surfactant, and ascorbic acid and NaOH as reducing agents. Spherical gold nanoparticles (~15 nm) were prepared by boiling $HAuCl_4$ in the presence of sodium citrate. To coat gold cores with a layer of silver, 20 mL of a 50 mM CTAB, 1 mL of 0.1 M ascorbic acid, 0.5 mL of 10 mM $AgNO_3$, and 0.5 mL of the Au colloid were sequentially mixed. Subsequently, 0.1 mL of 1.0 M NaOH was added in a dropwise manner, which led to a fast color change from red to yellow.

Figure 6N:
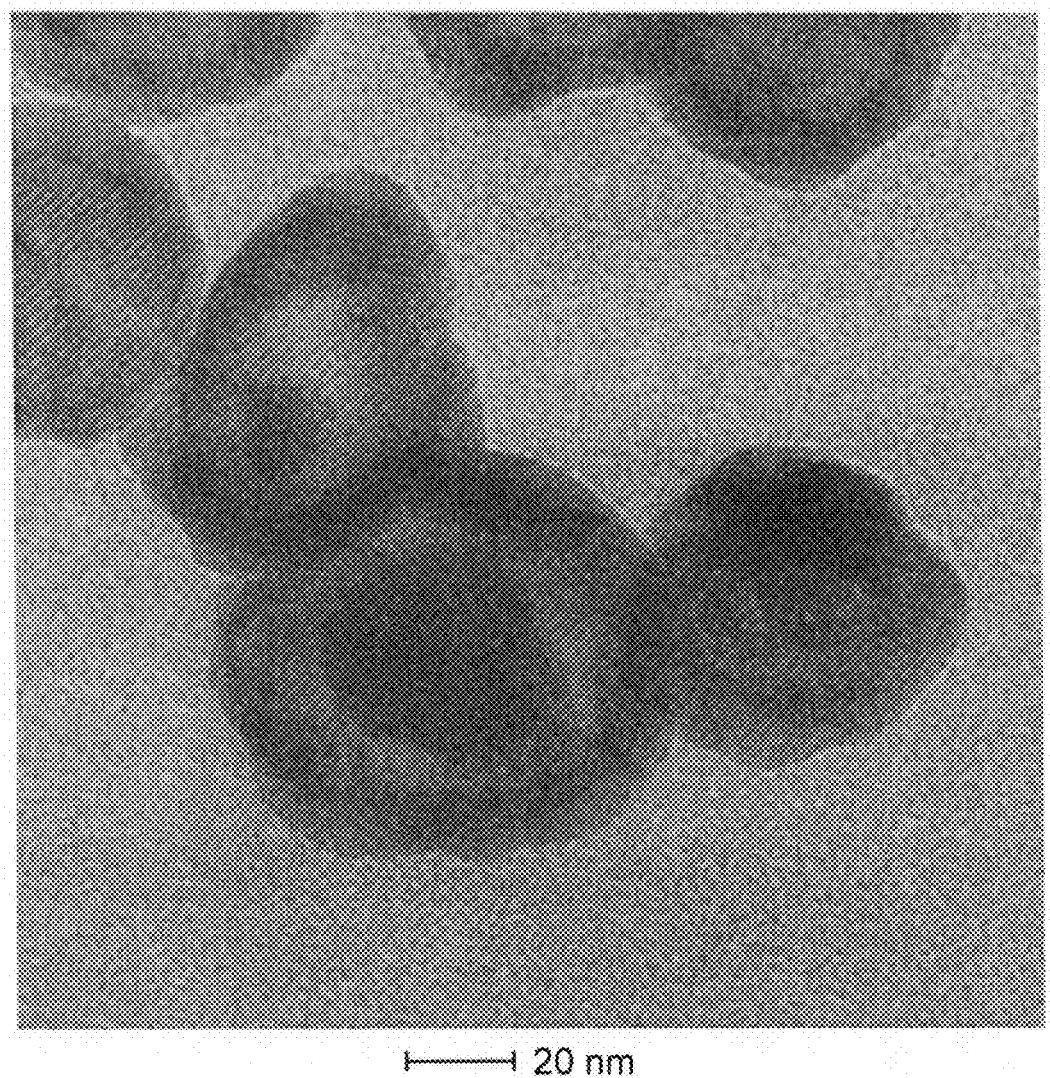
FIG. 6N is a TEM micrograph of Au/Ag/Au/Ag multi-shell nanoparticles formed by and used in the invention.

Then, another gold layer was coated by mixing 20 mL of the Ag-coated Au colloid in water with 1 mL of the ascorbic acid solution. The resulting mixture was then added to 0.05 mL of 0.10 M $HAuCl_4$ in a dropwise manner. The solution color changed to deep blue at this stage. Subsequently, an outer silver shell was formed on the previously formed Au@Ag@Au nanoparticles by mixing 20 mL of colloid with 0.5 mL 10 mM $AgNO_3$ followed by drop wise addition of 0.2 mL of 1.0 M NaOH. The solution then showed a color change to orange. FIG. 6N shows TEM images of Au@Ag@Au@Ag multi-shell nanoparticles.

All of the above core-shell nanoparticle solutions were stable in solution.

$Y_2O_3$ Coated with $SiO_2$, $Y_2O_3$ Coated with Au, $Y_2O_3$ coated with Ag or Au Coated $SiO_2$ Coreshell Nanoparticles Procedures similar to those used in the preparation of core-shell gold or silver nanoparticles can be employed to synthesize $Y_2O_3$ coated with Au or $Y_2O_3$ coated with Ag.

Metal (Au Coated with $SiO_2$) or REO Nanoparticles Coated with $SiO_2$:

$SiO_2$ can be coated on gold, silver and reactive oxide (REO) nanoparticles. There are various procedures available in the literature. See for example W. Stöber, A. Fink, E. Bohn, *J. Colloid Interface Sci.* 26 (1962) 62-69; Y. Kobayashi, H. Katakami, E. Mine, D. Nagao, M. Konno, L. M Liz-Marzán, *Journal of Colloid and Interface Science* 283 (2005) 392-396; L. M. Liz-Marzan, M. Giersig and P. Mulvaney, *Langmuir* 1996, 12, 4329-4335; S. P. Mulvaney, M. D. Musick, C. D. Kearting, M. J. Natan, *Langmuir* 2003, 19, 4784-4790; Q. Lu, A. Li, F. YunGuo, L. Sun and L. C. Zhao, *Nanotechnology* 19 (2008) 205704; Jana, et. al., *Chem. Mater., Vol.* 19, p. 5074-5082 (2007), the entire contents of each of these references are incorporated herein by reference. In this silica-coating method, which involves condensation of alkoxysilanes on the nanoparticle surface, various types of functional silanes which have alcoxysilyl groups (e.g., methoxysilyl, ethoxysilyl, isopropoxysilyl, etc.) at one end and an amino or thiol group at the other end are typically used. It has been shown that alcoxysilyl groups undergo hydrolysis in a basic or acidic medium to form a silica shell.

The invention employs two different strategies to induce silica polymerization on the nanoparticle surface. In the case of REO nanoparticles, the silanization process involves condensation of silanes with the hydroxyl groups on the REO particle surface. For Au and Ag, mercapto or amino silane can be used as a linker. In this case, the thiol group of this linker silane chemisorbs onto the metal nanoparticle surface, and the alcoxysilane groups initiate silica shell formation on the nanoparticle surface.

Optimization of the silanization conditions has been performed in order to fabricate water-soluble nanoparticles. There are in general two primary steps in the silane conjugation scheme. First, it is important that excess ligands be removed from the starting nanoparticles. Second, temperature, heating time, and pH all play critical roles in the rate of silane hydrolysis. Both alkyl amines and aminosilane, for example, can serve as a base for the catalytic hydrolysis of alkoxysilane at 65-70° C. In some procedures, nanoparticle-silane conjugates begin to precipitate within 3-5 min of reaction, and finish within 15-30 min. If a specific shell thickness is desired, the hydrolysis can be stopped at any time by quenching the reaction to room temperature or by separating the precipitate from the solution. This is useful because further heating of the precipitated nanoparticle-silane conjugates without separating them from free silanes can produce interparticle cross-linking via hydrolysis. If excess precursor is removed, intra-particle crosslinking can proceed without the potential of interparticle cross-linking.

Chemical Synthesis of Multi-Layer Core-Shell Structures Using $Y_2O_3$:

To deposit multiple shells on $Y_2O_3$ nanoparticles, $Y_2O_3$ nanoparticles were initially coated with Ag via UV photoreduction in a procedure similar to that discussed above for gold shells. In the invention, a number of approaches can be utilized for the addition of a gold shell. These include 1) a sodium citrate process, 2) a sodium borohydride reduction, 3) a hydrazine monohydrate reduction, 4) a solution containing hydroxylamine and NaOH, and 5) a mixture of CTAB, ascorbic acid, and NaOH.

Use of Sodium citrate as a Reducing Agent:

A typical experiment used 0.1 to 1 mL of $Y_2O_3$ coated with Ag (~50 nm), 1 to 3 mL of $2.5 \times 10^{-3}$ M $HAuCl_4$, and 50 mL distilled water in a 100 ml round bottom flask. This solution was boiled with constant stirring, and 3 mL of 1 wt % sodium citrate was added. The resultant colloidal solution color became black with a pH of approximately pH 6.5. The solution was stirred for another 15 min and then allowed to stand.

Use of Sodium Borohydride as Reducing Agent:

A typical experiment used 0.1 to 1 mL of $Y_2O_3$ coated with Ag (~50 nm), 1 to 3 mL of $2.5 \times 10^{-3}$ M $HAuCl_4$, and 50 mL distilled water in a 100 mL round bottom flask. Under constant stirring this solution was boiled prior to addition of 0.1 to 1 mL of 0.1 M $NaBH_4$ solution. The resultant colloidal solution became black and aggregated within a few minutes.

These fabrication procedures provide the invention with a number of nanoparticle systems for application to a variety of media or materials where the nanoparticles can directly or indirectly generate light from an initiation energy or enhance the generated light or the radiation initiation energy.

In a further embodiment of the invention, the upconverter structures of the invention can be incorporated into a material (e.g., biocompatible polymer) that can form a nanocap onto the metal (gold) nanoparticles. The material can be a gel or biocompatible polymer that can have long-term continuous release properties. Suitable gel or biocompatible polymers include, but are not limited to poly(esters) based on polylactide (PLA), polyglycolide (PGA), polycarpolactone (PCL), and their copolymers, as well as poly(hydroxyalkanoate)s of the PHB-PHV class, additional poly(ester)s, natural polymers, particularly, modified poly(saccharide)s, e.g., starch, cellulose, and chitosan, polyethylene oxides, poly(ether)(ester) block copolymers, and ethylene vinyl acetate copolymers.

In a further embodiment, the metallic nanoparticles without a dielectric core can be provided in the medium along with the upconverting metal-covered dielectric core nanoparticles so that the "pure" metallic nanoparticles can enhance interaction of the upconverted light with another agent or recipient in the medium (such as for example a photosensitizer, a photoactivatable drug, or a photoinitiator).

Figure 7A:
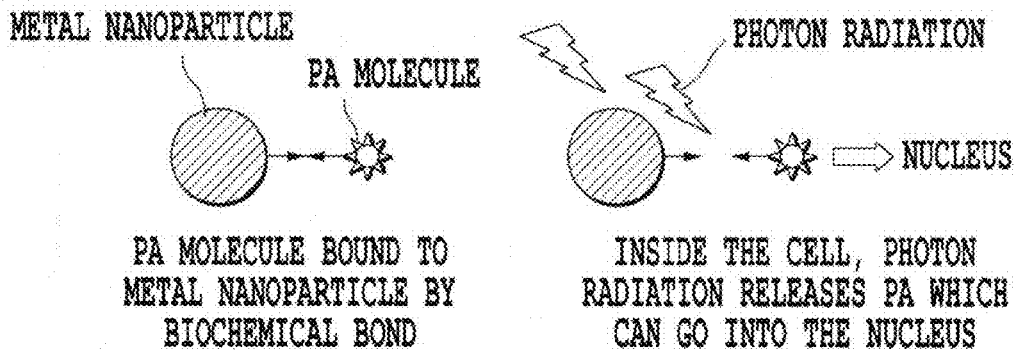
FIGS. 7A-7C are schematic illustrations of other various upconverter structures of the invention where a recipient molecule is bound to the metal nanoparticles via a linker that can be dissociated by a photon radiation.
Figure 7B:
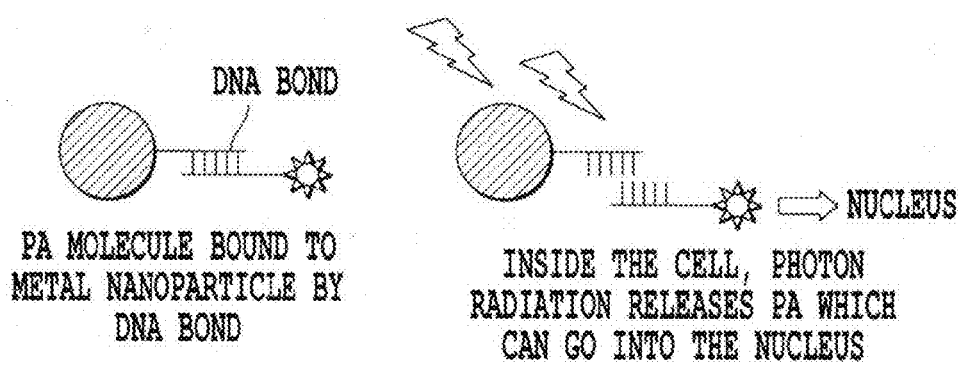
Figure 7C:
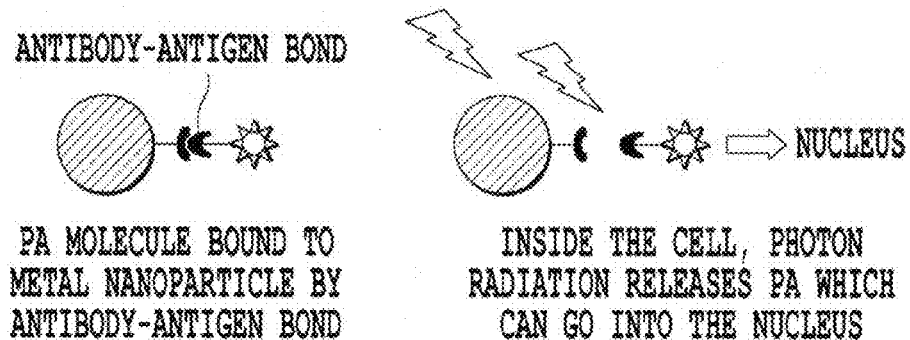

FIG. 7 shows other possible embodiments where a recipient molecule is bound to the metal nanoparticles via a linker that can be cut by photon radiation. Such a linker includes, but is not limited to, a biochemical bond, a DNA bond, an antibody-antigen bond, or other bond which, when excited by light, reorganizes its bonding electrons to non- or anti-bonding state. In another embodiment, the linker is a chemically labile bond that will be broken by the chemical environment inside the cell. In various embodiments, it may be more difficult for metal nanoparticles to enter targeted sites in the medium than for smaller molecules.

Aggregation of metal (such as silver or gold) nanoparticles (nanospheres, nanorods, etc) is often a problem, especially with citrate-capped gold nanospheres, cetyl trimethylammonium bromide (CTAB)-capped gold nanospheres, nanorods, and nanoshells because they have poor stability when they are dispersed in buffer solution due to the aggregating effect of salt ions. The biocompatibility can be improved and nanoparticle aggregation prevented by capping the nanoparticles with polyethylene glycol (PEG) (by conjugation of thiol-functionalized PEG with metal nanoparticles).

The majority of immobilization schemes involving metal surfaces, such as gold or silver, utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface, with lengths of the alkyl group from 4 to 20 carbons being preferred.

There are many methods related to the preparation of stable oligonucleotide conjugates with gold particles by using thiol-functionalized biomolecules that have previously been shown to form strong gold-thiol bonds. These methods described below can be used in various embodiments of the invention. Oligonucleotides with 5'-terminal alkanethiol functional groups as anchors can be bound to the surface of gold nanoparticles, and the resulting labels were robust and stable to both high and low temperature conditions [R. Elghanian, J. J. Storhoff R. C. Mucic, R. L. Letsinger and C. A. Mirkin, *Selective colorimetric detection of polynucleotides based on the distance-dependent optical properties of gold nanoparticles. Science* 277 (1997), pp. 1078-1081], the entire contents of which are incorporated herein by reference. A cyclic dithiane-epiandrosterone disulfide linker has been developed for binding oligonucleotides to gold surfaces. Id. Li et al. have reported a trithiol-capped oligonucleotide that can stabilize gold metal nanoparticles having diameters=100 nm, while retaining hybridization properties that are comparable to acyclic or dithiol-oligonucleotide modified particles [Z. Li, R. C. Jin, C. A. Mirkin and R. L. Letsinger, *Multiple thiol-anchor capped DNA-gold nanoparticle conjugates. Nucleic Acids Res.* 30 (2002), pp. 1558-1562], the entire contents of which are incorporated herein by reference.

In general, silver nanoparticles can not be effectively passivated (i.e., made less reactive) by alkylthiol-modified oligonucleotides using the established experimental protocols that were developed for gold particles. One method of generating core-shell particles having a core of silver and a thin shell of gold has allowed silver nanoparticles to be readily functionalized with alkylthiol-oligonucleotides to prepare pure gold particle-oligonucleotide conjugates, suitable in various embodiments of the invention. [Y. W. Cao, R. Jin and C. A. Mirkin, *DNA-modified core-shell Ag/Au nanoparticles. J. Am. Chem. Soc.* 123 (2001), pp. 7961-7962], the entire contents of which are incorporated herein by reference.

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold. See Burges, J. D.; Hawkridge, F. M. in Langmuir 1997, 13, 3781-6, the entire contents of which are incorporated herein by reference. After self-assembled monolayer (SAM) formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds.

Such bonding schemes have applications not only by providing a mechanism by which the nanoparticles can be controllably dispersed and delivered within a medium, but may also play a role in the formation of encapsulated upconverter structures of the invention.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively. Especially for gold nanoparticles, the NIR region is very appropriate for the delivery of energy into a medium where otherwise optical scatter at shorter wavelengths would present a problem, such as for example in the treatment of waste water or the sterilization of food products having high concentrations of suspended solids or the delivery of photoactivatible drugs into a living cell.

The invention includes several methods for using light to excite photoactivate or photostimulate compounds in the medium. Light having wavelengths within the so-called "window" (designed to penetrate any container holding the medium to be processed and/or to transmit through the medium) can be used. Moreover, while certain aspects of the invention prefer that the excitation light be nominally non-absorbing (or nearly transparent) in the medium, due to the plasmonic advantages, the invention is still useful in mediums even when there is considerable scatter and absorption.

The ability of light to penetrate the medium depends on absorption and scatter. Within the hydrous medium, a window extends from 600 to 1300 nm, from the orange/red region of the visible spectrum into the NIR. See T. Vo-Dinh, Biomedical Photonics Handbook, CRC, 2003. At the short-wavelength end, absorbing biomolecules become important, including DNA and the amino acids tryptophan and tyrosine. At the infrared (IR) end of the window, penetration is limited by the absorption properties of water (water vibrational overtone absorptions start to become important at 950 nm). Within the window, scattering is dominant over absorption, and so the propagating light becomes diffuse, although not necessarily entering into the diffusion limit.

In various embodiments of the invention, the upconverter structures are covered with a layer (1-30 nm) of dielectric material (e.g. silica or polymer). The dielectric layer (or nanoshell) is designed to prevent quenching of the luminescence light emitted from a dielectric core (e.g., a La doped-dielectric core). Quenching can sometimes occur due to direct contact of a metal to the receptor or media. To address this issue, recipient molecules are bound to (or in proximity of) the metal shell via a spacer (linker). The spacer is designed to prevent quenching of the luminescence light emitted by the dielectric core.

FIG. 8A shows an embodiment of the invention where the dielectric core has appended thereon or attached by linkages a recipient molecule such as a photo-active molecule. An appended molecule is one that is typically directly bonded either by a covalent bond or a dative association. Linkers are typically added to covalently tether the molecule to the nanocrystal. In various embodiments of the invention, either mechanism can be used to secure the recipient molecule. The photo-active molecule 6 is receptive to interaction with the generated light $\lambda_2$ such that upon interaction with the light $\lambda_2$ chemical reactions or pharmaceutical reactions are induced therein or there from. For example, UV light generated from the upconverter structures can either change the state of the photo-active molecule to a reactive state, or can sever the linkages releasing the recipient molecule 6 into the medium. As shown in FIG. 8A, in one embodiment of the invention, the upconverter material is itself separated from a metal component. The exact distances between the recipient molecule and the dielectric core can be varied by using certain chemical linking compounds and as explained below that may also provide certain steric or synergistic effects.

As shown in FIG. 8A, in one embodiment of the invention, the recipient molecule can be a bioreceptor. Bioreceptors are the key to specificity for targeting disease cells or mutate genes or specific biomarkers. They are responsible for binding the biotarget of interest to the drug system for therapy. Bioreceptors can take many forms and the different bioreceptors that have been used are as numerous as the different analytes that have been monitored using biosensors. However, bioreceptors can generally be classified into five different major categories. These categories include: 1) antibody/antigen, 2) enzymes, 3) nucleic acids/DNA, 4) cellular structures/cells and 5) biomimetic. FIG. 8A illustrates various upconversion structures with bioreceptors that can be designed. The probes are similar to those previously described but also have a bioreceptor for tumor targeting. Accordingly, in one embodiment of the invention, the upconversion structures include (a) photoactive (PA) molecules bound to a metal nanoparticle having a bioreceptor, (b) PA-linked UC material nanoparticle covered with metal nanoparticles, having a bioreceptor, (c) a metal nanoparticle covered with an UC material nanocap with linked PA molecule, having a bioreceptor, (d) an UC material nanoparticle covered with metal nanocap and linked PA, having a bioreceptor, (e) a metal nanoparticle covered with an UC material nanoshell with PA, having a bioreceptor, (f) an UC material nanoparticle covered with metal nanoshells, having a bioreceptor, (g) an UC material nanoparticle covered with a metal nanoshell with a protective coating layer, having bioreceptor.

FIG. 8B shows yet other embodiments of plasmonics-active nanostructures having upconverting material (UC) with linked photo-active (PA) molecules and also having a bioreceptor. Accordingly, in one embodiment of the invention, the upconversion structures include (a) PA molecules bound to UC material and to a plasmonic metal nanoparticle, (b) a plasmonic metal nanoparticle with an UC material nanocap covered with PA molecules, (c) a PA-covered UC material nanoparticle with plasmonic metal nanoparticles, (d) an UC material-containing nanoparticle covered with PA molecules and a plasmonic metal nanocap, (e) a plasmonic metal nanoparticle core with an UC material nanoshell covered with PA molecule, and (f) a PA molecule bound to UC material (attached to a plasmonics metal nanoparticle) by detachable biochemical bond.

In the embodiment in FIGS. 8A and 8B, the bioreceptors can be antibody probes, DNA probes, and/or enzyme probes.

For antibody probes, antibody based targeting is more active, specific and efficient. The antibodies are selected to target a specific tumor marker (e.g., anti-epidermal growth factor receptor (EGFR) antibodies targeted against over expressed EGFR on oral and cervical cancer cells; anti-Her2 antibodies against over expressed Her2 on breast cancer cells) Antibodies are biological molecules that exhibit very specific binding capabilities for specific structures. An antibody is a complex biomolecule, made up of hundreds of individual amino acids arranged in a highly ordered sequence. For an immune response to be produced against a particular molecule, a certain molecular size and complexity are necessary: proteins with molecular weights greater then 5000 Da are generally immunogenic. The way in which an antigen and its antigen-specific antibody interact may be understood as analogous to a lock and key fit, by which specific geometrical configurations of a unique key permits it to open a lock. In the same way, an antigen-specific antibody "fits" its unique antigen in a highly specific manner. This unique property of antibodies is the key to their usefulness in immunosensors where only the specific analyte of interest, the antigen, fits into the antibody binding site.

For DNA probes, the operation of gene probes is based on hybridization processes Hybridization involves the joining of a single strand of nucleic acid with a complementary probe sequence. Hybridization of a nucleic acid probe to DNA biotargets (e.g., gene sequences of a mutation, etc) offers an accurate measure for identifying DNA sequences complementary to that of the probe. Nucleic acids strands tend to be paired to their complements in the corresponding double-stranded structure. Therefore, a single-stranded DNA molecule will seek out its complement in a complex mixture of DNA containing large numbers of other nucleic acid molecules. Hence, nucleic acid probe (i.e., gene probe) detection methods are very specific to DNA sequences. Factors affecting the hybridization or reassociation of two complementary DNA strands include temperature, contact time, salt concentration, and the degree of mismatch between the base pairs, and the length and concentration of the target and probe sequences.

Biologically active DNA probes can be directly or indirectly immobilized onto a drug system, such as the EEC system (e.g., gold nanoparticle, a semiconductor, quantum dot, a glass/quartz nanoparticles, etc.), surface to ensure optimal contact and maximum binding. When immobilized onto gold nanoparticles, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. In one embodiment, silanization methods are used for binding to glass surfaces using 3 glycidoxypropylt-rimethoxysilane (GOP) or aminopropyltrimethoxysilane (APTS) and may be used to covalently link DNA via amino linkers incorporated either at the 3' or 5' end of the molecule during DNA synthesis.

For enzyme probes, enzymes are often chosen as bioreceptors based on their specific binding capabilities as well as their catalytic activity. In biocatalytic recognition mechanisms, the detection is amplified by a reaction catalyzed by macromolecules called biocatalysts. With the exception of a small group of catalytic ribonucleic acid molecules, all enzymes are proteins. Some enzymes require no chemical groups other than their amino acid residues for activity. Others require an additional chemical component called a cofactor, which may be either one or more inorganic ions, such as $Fe^{2+}$, $Mg^{2+}$, $Mn^{2+}$, or $Zn^{2+}$, or a more complex organic or metalloorganic molecule called a coenzyme. The catalytic activity provided by enzymes allows for much lower limits of detection than would be obtained with common binding techniques. The catalytic activity of enzymes depends upon the integrity of their native protein conformation. If an enzyme is denatured, dissociated into its subunits, or broken down into its component amino acids, its catalytic activity is destroyed. Enzyme-coupled receptors can also be used to modify the recognition mechanisms.

The novel materials and upconverter structures of the invention include in various embodiments nanoparticles of neodymium and ytterbium doped yttrium oxide, europium and ytterbium doped yttrium oxide, and any combination of rare earth trivalent ions doped into a neodymium oxide nanocrystal. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are a number of advantages offered by these yttrium oxide nanostructures of the invention. The small scale synthetic methodology for creating nanoscale yttrium oxide is easier to control and produce in yttrium oxide than in YAG. The host structure of yttrium oxide scintillates (by down conversion) at a valuable emission wavelength to excite known pharmaceutical materials as the recipients. Finally, these combinations of dopants in yttrium oxide provide new emission colors for the yttrium oxide nanocrystal in an imaging format.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the ultraviolet, visible, and NIR spectral regions.

Neodymium oxide is a dielectric nanostructural material that can also be synthesized by the same polyalcohol method described above with regard to yttrium oxide nanocrystal preparation. Doped neodymium oxide is expected to also show upconversion processes. Neodymium oxide as a host structure possesses lower optical phonon modes than all other oxide based materials. Lower frequency of phonon may be best suited for electronic transfer between ions. In general, phonon modes are vibrations in a crystal lattice whose frequencies are dependent on the crystal lattice structure and materials. Energy released by upconversion (effectively atomic emission) is transmitted through the photons. With photons, energy can be transferred via Forster, Dexter, or photon capture pathways. Meanwhile, for holes and electrons, charge tunneling is one mechanism for energy transfer. For photons, lower phonon modes typically exhibit less destructive interference, thereby being more suitable for upconverted emission. Accordingly, in one embodiment of the invention, the lower energy phonon modes for neodymium oxide are expected to provide for a stronger electron phonon coupling transfer to occur between the dopants inside of the neodymium oxide. Neodymium oxide has also shown the same low toxic effects as yttrium oxide and therefore is suitable for insertion in living biological tissue.

Accordingly, the novel upconversion emitters of this invention involve a number of configurable structures and materials which will permit their use in a variety of applications. Further, many of the dielectric cores described in the invention exhibit down conversion properties. The invention in several applications described below utilizes both the upconversion and down conversion properties of a particular nanoparticle material system. In some of the applications described below, particles designed for down conversion can be used in conjunction with separate particles designed for upconversion.

In some embodiments of the invention, down converting materials (such as those described herein) are used separately without the need to include up converting materials.

Accordingly, the invention in various embodiments can use a wide variety of down conversion materials. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties.

Further, the down conversion materials for the invention described here can be coated with insulator materials such as for example silica which will reduce the likelihood of any chemical interaction between the luminescent particles and the medium. For biological applications of inorganic nanoparticles, one of the major limiting factors is their toxicity. Generally speaking, all semiconductor nanoparticles are more or less toxic. For biomedical applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, $ZnS:Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

Alkali lead silicate Glass compositions were also useful for down-converting x-rays into UV and visible. These glass compositions contain $SiO_2$, $B_2O_3$, $Na_2O$, $K_2O$ and PbO. The range of compositions include in mole %: $SiO_2$ from 44% to 73%, $B_2O_3$ from 0% to 3%, $Na_2O$ from 0.5% to 4%, $K_2O$ from 0.5% to 11% and PbO from 5% to 55%. A whole range of compositions are possible. Furthermore, other materials can be included to promote fluorescence including for example MgO and Ag.

In various embodiments of the invention, the following luminescent polymers are also suitable as conversion materials: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

Figure 8C:
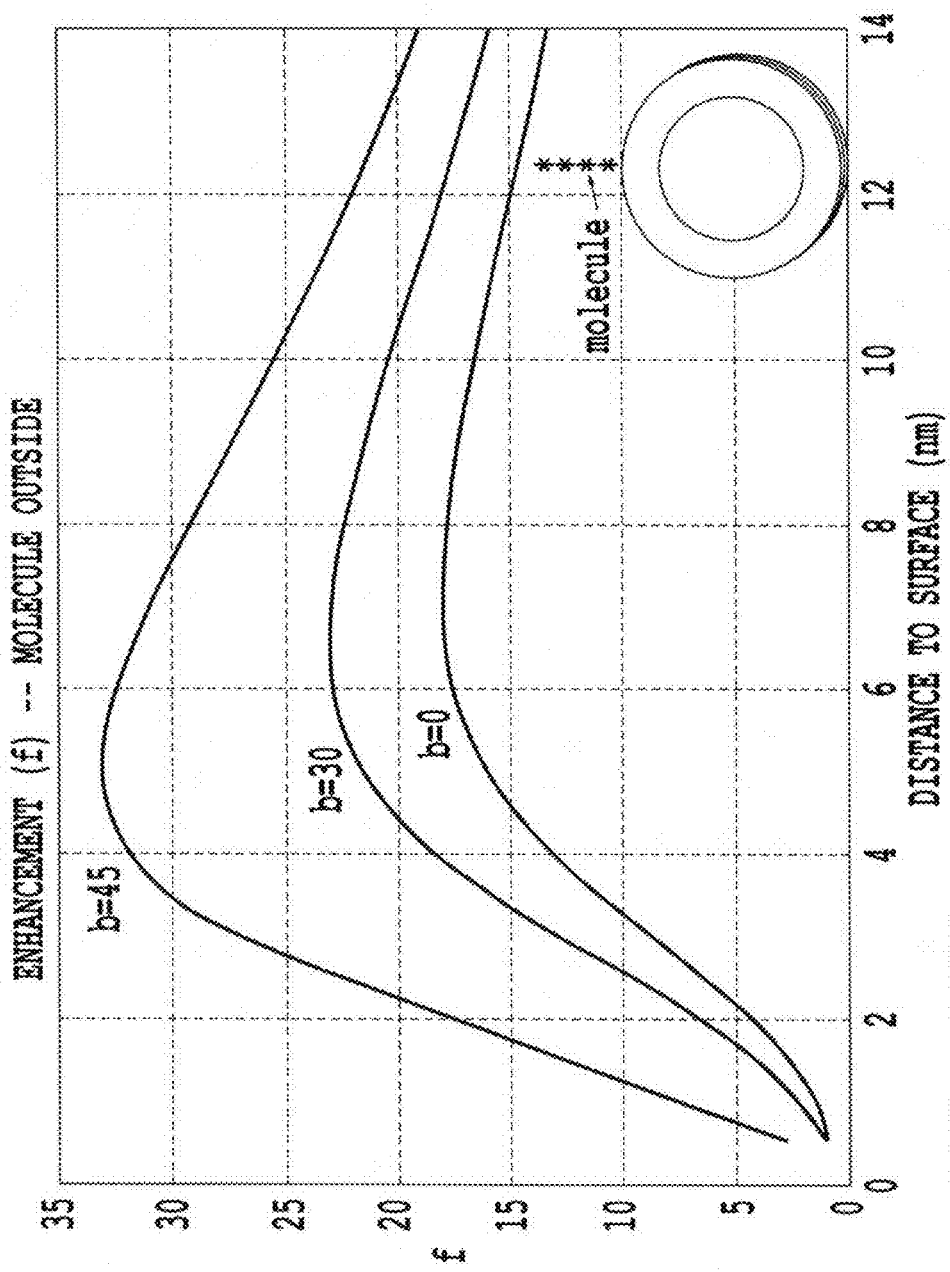
FIG. 8C is a depiction of the enhancement of emission as a function of wavelength for a configuration similar to that in FIG. 8B (F)

In the embodiment shown in FIG. 8B (F), the up converting agent is displaced from the plasmonics metal. In one embodiment, the displacement distance effects (and in certain situations enhances) the interaction of the incident radiation with the up converting material. FIG. 8C shows an example of the enhancement (f) of emission as a function of wavelength for a configuration similar to that in FIG. 8B (F) where the energy converting molecule is displaced from the metal shell, and where the outer radius of the metal shell is set arbitrarily to 50 nm and b is the value of the inner radius of the shell in units of nanometers.

Figure 8D:
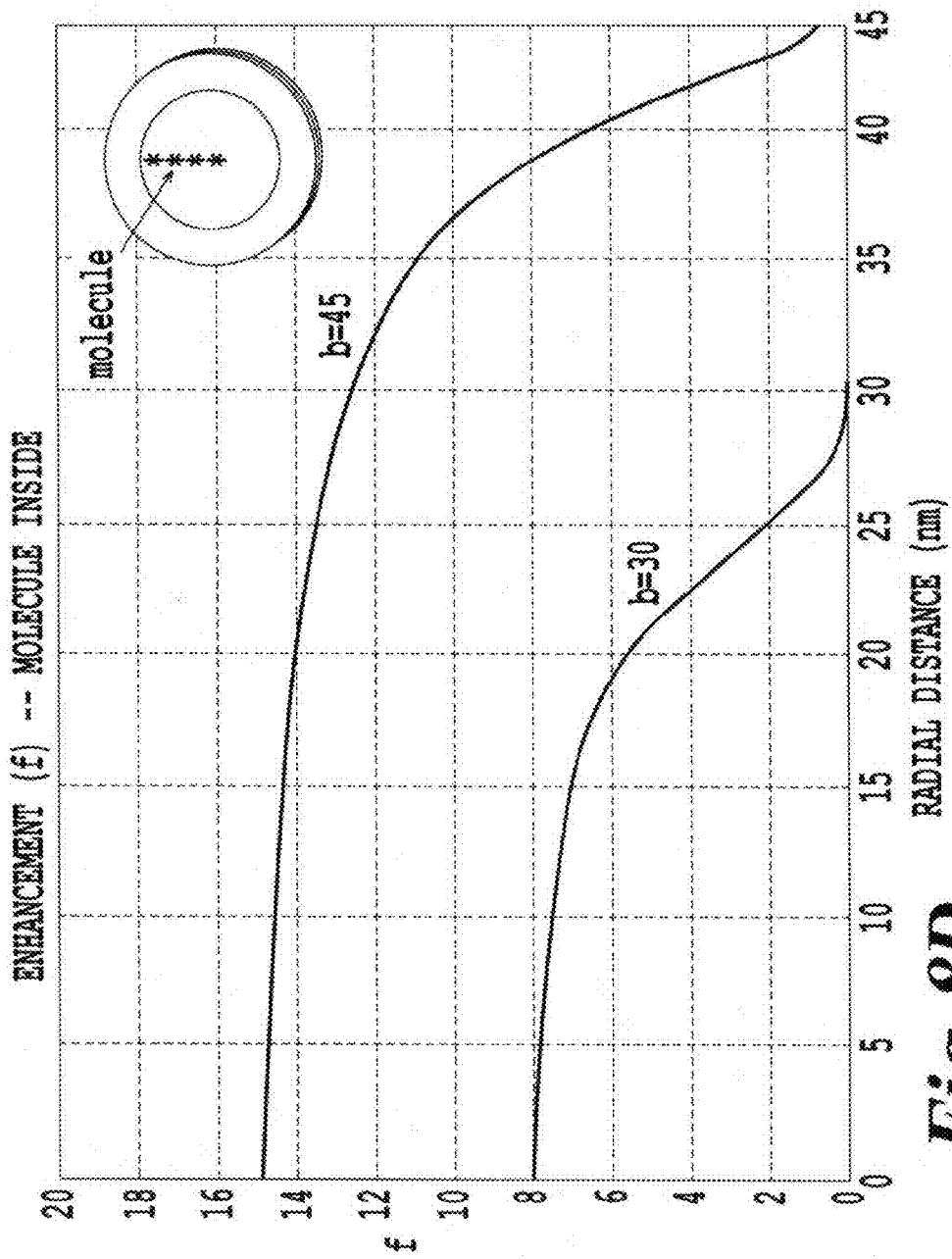
FIG. 8D is a depiction of the enhancement of emission as a function of wavelength for a configuration where the molecule is located inside a metallic shell.

In concept, the same effect occurs if the molecule were located at different positions inside a metallic shell. The enhancement results are shown in FIG. 8D, where the outer radius of the metal shell is set arbitrarily to 50 nm and b is the value of the inner radius of the shell in units of nanometers.

Figure 8E:
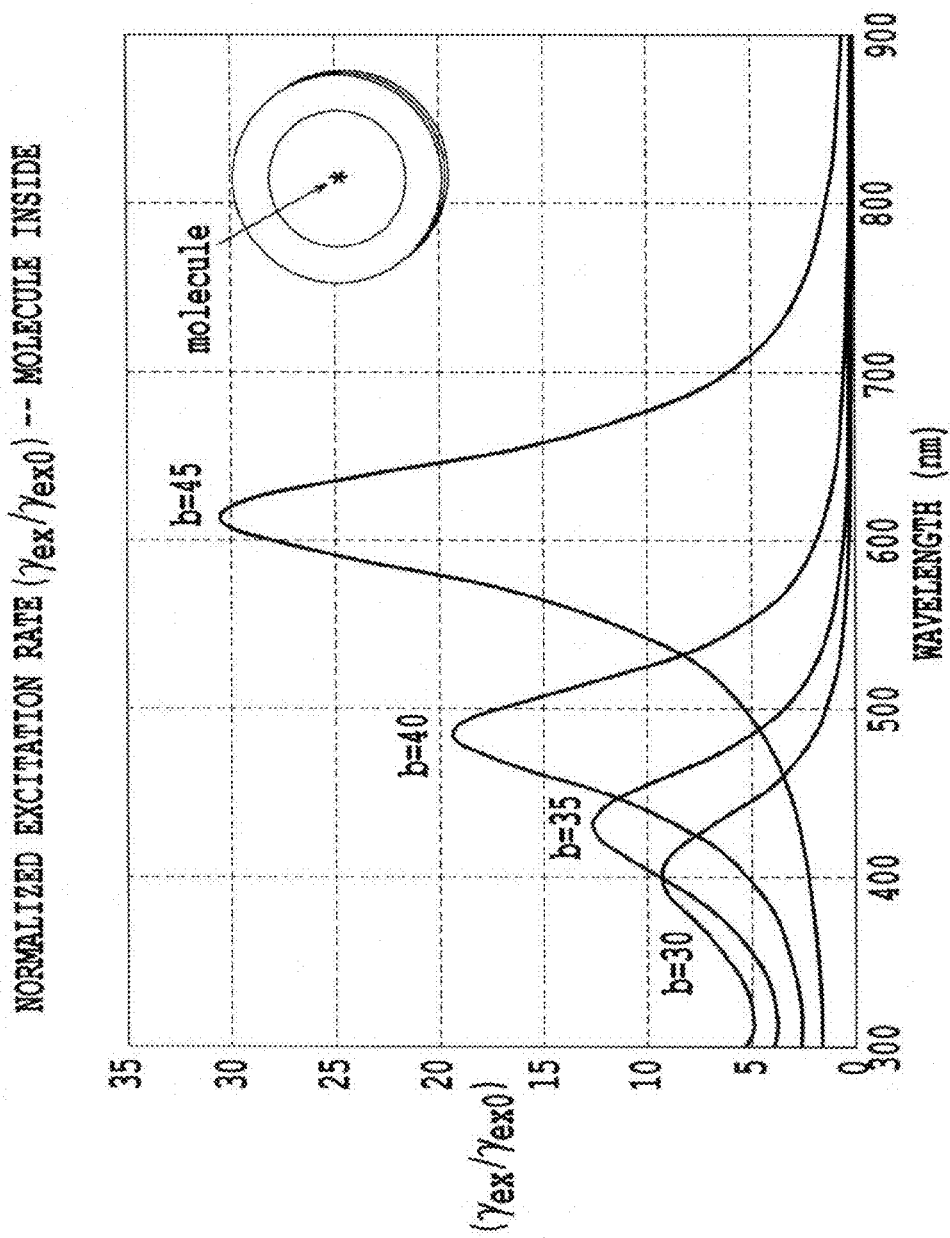
FIG. 8E is a depiction of the excitation enhancement as a function of wavelength for a configuration similar to that in FIG. 8A (F)

As shown in FIG. 8A (F), the up converting agent can be disposed inside a plasmonics metal shell. The maximum enhancement effect will generally occur near a plasmon resonance of the metallic shell, and therefore the enhancement will generally have a strong dependence on wavelength. FIG. 8E shows an example of the dependence of excitation enhancement on wavelength for a configuration similar to that in FIG. 8A (F) where the energy converting material is covered with a plasmonics layer, where the outer radius of the shell is set arbitrarily to 50 and b is the value of the inner radius of the shell in units of nanometers.

Figure 8F:
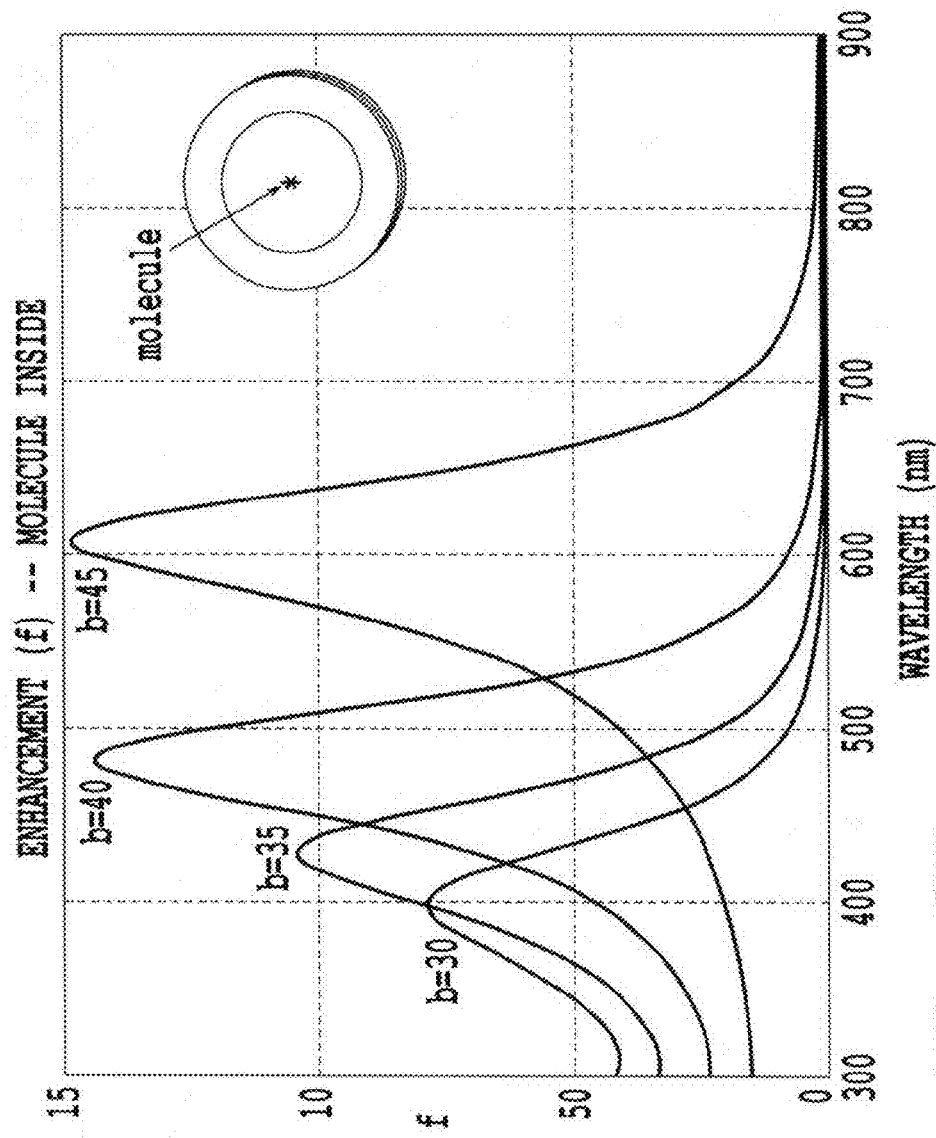
FIG. 8F is a depiction of the dependence of emission enhancement on wavelength for the structure and excitation shown in FIG. 8E.

Once the up converting or down converting molecule is excited by the incident radiation field, its energy is released by emission such as for example fluorescence or phosphorescence. If for the purpose of illustrating this embodiment of the invention, one assumes an intrinsic quantum efficiency of the molecule equal to one, the molecule, in the absence of the shell, will radiate away all its energy due to the exciting field. In the presence of the shell, some of the radiative power will be absorbed the shell. FIG. 8F shows the dependence of the radiation (i.e., emission) on wavelength for the structure and excitation shown in FIG. 8E.

Figure 8G:
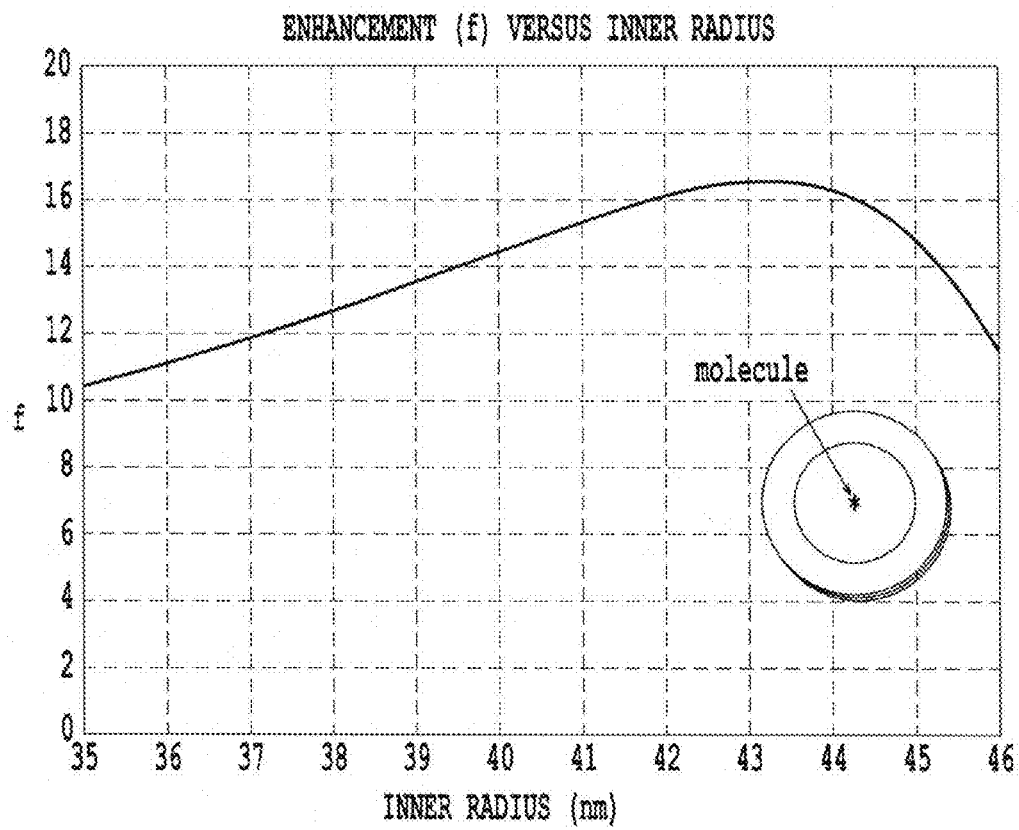
FIG. 8G is a depiction of the data of FIG. 8F simplified to show the total enhancement verses the inside diameter of the metal shell.

FIG. 8G shows the data of FIG. 8F simplified to show the total enhancement verses the inside diameter of the metal shell.

From the results discussed above, when the molecule is outside the shell, the local field is the incident radiation field plus the field scattered from the shell. When the molecule resides within the shell core, the local field is the radiation field that penetrates the shell. Both the excitation of the molecule and its radiative emission are strongly influenced by plasmon resonances excited within the shell. In one embodiment of the invention, the enhancement for an external molecule is larger for a shell than for a solid sphere of the same diameter.

Both the excitation and the quantum efficiency are larger for a shell than for a solid sphere, although both of these quantities appear to peak at different shell thicknesses. In one embodiment of the invention, the overall enhancement can range as high as 30 for a molecule outside the shell and about 15 for a molecule inside the shell core. In the latter case, however, the enhancement is inhibited by a thick shell and achieves a peak value for a relatively thin shell. Two factors affect the drop off in the enhancement as the shell becomes increasingly thin. The first is the weakening of the plasmon resonance as the volume of metal is reduced and the second is the further damping of the resonance due to electron scattering within a thin shell.

Recent work by Schietinger et al. (*Nano Lett.* 2010, 10, 134-138) demonstrates similar plasmon enhancement of the emission of upconverting nanocrystals. In this work, the group prepared $NaYF_4$ nanocrystals doped with Er and Yb and codeposited 5 nm Au nanoparticles to a thin film. AFM tip manipulation coupled with single particle emission spectroscopy confirmed a 2.7 to 4.8 fold enhancement of the upconverting nanocrystals in a thin film deposition.

The doped yttrium oxide materials described above as well as the other nanocrystalline materials of the invention are upconverters which offer an alternative to more conventional types of techniques for imaging or photo-induced treatment. In some of the cross referenced related patent applications, high energy photons such as X-ray or high energy particles were used in a down conversion manner to generate subsequent ultraviolet light for interaction with drugs introduced to the body or (in other work) for the production of a singlet oxygen in the body or for diagnostics via imaging the secondarily emitted light. In some of the cross referenced related patent applications, high energy photons such as X-ray or high energy particles were used in a down conversion manner to generate secondarily emitted light which activated an agent in the medium. The interaction of X-ray with nanoparticles and the resultant emission is thus a determining event in the down conversion process of the present invention. It has been discovered that the resultant light emission for $Y_2O_3$ particles show at least in the range from 120 kV to 320 kV an unexpected increase in emission intensity with decreasing X-ray energy.

In one embodiment of this invention, a more benign radiation source (than X-ray) that of a NIR source can be used. NIR sources are readily available with commercial laser sources that operate, for example at 980 and 808 nm. There are many commercially available NIR diode laser lines; these include 785, 830, 852, 915, 940, 1064, 1310, and 1550 nm in addition to 808 and 980, which depending on the nanoscale agent and application, many of these are suitable for use.

The doped yttrium oxide materials described above as well as the other nanocrystalline materials of the invention are upconverters which offer an alternative to more conventional types of techniques for imaging or photo-induced treatment. In some of the cross referenced related patent applications, high energy photons such as X-ray or high energy particles were used in a down conversion manner to generate subsequent ultraviolet light for interaction with drugs introduced to the body or (in other work) for the production of a singlet oxygen in the body or for diagnostics via imaging the secondarily emitted light. In some of the cross referenced related patent applications, high energy photons such as X-ray or high energy particles were used in a down conversion manner to generate secondarily emitted light which activated an agent in the medium. The interaction of X-ray with nanoparticles and the resultant emission is thus a determining event in the down conversion process of the invention. It has been observed that the resultant light emission for $Y_2O_3$ particles show at least in the range from 120 kV to 320 kV an increase in emission intensity with decreasing X-ray energy. Other particles or other energy ranges may well show a different trend.

In one embodiment of this invention, a more benign radiation source, that of a NIR source, can be used. NIR sources are readily available with commercial laser sources that operate, for example at 980 and 808 nm. There are many commercially available NIR diode laser lines; these include 785, 830, 852, 915, 940, 1064, 1310, and 1550 nm in addition to 808 and 980, which depending on the nanoscale agent and application, many of these are suitable for use.

Medical Applications

These IR frequencies have significant penetration into the human body and permit the primary excitation $\lambda_1$ to penetrate subcutaneously into the body tissue. Upon their penetration into the body tissue, the dielectric core of the invention interacts with the incident radiation $\lambda_1$ to generate the secondary light $\lambda_2$ as described above. Therefore, permitting the generation in situ to the body of a wavelength $\lambda_2$ which may be in the UV or visible range is appropriate for activations of psoralen or other types of drugs known to be activated by a UV or visible light source.

Since the dielectric cores of this invention have the ability to be selectively stimulated by discrete wavelengths of $\lambda_1$ and produce discrete emission wavelengths at $\lambda_2$, the medial applications can be manipulated so that a number of dual purpose diagnostic/treatment tools can be produced.

For example, in one embodiment of the invention, a material such as the above-described co-doped yttrium oxide is introduced into the body. Yttrium oxide as a host is known to be a down converter from X-ray radiation. In this particular example, X-ray incident radiation on the yttrium oxide will produce UV light which would in turn be used to activate drugs such as psoralen for the treatment of cancer. Meanwhile, the co-doped yttrium oxide as a upconverter could be used where the NIR excitation could produce an emission at a wavelength that was different than that produced from the X-ray down conversion radiation. In this manner, the progression of the yttrium oxide (with drug attached as the recipient 4) into a target organ to be treated could be monitored using the NIR light as the excitation source and collecting the visible light in some type of CCD camera. Once the yttrium oxide particles were absorbed into the respective tumor cells for treatment, at that point in time, X-ray radiation could be initiated and thereby activating the psoralen tagged yttrium oxide and providing an effective means for treating the tumor cell.

Figure 8H:
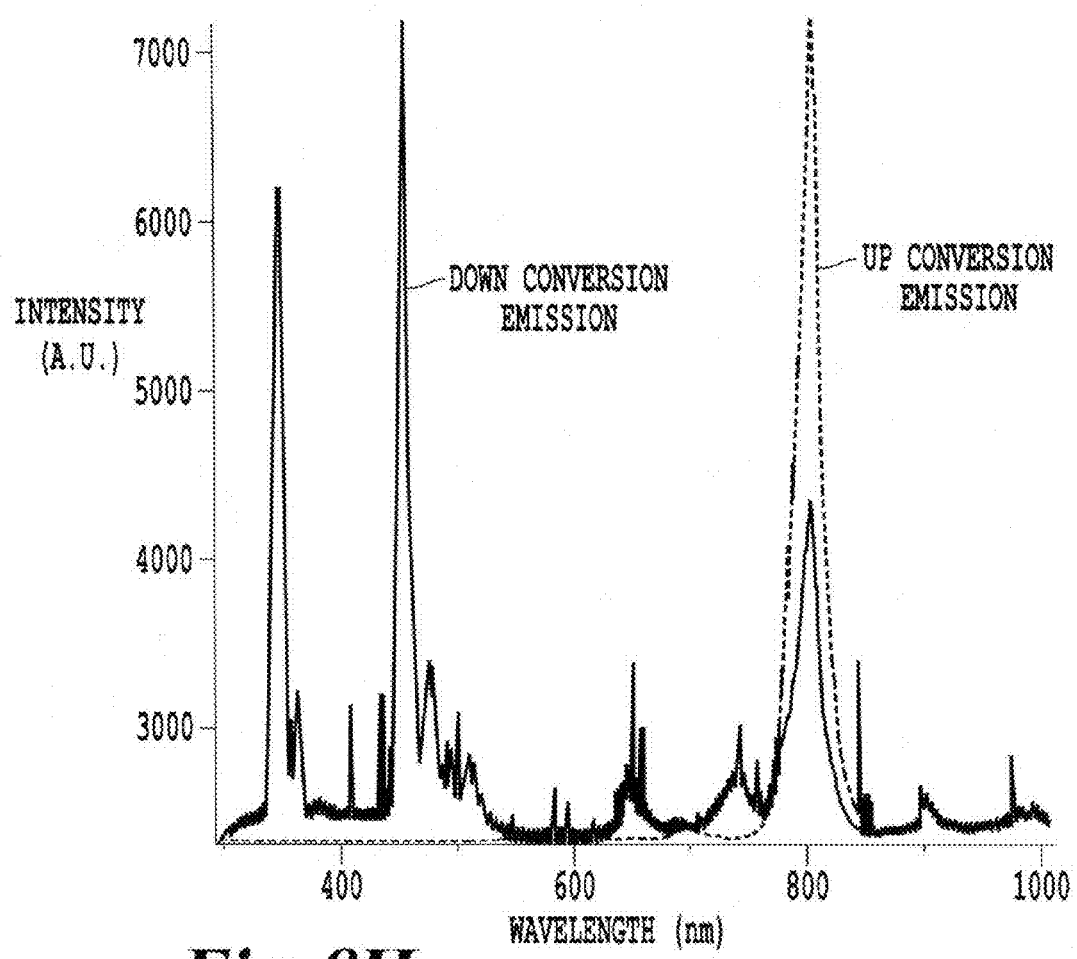
FIG. 8H is a depiction of both down conversion and up conversion emission from a thulium doped nanoparticle ($NaYbF_4$; 3% Tm)
Figure 8I:
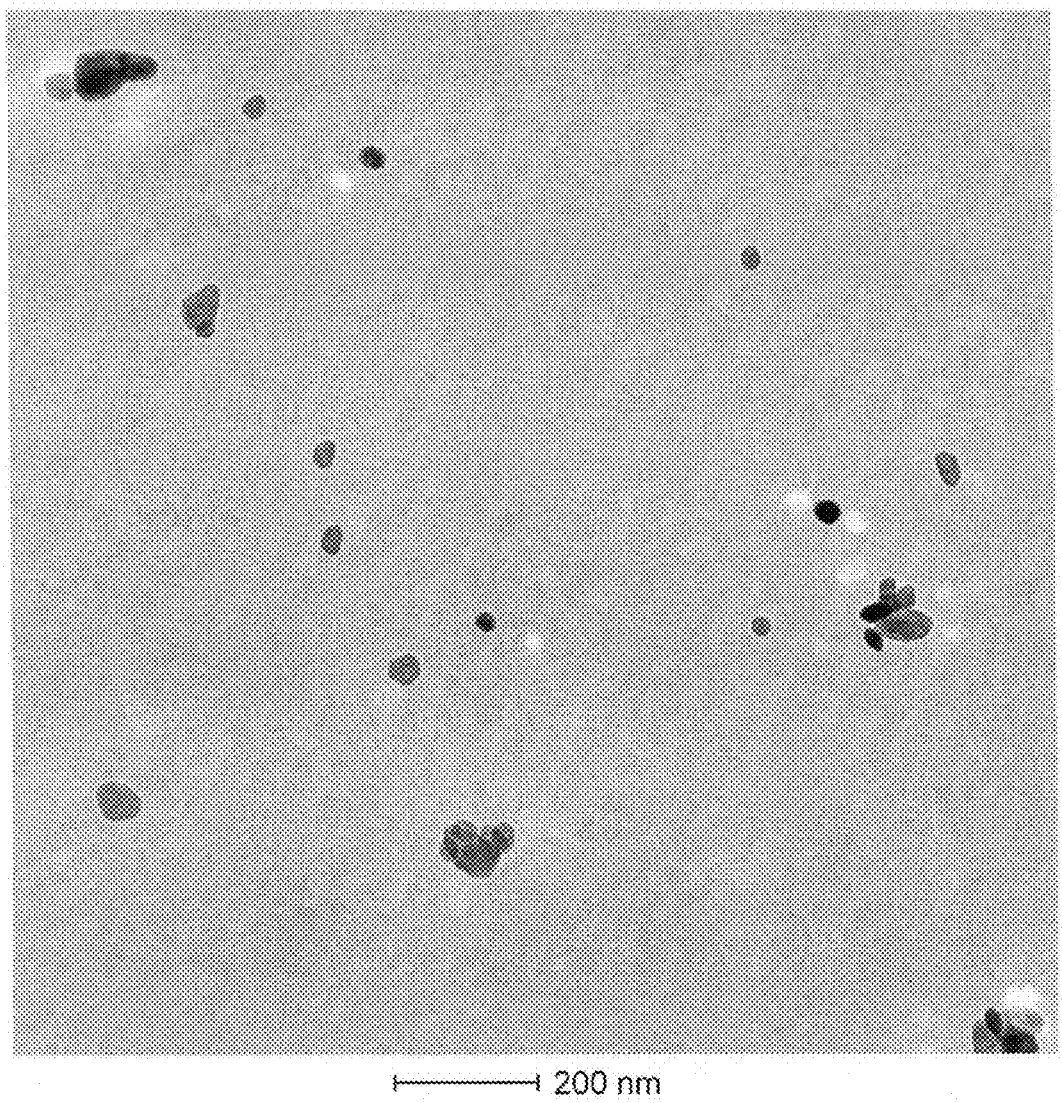
FIG. 8I is a micrograph of a representative 35 nm PEI Coated $YbF_3$; Tm (2%) particle.

FIG. 8H is a depiction of down conversion and up conversion emission from a $NaYbF_3$; Tm nanoparticle. The up conversion lines were excited at 980 nm. The down conversion lines were excited with 320 kV x-rays. FIG. 8I is a micrograph of a representative 35 nm PEI Coated $YbF_3$; Tm (2%) particle.

Alternatively, in another dual purpose diagnostic/treatment example, one can choose a system where the NIR wavelength is specifically tuned for diagnostics as explained above while excitation with a separate wavelength of NIR can be used to produce UV light (through another upconversion channel) that would itself activate a recipient molecule (e.g. psoralen for cancer treatment) without the necessity of X-ray and down conversion activation. This feature then permits one to use a drug which either would be acceptable for deep body penetration through X-ray radiation or would be acceptable for more shallow body penetration through NIR radiation to treat cancer cells that were located in different parts of the body relative to the surface of the body. Moreover, fiber optics could be used to direct the NIR light (through a surgical incision for example) directly to a target. By locally activating the psoralen and by the known autovaccine effect, this initially local NIR activated treatment may be effective at treating cancer outside the NIR irradiated area.

Examples of such dual use drugs which all exhibit NIR activation and upconversion for the purpose of imaging and/or to excite psoralen would include the dual dopants of yttrium oxide, the dual dopants of neodymium oxide, triply doped ytterbium thulium neodymium oxides, the dual dopants of sodium yttrium fluoride, and the dual dopants of lanthanum fluoride. For example, by providing a ytterbium-thulium doped yttrium oxide containing 95% verses 5% dopant concentration with another lanthanide, one will produce diagnostic/treatment functions through pure NIR excitation, having the drug treatment excitable at 980 nanometers verses the diagnostic imaging process excitable at 808 nanometers with different emissions coming from each excitation process.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Tagging and Labeling Applications

Besides the medical applications presented above, the nanotechnology of the invention has applications in other areas such as security and tagging operations where a primary light source, for example a NIR beam is focused and directed onto a target object. Applications of these materials include: (i) detecting and removing of counterfeit currency from circulation, (ii) detecting and removing of counterfeit adulterated products (e.g., fake drugs), (iii) tracing the origin of products (e.g., alcohol, tobacco, firearms) and commodities (e.g., oil/gas tag and trace), (iv) tagging controlled substances (e.g. military explosives) or restricted technology (e.g. nuclear and communications technologies), (v) marking single source, high value commodities (e.g., specialty fibers), and (vi) brand protection, and (vii) verifying the authenticity of documents, financial instruments (e.g. bearer bonds), and various forms of identification. With the NIR beam incident on nanoparticles of yttrium oxide for example, the yttrium oxide nanoparticles will emit in the visible wavelength range which can then be detected by a hand-held reader, a CCD camera, or a person's eyes. For example, 100 to 1,000 milliwatt power of NIR light at wavelength at 980 nanometers, upconverters of the types described in this application show bright green emission, blue emission, or red emission to the naked eye, emission so bright that one has to turn away viewing directly the emission.

Alternatively or complementarily, the nanotechnology of the invention has applications in security and tagging operations where the primary light source is X-ray excitation and UV/VIS/NIR readout is used for the viewing.

In conventional bar coding operations, a scanner is used to essentially read a series of black and white lines with the density and spacings being indicative of a particular coded item. In this invention, these printed bar codes could make use of the nanocore emitters described above which offer the possibility of a multicolor emission from either singular or multiple infrared laser sources. Thus, the amount of information that can be encoded into a traditional bar code area may be greatly increased. For example, specific color categorization could introduce completely different encodings for what would normally be the same series of black and white lines. Further, combinations of differing color lines would permit further encoding of information even on top of the existing bar code lines which could be read by existing black and white imagers, adding information that would be indicative of the classes of product, class of distributers, class of manufacturers, classes of retailers, etc., in the product distribution chain. In this way, bar codes applied at the manufacture or food packager could be used for example in food product tracking safety and monitoring.

In these tagging and labeling applications, the invention provides a system for identification of an object. The system includes a readable medium (e.g., a paper product, a plastic product, and a glass product which may be a part of a security tag or a bar code on any product), a nanoparticle included in or on the surface of the readable medium. The nanoparticle, upon exposure to a first wavelength $\lambda_1$ of radiation, is configured to emit a second wavelength $\lambda_2$ of radiation having a higher energy than the first wavelength $\lambda_1$. The second wavelength $\lambda_2$ is in at least one of infrared, visible, and ultraviolet light to permit identification of the object by detecting the second wavelength $\lambda_2$.

A metallic shell can encapsulate at least a fraction of the nanoparticle. As explained above, a radial dimension of the metallic shell can be set to a value where a surface plasmon resonance in the metallic shell resonates at a frequency which provides spectral overlap with either the first wavelength $\lambda_1$ or the second wavelength $\lambda_2$. The nanoparticle can more generally include a plurality of nanoparticles.

As such, the nanoparticles can be divided into multiple groups or categories of different light-emitting nanoparticles. A first group can for example exhibit visible emission upon interaction with the first wavelength $\lambda_1$, while a second group can exhibit infrared emission upon interaction with the first wavelength $\lambda_1$. In this embodiment, the first group can be a part of a visible tag on the object, and the second group can be a part of an invisible tag on the object. Alternatively, the first group can exhibit visible emission upon interaction with the first wavelength $\lambda_1$, while the second group can exhibit ultraviolet emission upon interaction with the first wavelength $\lambda_1$. In this embodiment also, the first group can be a part of a visible tag on the object, and the second group can be a part of an invisible tag on the object.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Quality Control and Environmental Sensor Applications

In one embodiment of the invention, a plasmonic effect is also available via Raman scattering, thereby providing a "signature" for the psoralen compound being used as a drug. Accordingly, in one embodiment of this invention, Raman scattering from these attached recipients 6 can be used as an indicator of the presence or absence of plasmonic shells 6, the proximity of the psoralen to the plasmonic shell, etc. As such, the Raman enhancement effects can be used as a diagnostic to identify either for 1) quality control measures, 2) assay measurements, or 3) product identification to determine the type of psoralen in use or to be used.

Raman spectroscopy was originally developed to study vibrational modes of molecules, and has proven to be a valuable tool for characterizing lattice vibrations, phonon modes, of nanocrystals. Raman analysis has been shown to be fairly effective in identifying the differences in the local chemical and crystalline structure about certain crystalline systems. Presently, diode lasers and CCD cameras with the spectral dispersion elements can be used to instantaneously take Raman spectra from a wide variety of materials with digital counting techniques available capture instantaneously an entire Raman spectrum and derive the spectrum with sufficient signal to noise ratios which once required by high precision grating instruments and photon counting detectors.

Further, since the surface plasmon effect is a resonance of electrons in the metallic shell 4 being confined between the dielectric inner core and the environmental dielectric material, the plasmon resonance will be affected by the dielectric properties of the medium itself. Thus, in one embodiment of the invention, the novel dielectric core/shell structures are used in conjunction with a Raman instrument as an environmental sensor.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Sterilization and Cold Pasteurization of Fluids

Table 1 included below shows appropriate intensities for germicidal destruction with UV light irradiation.

TABLE 1

| Germicidal energies needed to destroy Approximate intensity ($\mu W/cm^2$) required for 99% destruction of microorganisms: | |
| --- | --- |
| Bacteria | 10 400 |
| Protozoa (single celled organism) | 105 000 |
| Paramecium (slipper shaped protozoa) | 200 000 |
| Chlorella (unicellular fresh-water alga) | 13 000 |
| Flagellate (protozoan or alga with flagella) | 22 000 |
| Sporozoan (parasitic protozoans) | 100 000 |
| Virus | 8 000 |

Figure 9A:
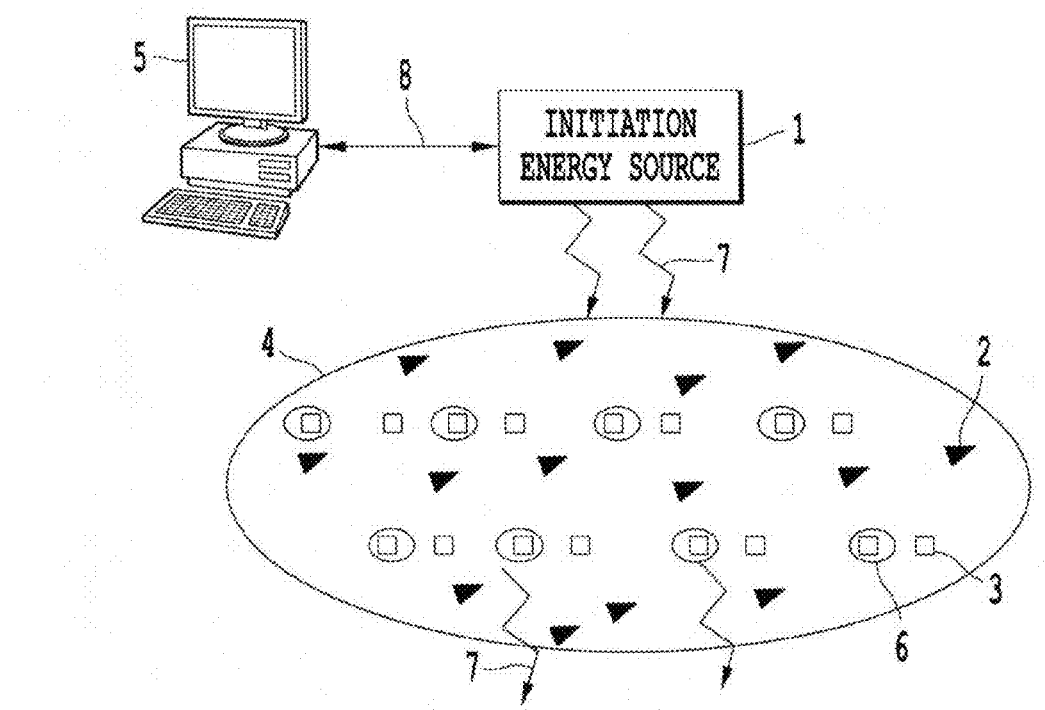
FIG. 9A is a schematic depicting a system according to another embodiment of the invention in which the initiation energy source is directed to a medium having energy modulation agents disbursed within the medium.

As shown in FIG. 9A, an exemplary system according to one embodiment of the invention may have an initiation energy source 1 directed at medium 4. Activatable agents 2 and energy modulation agents 3 are dispersed throughout the medium 4. The initiation energy source 1 may additionally be connected via a network 8 to a computer system 5 capable of directing the delivery of the initiation energy. In various embodiments, the energy modulation agents 3 are encapsulated energy modulation agents 6, depicted in FIG. 9A as silica encased energy modulation agents. As shown in FIG. 9A, initiation energy 7 in the form of radiation from the initiation energy source 1 permeates throughout the medium 4.

As discussed below in more detail, the initiation energy source 1 can be an external energy source or an energy source located at least partially in the medium 4. As discussed below in more detail, activatable agents 2 and/or the energy modulation agents 3 can include plasmonics agents which enhance either the applied energy or the energy emitted from the energy modulation agents 3 so as to directly or indirectly produce a change in the medium.

In various embodiments, the initiation energy source 1 may be a linear accelerator equipped with image guided computer-control capability to deliver a precisely calibrated beam of radiation to a pre-selected coordinate. In these embodiments, down conversion is used to generate internal light inside the medium. One example of such linear accelerators is the SmartBeam™ IMRT (intensity modulated radiation therapy) system from Varian medical systems (Varian Medical Systems, Inc., Palo Alto, Calif.). In other embodiments, the initiation energy source 1 may be commercially available components of X-ray machines or non-medical X-ray machines. X-ray machines that produce from 10 to 150 keV X-rays are readily available in the marketplace. For instance, the General Electric Definium series or the Siemens MULTIX series are but two examples of typical X-ray machines designed for the medical industry, while the Eagle Pack series from Smith Detection is an example of a non-medical X-ray machine. As such, the invention is capable of performing its desired function when used in conjunction with commercial X-ray equipment.

In other embodiments, the initiation energy source 1 can be a radio frequency or microwave source or infrared source (as discussed above) emitting electromagnetic waves at a frequency which permeates the medium and which triggers or produces or enhances secondary radiant energy emission within the medium by interaction with the energy modulation elements 6 therein. In other embodiments, the initiation energy source 1 can be an ultraviolet, visible, near infrared (NIR) or infrared (IR) emitter emitting at a frequency which permeates the medium 4 and which triggers or produces secondary radiant energy emission within medium 4 by interaction with the energy modulation elements 6 therein.

Figure 9B:
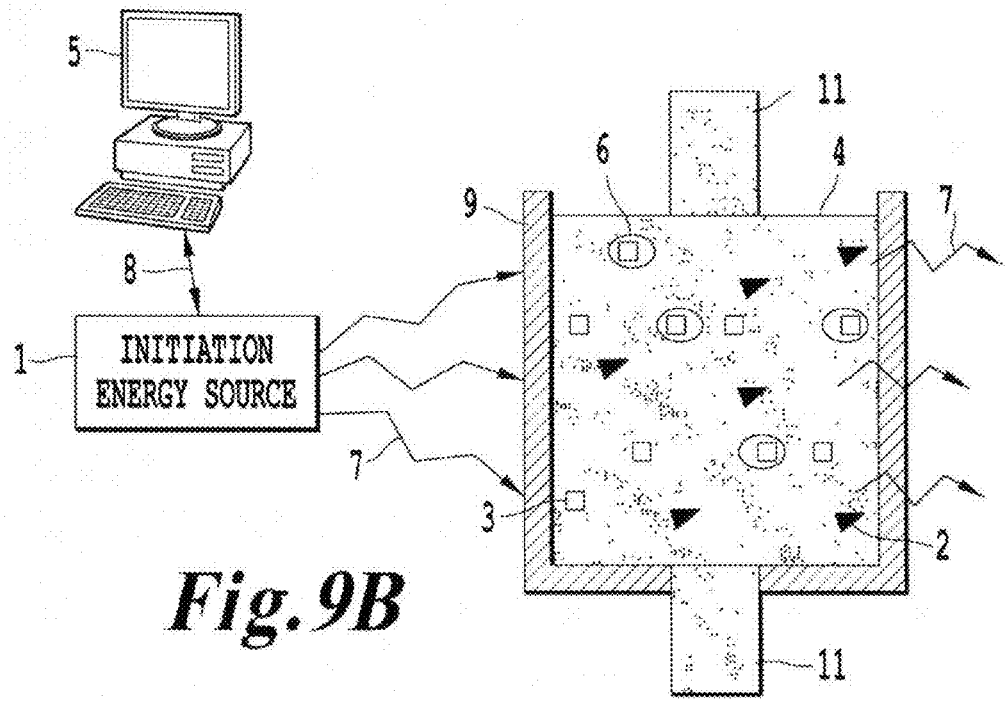
FIG. 9B is a schematic depicting a system according to another embodiment of the invention in which the initiation energy source is directed to a container enclosing a medium having energy modulation agents disbursed within the medium.

FIG. 9B is a schematic depicting another system according to another embodiment of the invention in which the initiation energy source 1 of FIG. 9A is directed to energy modulation elements 6 placed in the vicinity of a fluid medium 4 (e.g., a liquid or other fluid-like medium) and held inside a container 9. The container 9 is made of a material that is "transparent" to the radiation 7. For example, plastic, quartz, glass, or aluminum containers would be sufficiently transparent to X-rays, while plastic or quartz or glass containers would be transparent to microwave or radio frequency radiation. The energy modulation elements 6 can be dispersed uniformly throughout the medium or may be segregated in distinct parts of the medium or further separated physically from the medium by encapsulation structures 10, as described below. A supply 11 provides the medium 4 to the container 9.

Figure 9C:
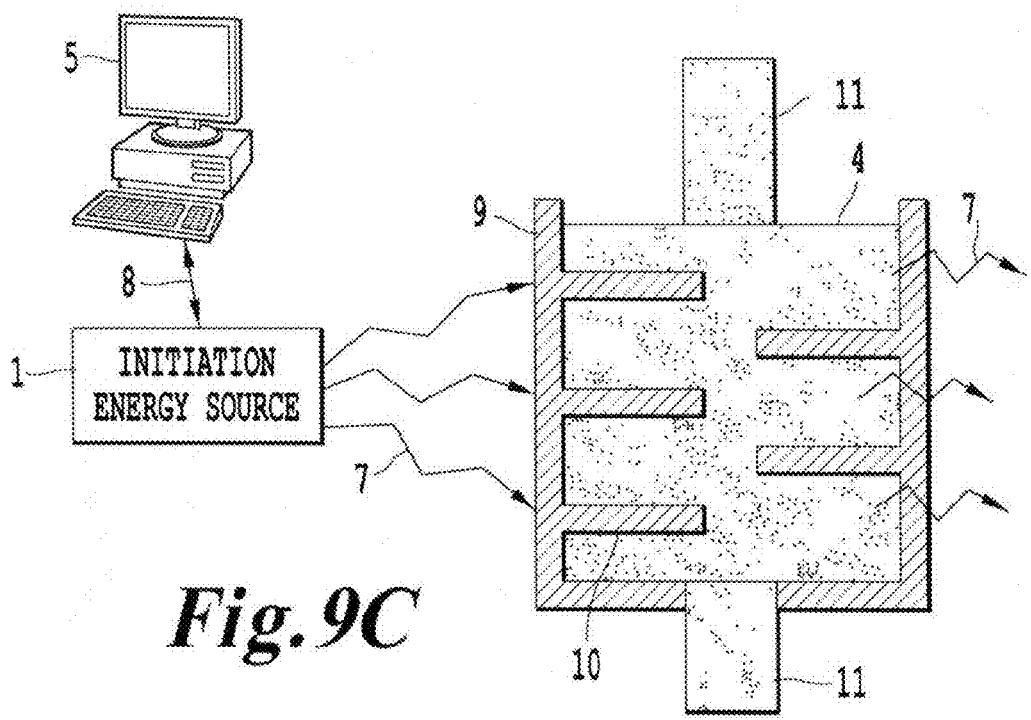
FIG. 9C is a schematic depicting a system according to another embodiment of the invention in which the initiation energy source is directed to a container enclosing a medium having energy modulation agents segregated within the medium.

Alternatively, as shown in FIG. 9C, the luminescent particles could be present in the medium in encapsulated structures 10. In one embodiment, the encapsulated structures 10 are aligned with an orientation in line with the external initiation energy source 1. In this configuration, each of the encapsulated structures 10 has itself a "line-of-sight" to the external initiation energy source 1 shown in FIG. 9C without being occluded by other of the encapsulated structures 10. In other embodiments, the encapsulated structures 10 are not so aligned in that direction, but could aligned perpendicular to the direction shown in FIG. 9C, or could be randomly placed. Indeed, supply of fluid medium 4 could itself be used to agitate the encapsulated structures 10 and mix the fluid medium 4 inside container 9.

The system of FIG. 9C may also be used without energy modulation agents. In this embodiment, the initiation energy source 1 can be for example at an energy suitable for driving physical, chemical, and/or biological processes in the fluid medium 4. The plasmonics agents included in the encapsulated structures 10 effectively amplify the light from the initiation energy source 1 as it interacts with the medium 4.

Figure 9D:
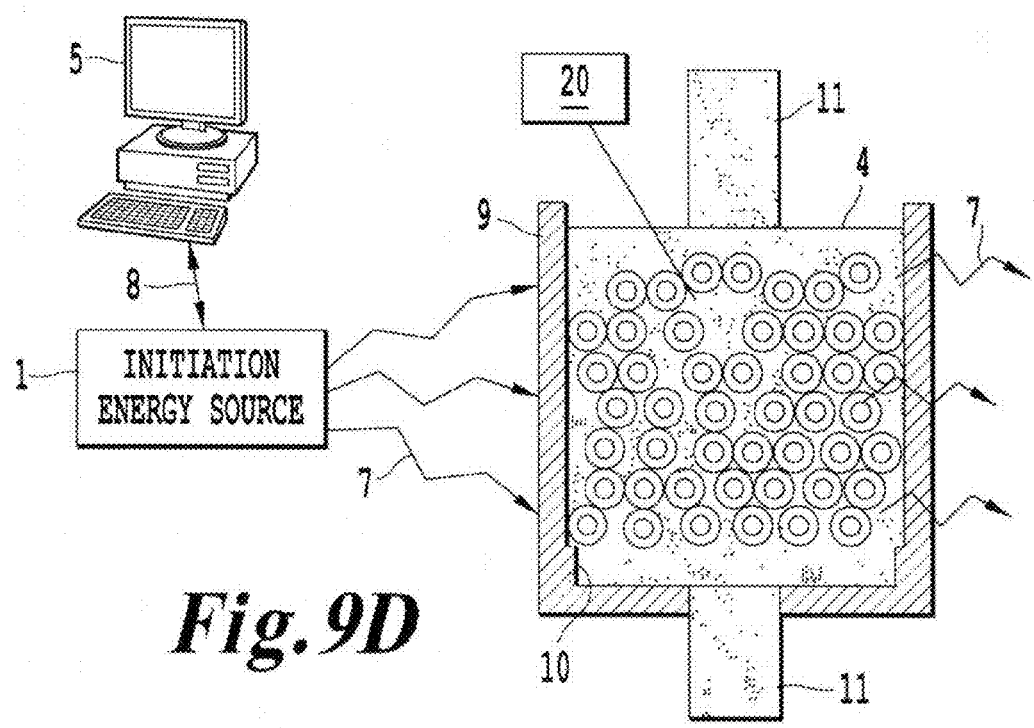
FIG. 9D is a schematic depicting a system according to another embodiment of the invention in which the initiation energy source is directed to a container enclosing a medium having energy modulation agents segregated within the medium in a fluidized bed configuration.

FIG. 9D is a schematic depicting a system according to another embodiment of the invention in which the initiation energy source is directed a container enclosing a medium having energy modulation agents segregated within the medium in a fluidized bed 20 configurations. The fluidized bed 20 includes the encapsulated structures 10 in a configuration where a fluid to be treated is passed between the encapsulated structures 10. The encapsulated structures 10 can include both energy modulation agents and plasmonics agents as described herein.

In the either configuration of FIGS. 9C and 9D, the medium to be treated would flow by the encapsulated structures 10, or flow along with encapsulated structures 6, and the separation distance between the encapsulated structures 6, 10 would be set a distance smaller than the UV penetration depth in the medium.

In further embodiments of the invention, robotic manipulation devices may also be included in the systems of FIGS. 9A, 9B, 9C, and 9D for the purpose of delivering and dispersing the energy modulation elements 6 in medium 4 or for the purpose of removing old product and introducing new product for treatment into the system.

A suitable light source (such as one of the X-ray sources for down converting or the infrared radiation sources, microwave sources, or radio frequency sources for up conversion) can be used to stimulate the luminescent particles in the encapsulated structures 10. In one embodiment of the invention described here, the concentration of luminescent particles in the medium or the spacing between the encapsulated structures 10 is set such that luminescent particles are separated from each other in the medium by less than a UV depth of penetration into the medium. Higher concentrations are certainly usable and will generate higher UV fluxes should the energy source have enough intensity to "light" all the luminescent particles.

For a relatively unclouded aqueous medium, UV-B irradiance decreases to 1% after penetration into the water samples between 0.2 m and 1 m, whereas UV-A penetrates on the order of several meters. For such mediums, the concentration of luminescent particles is more determined by the time needed for the intended UV flux to produce deactivation or activation of an agent in the medium, rather than having to be set based on a concentration of luminescent particles where the medium itself does not occlude the UV stimulated emission from penetrating throughout the medium. The placement of the luminescent particles in the medium and in the vicinity of the medium is not restricted by the optical density of the medium.

Accordingly, the upconverter structures of the invention (as discussed above) can be provided on the interior of sealed quartz or glass tubes or can be provided coated on the surface of spheres or tubes, and further encapsulated with a silicate or another passivation layer. In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone.

In this application, it is known that ultraviolet (UV) with a wavelength of 254 nm tends to inactivate most types of microorganisms. Most juices are opaque to UV due to the high-suspended solids in them and hence the conventional UV treatment, usually used for water treatment, cannot be used for treating juices. In order to make the process efficient, a thin film reactor constructed from glass has been used with the juice flowing along the inner surface of a vertical glass tube as a thin film. See "Ultraviolet Treatment of Orange Juice" by Tran et al. published in Innovative Food Science & Emerging Technologies (Volume 5, Issue 4, December 2004, Pages 495-502), the entire contents of which are incorporated herein by reference. Tran et al. reported that decimal reduction doses required for the reconstitute orange juices (OJ; 10.5° Brix) were 87±7 and 119±17 mJ/cm$^2$ for the standard aerobic plate count (APC) and yeast and moulds, respectively. They also reported that the shelf life of fresh squeezed orange juice was extended to 5 days with a limited exposure of UV (73.8 mJ/cm$^2$). The effect of UV on the concentration of Vitamin C was investigated using both HPLC and titration methods of measurements. The degradation of Vitamin C was 17% under high UV exposure of 100 mJ/cm$^2$, which was similar to that usually found in thermal sterilization. Enzyme pectin methylesterase (PME) activity, which is the major cause of cloud loss of juices, was also measured. The energy required for UV treatment of orange juice (2.0 kW h/m$^3$) was much smaller than that required in thermal treatment (82 kW h/m$^3$). The color and pH of the juice were not significantly influenced by the treatment.

The invention described herein offers advantages over this approach in that the upconverter structures of the invention can be placed inside fixtures such as quartz or glass (encapsulation structures) within the orange juice (or other fluid medium) and irradiated with NIR light supplied for example to the contained through manifold fiber optics to activate the encapsulated upconverter structures of the invention in the orange juice.

While discussed with regard to orange juice, any other medium to be sterilized including food products, medical products and cosmetic products could be treated using the technique of the invention described herein.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Sterilization of Blood Products

U.S. Pat. No. 6,087,141 (the entire contents of which are incorporated herein by reference) describes an ultraviolet light activated psoralen process for sterilization of blood transfusion products. The invention can be applied for the neutralization of AIDS and HIV or other viral or pathogenic agents in blood transfusion products. In this embodiment, at least one photoactivatable agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, anthroquinones, porphycene, rubyrin, rosarin, hexaphyrin, sapphyrin, chlorphyl, chlorin, phthalocynine, porphyrazine, bacteriochlorophyl, pheophytin, texaphyrin macrocyclic-based component, or a metalated derivative thereof. These photoactivatable agents serve as recipients for the secondarily generated light induced by the down conversion or upconversion.

The recipient in this and other embodiments of the invention can include at least one of a laser dye, a fluorophore, a lumophore, or a phosphor. The laser dye can be at least one of p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2,7-dichlorofluorescein, rhodamine 65, and rhodamin 19 perchlorate, rhodamine b, and derivatives of these laser dyes that are modified by addition the addition of appropriate substituents to modify solubility or tune their interactions within the biological milieu.

In various embodiments of the invention, the recipients are secondary agents performing other functions. Suitable secondary agents for the invention include secondary emitters, cytotoxic agents, magnetic resonance imaging (MRI) agents, positron emission tomography (PET) agents, radiological imaging agents, or photodynamic therapy (PDT) agents.

These photoactivatable agents (recipients and secondary agents) are introduced into the blood product (or a patient's blood stream). NIR light is applied to the blood product (or to the patient). The upconverter structures of the invention (either included in the blood product) or in encapsulated structures generate secondary light such as UV light which activates the photoactivatable agents in the blood products. In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Waste Water Detoxification

Photocatalysis has also been used as tertiary treatment for wastewater to comply with regulatory discharge limits and to oxidize compounds that have not been oxidized in the biological treatment. Photocatalysis has been used to reduce or eliminate several pollutants (e.g., alkanes, alkenes, phenols, aromatics, pesticides) with great success. In many cases, total mineralization of the organic compounds has been observed. Several photocatalysts, such as CdS, $Fe_2O_3$, ZnO, $WO_3$, and ZnS, have been studied, but the best results have been achieved with $TiO_2P_{25}$. These photocatalyst can be used in the invention.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

It is known that photocatalysis can be used for waste water reduction remediation. U.S. Pat. No. 5,118,422 (the entire contents of which are incorporated herein by reference) to Cooper et al. describe an ultraviolet driven photocatalytic post-treatment technique for purifying a water feedstock containing an oxidizable contaminant compound. In this work, the water feedstock was mixed with photocatalytic semiconductor particles (e.g., $TiO_2$, ZnO, CdS, CdSe, $SnO_2$, $SrTiO_3$, $WO_3$, $Fe_2O_3$, and $Ta_2O_5$ particles) having a particle size in the range of about 0.01 to about 1.0 micron and in an amount of between about 0.01% and about 0.2% by weight of the water. The water including the semiconductor mixture is exposed to band-gap photons for a time sufficient to affect an oxidation of the oxidizable contaminant to purify the water. Crossflow membrane filtration was used to separate the purified water from the semiconductor particles. Cooper et al. show that the organic impurity carbon content of simulated reclamation waters at nominal 40 PPM level were reduced to parts per billion using a recirculation batch reactor.

Cooper et al. identified that one important aspect of the photocatalytic process is the adsorption of the organic molecules onto the extremely large surface area presented by the finely divided powders dispersed in the water. Cooper et al. further indicated that, in photoelectrochemical applications, advantage is taken of the fact that the solid phase (a metal oxide semiconductor) is also photo-active and that the generated charge carriers are directly involved in the organic oxidation. The adsorption of the band-gap photon by the semiconductor particle results in the formation of an electron ($e^-$)/hole ($h^+$) pair. Cooper et al. explain that the electrons generated in the conduction band react with solution oxygen forming the dioxygen anion ($O_{2-}$) species which subsequently undergo further reactions resulting in the production of the powerfully oxidizing hydroxyl radical species, .OH. These powerful oxidants are known to oxidize organic compounds by themselves. Additionally, Cooper et al. explain that the strongly oxidizing holes generated in the valence band have sufficient energy to oxidize all organic bonds.

In the reactor of Cooper et al., turbulence is necessary in order to ensure that the waste water contaminants and the photocatalytic titania particles are exposed to the UV light. Cooper et al. explain that the most basic considerations of photocatalyst light adsorption and its relationship to convective mixing. For a 0.1 wt % photocatalyst loading, experiments have shown that 90% of the light is absorbed within 0.08 cm. This is primarily due to the large UV absorption coefficient of the photocatalyst and therefore, most of the photoelectrochemistry occurs within this illuminated region. By operating the reactor of Cooper et al. with a Reynolds number (Re) of 4000, a significant portion of the photoactive region is ensured of being within the well mixed turbulent zone.

Santos et al. have reported in "Photocatalysis as a tertiary treatment for petroleum refinery wastewaters" published in Braz. J. Chem. Eng. vol. 23, No. 4, 2006 (the entire contents of which are incorporated herein by reference), photocatalysis for tertiary treatment for petroleum refinery wastewaters which satisfactorily reduced the amount of pollutants to the level of the regulatory discharge limits and oxidized persistent compounds that had not been oxidized in the biological treatment. The treatment sequence used by the refinery (REDUC/PETROBRAS, a Brazilian oil refinery) is oil/water separation followed by a biological treatment. Although the process efficiency in terms of biological oxygen demand (BOD) removal is high, a residual and persistent COD and a phenol content remains. The refining capacity of the refinery is 41,000 $m^3$/day, generating 1,100 $m^3$/h of wastewater, which are discharged directly into the Guanabara Bay (Rio de Janeiro). Treating the residual and persistent COD remains a priority.

Santos et al. conducted a first set of experiments carried out in an open 250 mL reactor containing 60 mL of wastewater. In the second set of experiments, a Pyrex® annular reactor containing 550 mL of wastewater was used (De Paoli and Rodrigues, 1978), as shown in FIG. 1. The reaction mixtures inside the reactors were maintained in suspension by magnetic stirring. In all experiments, air was continuously bubbled through the suspensions. A 250 W Phillips HPL-medium pressure mercury vapor lamp (with its outer bulb removed) was used as the UV-light source (radiant flux of 108

J·m$^{-2}$·s$^{-1}$ at λ>254 nm). In one set of experiments, the lamp was positioned above the surface of the liquid at a fixed height (12 cm). In the second set, the lamp was inserted into the well. All experiments by Santos et al. were performed at 25±1° C. The catalyst concentration ranged from 0.5 to 5.5 g L$^{-1}$ and the initial pH ranged from 3.5 to 9.

In one embodiment of the invention described herein, the upconverter structures of the invention would be placed inside quartz or glass fixtures within the waste water or would be placed on silica encapsulated structures within the waste water which, like the photocatalytic $TiO_2$, could be entrained in the waste water during the irradiation.

Upon irradiation with for example NIR or IR radiation through for example a manifold of fiber optics activation of the upconverter structures of the invention would generate UV light in nearby presence of the photocatalytic agent. In other words for this embodiment, the upconverter structures of the invention are mixed along with the photocatalytic semiconductor particles in the waste water fluid stream, and the exterior activation energy source penetrates the container (e.g., a plastic or aluminum container) and irradiates the bulk of the waste water, producing UV light throughout the waste water which in turn drives the photocatalytic reactions.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

Workers have found that UV irradiation could realize an effective graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photografting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of the upconverter structures of the invention in dispersion in the fluid medium being used for photostimulation. Upon NIR irradiation, the upconverter structures of the invention would generate UV light within the NIR penetration depth of the medium and permitting batch or bulk type processing to occur in parallel inside the container. Further, when laser light is used for the NIR, the plastic surface can be "written" onto such that inks would selectively absorb on those regions where surface of the polymer was exposed to the UV generated light.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Wanting to stop the fermentation process is all good in and of itself. But unfortunately, there is really no practical way to successfully stop a fermentation dead in its tracks. Additives such as sulphite and sorbate can be added to stabilize a fermented product and stop additional fermentation. Many winemakers will turn to sulfites such as that found in Sodium Bisulfite or Campden tablets for the answer. But, these two items are not capable of reliably killing enough of the yeast to guarantee a complete stop of the activity—at least not at normal doses that leave the wine still drinkable.

Once the bulk of the sulfites from either of these ingredients dissipate from the wine into the air—as sulfites do—there is a very strong chance that the remaining few live yeast cells will start multiplying and fermenting again if given enough time. This usually happens at a most inconvenient time, like after the wine has been bottled and stowed away.

Potassium sorbate is another ingredient that many winemakers consider when trying to stop a wine from fermenting any further. There is a lot of misunderstanding surrounding this product. It is typically called for by home wine making books when sweetening a wine. This is a situation where the fermentation has already completed and is ready for bottling. One adds the potassium sorbate along with the sugar that is added for sweetening.

The potassium sorbate stops the yeast from fermenting the newly added sugar. So, many winemakers assume potassium sorbate can stop an active fermentation as well, but, potassium sorbate does not kill the yeast at all, but rather it makes the yeast sterile. In other words, it impairs the yeast's ability to reproduce itself. But, it does not hinder the yeast's ability to ferment sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above could be used for the application described here. For non-liquid products, energy modulation agents with little and preferably no toxicity (e.g. Fe oxides or titanium oxides) could be added. Here, the concentration of these additives would likely be limited by any unexpected changes in taste.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Photoactivated Cross-Linking and Curing of Polymers

In this application, the upconverter structures of the invention are provided and distributed into an uncured polymer based medium for the activation of photosensitive agents in the medium to promote cross-linking and curing of the polymer based medium. In one embodiment, the upconverter structures of the invention are complexed with other down-converting luminescent particles or other energy modulation agents prior to being added to the polymer.

For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the upconverter structures of the invention are added.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Loctite Corporation has designed and developed UV and UV/moisture dual curable silicone compositions, which also demonstrate high resistance to flammability and combustibility, where the flame-retardant component is a combination of hydrated alumina and a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with, for example, carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silione resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl) dimethylsilyl.

The photoinitiator component of the invention is not limited to those free radical generators given above, but may be any photoinitiator known in the art, including the afore-mentioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolaminebenzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4,6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis(.eta.sup.5-2,4-cyclopentadien-1-yl)-bis[2,6-difluoro-3-(1H-pyrrol-1-yl)phenyl] titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photoactivated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890, the disclosure of which is expressly incorporated herein by reference.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 um. Other Q-CEL products are shown below in tabular form. Another commercially available hollow glass microsphere is sold by Kish under the trade name SPHERICEL. SPHERICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCHLITE tradename.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxyalkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with luminescing particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are the upconverter structures of the invention. These compositions can then be applied to surfaces of objects to be fixed together or to surfaces where a hard coating is desired or cast in a curable form for the production of molded objects. These compositions upon activation will produce radiant light for photoactivated cure of the luminescing particle containing polymer composition. The density of the upconverter structures in these compositions will depend on the "light transparency" of the luminescing particle containing composition. Where these compositions contain a significant amount of the inorganic filler as discussed above, the concentration of the upconverter structures can be reduced for example as compared to a composition with a black color pigment where the light transparency will be significantly reduced.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the upconverter structures are added to these Bach et al. compositions. Due to the fact that the exterior energy source penetrates deeper into the entirety of the Bach et al. compositions, thicker surface coatings can be realized. Further, the coatings can be applied to intricate surfaces having for example been prepared with recesses or protrusions.

In one embodiment, the upconverter structures of the invention are complexed with the X-ray down converting particles or other energy modulation agents permitting for example X-ray irradiation to also assist in this process. In one embodiment, the X-ray down converting particles or other energy modulation agents or metallic structures described herein permit X-ray irradiation to be used alone or in combination with the up converting particles.

Generalized Upconversion

The invention as described above can be viewed for its aspects of exposing an agent to one source of light or radiation (an initiation source) of a relatively low energy and having the agent produce light or radiation at a relatively higher energy. In one embodiment of the invention, a change is produced in a medium. The change is produced by (1) placing in a vicinity of the medium a nanoparticle or an otherwise upconverting structure, and (2) applying the initiation energy from an energy source through the artificial container to the medium, wherein the emitted light directly or indirectly produces the change in the medium.

The nanoparticle or the otherwise upconverting structure in one embodiment is configured, upon exposure to a first wavelength $\lambda_1$ of radiation, to generate a second wavelength $\lambda_2$ of radiation having a higher energy than the first wavelength $\lambda_1$. The nanoparticle or the otherwise upconverting structure in one embodiment includes a metallic T metallic structure disposed in relation to the nanoparticle (e.g. a metallic shell covering a fraction of the nanoparticle) A receptor in the medium, upon activation by the second wavelength $\lambda_2$, generates directly or indirectly a photostimulated change in the medium. In one embodiment of the invention, a physical characteristic of metallic structure (such as those described above) is set to a value where a surface plasmon resonance in the metallic structure resonates at a frequency which provides spectral overlap with either the first wavelength $\lambda_1$ or the second wavelength $\lambda_2$.

The metallic structure in one embodiment has a radial dimension of the metallic shell set to a value where a surface plasmon resonance in the metallic shell resonates at a frequency which provides spectral overlap with either the first wavelength $\lambda_1$ or the second wavelength $\lambda_2$. The nanoparticle or the otherwise upconverting structure in one embodiment is configured to emit light into the medium upon interaction with an initiation energy having energy in the range of $\lambda_1$.

The change produced in the medium can cure a radiation-curable medium by activating a photoinitiator in the radiation-curable medium. The change produced can result in a photo-stimulated change to a medium. The change produced can result in a radiation cured medium. The change produced can result in a sterilized medium. The change produced can activate a therapeutic drug.

The agents in one embodiment of the invention can include not only the upconverter nanoparticles discussed above, but also can include the infrared-triggered phosphors discussed above. Furthermore, the agents can include fluorescent molecules or luminescent inorganic molecules or phosphorescent molecules (acting as either down or up converters in various embodiments). Suitable agents include, but are not limited to, a metal nanoparticle or a biocompatible metal nanoparticle, a metal coated or uncoated with a biocompatible outer layer, a chemiluminescent molecule whose rate of luminescence is increased by microwave activation, fluorescing dye molecule, gold nanoparticle, a water soluble quantum dot encapsulated by polyamidoamine dendrimers, a luciferase, a biocompatible phosphorescent molecule, a biocompatible fluorescent molecule, a biocompatible scattering molecule, a combined electromagnetic energy harvester molecule, and a lanthanide chelate capable of intense luminescence. Multiple types of agents can be included in the medium.

For many of these agents, the initiation source may well be low frequency sources such as microwave or radio frequency irradiation, where in one embodiment of the invention localized heating of the agent enhances generation of a secondary light and in another embodiment localized field enhancements from the microwave field present in the medium enhance fluorescence, as described in "Microwave-Accelerated Metal-Enhanced Fluorescence (Mamef) With Silver Colloids in 96-Well Plates: Application to Ultra Fast and Sensitive Immunoassays, High Throughput Screening and Drug Discovery," by Aslan et al in Journal of Immunological Methods 312 (2006) 137-147.

For many of these agents, the initiation source may well be low frequency sources such as microwave or radio frequency radiation, where in one embodiment absorption of the microwave radiation by upconverters results in subsequent emission at higher energies toward the infrared, visible, and ultraviolet. The degree to which the upconverted radiation is applicable to the applications described above will be dependent on the conversion efficiencies of the specific metal shell/dielectric core nanostructures and will be dependent on the efficiency of a recipient molecule linked to the specific metal shell/dielectric core nanostructures to absorb the upconverted light.

In one embodiment, there is provided a system for energy upconversion. The system includes a nanoparticle configured in such a way that upon exposure to a first set of radiation having a wavelength $\lambda_1$ or centered around wavelength $\lambda_1$ (also known as a frequency window centered around frequency f1 or $v_1$), to generate a second set of radiation centered around wavelength $\lambda_2$ having a higher quantum energy level than the first set of radiation centered around or having wavelength $\lambda_1$. The system can include for example a metallic shell encapsulating at least a fraction of the nanoparticle. The radial dimension of the metallic shell is set to within a range of suitable values where surface plasmon resonance can take place in the metallic shell under the impingement or incidence of the first set of operating frequencies of interest; this is accomplished through a spectral overlap of the operating frequencies with either the first set of radiation having wavelengths centered at $\lambda_1$ or the second radiations centered around wavelength $\lambda_2$. The range of frequencies in a frequency window centered on a desirable center frequency can be very narrow and under ideal conditions the frequency window contains only one monochromatic radiation having a single frequency.

The system can include for example a metallic structure disposed in relation to the nanoparticle where a physical characteristic of metallic structure (such as those described above) is set to a value where a surface plasmon resonance in the metallic structure resonates at a frequency which provides spectral overlap of the operating frequencies with either the first set of radiation having wavelengths centered at $\lambda_1$ and/or the second radiations centered around wavelength $\lambda_2$. The range of frequencies in a frequency window centered on a desirable center frequency can be very narrow and under ideal conditions the frequency window contains only one monochromatic radiation having a single frequency.

In one embodiment of the invention, the surface plasmon resonance increases an intensity of at least one of the first wavelength $\lambda_1$ or the second wavelength $\lambda_2$ in a vicinity of the nanoparticle, to thereby enhance the likelihood that the desirable reaction takes place.

In another embodiment, there is provided a system for producing a photostimulated reaction in a medium. The system includes a nanoparticle configured, upon exposure to a first radiation having wavelength $\lambda_1$, to generate a second radiation having wavelength $\lambda_2$ with a higher quantum energy level than the first radiation having wavelength $\lambda_1$. The system includes a metallic structure disposed in relation to the nanoparticle (e.g., a metallic shell encapsulating at least a fraction of the nanoparticle) and includes a receptor disposed in the medium in proximity to the nanoparticle. The receptor upon activation by the second wavelength $\lambda_2$ generates the photostimulated reaction.

In yet another embodiment, there is provided a nanoparticle structure including a sub 1000 nm dielectric core and a metallic shell encapsulating at least a fraction of the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. These dielectric cores can be doped with Er, Eu, Yb, Tm, Nd, Tb, Ce, Y, U, Pr, La, Gd and other rare-earth species or a combination thereof. Such nanoparticle structures including one or more of these dielectric cores can exhibit in certain embodiments surface plasmon resonance in the metallic shell to enhance up conversion of light or electromagnetic radiation from a first wavelength $\lambda_1$ to a second wavelength $\lambda_2$.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A system for energy upconversion inside a medium, comprising:
   an up-converter particle disposed in the medium and configured, upon exposure to a first wavelength $\lambda_1$ of radiation, to generate a second wavelength $\lambda_2$ of radiation having a higher energy than the first wavelength $\lambda_1$; and
   a metallic structure disposed in relation to the up-converter particle and inside the medium,
   wherein
   the second wavelength $\lambda_2$ of radiation comprises ultraviolet emission generated within the medium surrounding the up-converter particle and the metallic structure, and
   said ultraviolet emission produces a physical structural change to an entity in the medium.

2. The system of claim 1, wherein the metallic structure comprises a metallic shell encapsulating at least a fraction of the up-converter particle in the metallic shell and a physical characteristic of the metallic structure is set to a value where a surface plasmon resonance in the metallic structure resonates at a frequency which provides spectral overlap with either the first wavelength $\lambda_1$ or the second wavelength $\lambda_2$ or which provides spectral overlap with both the first wavelength $\lambda_1$ and the second wavelength $\lambda_2$.

3. The system of claim 1, wherein the metallic structure comprises at least one of a conducting material including at least one or more of a metal, a doped glass, a doped semiconductor.

4. The system of claim 3, wherein the conducting material comprises at least one of more of an elemental metal, an alloys of an element metal, or layers of the conducting materials.

5. The system of claim 1, wherein the up-converter particle comprises at least one of a dielectric, a glass, or a semiconductor.

6. The system of claim 1, wherein:
   the up-converter particle comprises a dielectric particle; and
   the dielectric particle comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

7. The system of claim 1, wherein the up-converter particle comprises an alloy of two or more dielectric materials, an alloy of two or more glasses, or an alloy of two or more semiconductors.

8. The system of claim 1, wherein the up-converter particle comprises a nanoparticle having a size less than 1000 nm.

9. The system of claim 1, wherein the up-converter particle comprises an alloy of two or more materials, wherein the alloy has a composition between the two or materials set to a compositional value where excitation of the alloy at the first wavelength $\lambda_1$ produces emission at the second wavelength $\lambda_2$.

10. The system of claim 9, wherein the alloy comprises at least one of:
   a zinc sulfide and zinc selenide alloy; or
   a zinc sulfide and cadmium sulfide alloy.

11. The system of claim 10, wherein the alloy comprises at least one of:
   said zinc sulfide and zinc selenide alloy having a zinc sulfide concentration from 65 to 75%; or
   said zinc sulfide and cadmium sulfide alloy having a zinc sulfide concentration from 65 to 75%.

12. The system of claim 10, wherein the alloy has said emission of the second wavelength $\lambda_2$ at 365 nm.

13. The system of claim 1, wherein the up-converter particle comprises at least one of:
   a dielectric or semiconductor configured to generated said wavelength $\lambda_2$; or
   multiple dielectrics or semiconductors respectively configured to emit at different wavelengths for $\lambda_2$.

14. The system of claim 1, wherein the metallic structure comprises at least one of:
   a metallic shell comprises at least one of a spherical shell, an oblate shell, a crescent shell, or a multilayer shell.

15. The system of claim 1, wherein said metallic structure comprises at least one of Au, Ag, Cu, Ni, Pt, Pd, Co, Ru, Rh, Al, Ga, or a combination or alloys or layers thereof.

16. The system of claim 1, wherein the up-converter particle comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

17. The system of claim 16, wherein the up-converter particle comprises a dopant including at least one of Er, Eu, Yb, Tm, Nd, Tb, Ce, Y, U, Pr, La, Gd and other rare-earth species or a combination thereof.

18. The system of claim 17, wherein the dopant includes at a concentration of 0.01%-50% by mol concentration.

19. The system of claim 1, wherein the up-converter particle comprises a plurality of particles including at least one of a first group which exhibits a visible light emission upon interaction with the first wavelength $\lambda_1$ and a second group which exhibits said ultraviolet light emission upon interaction with the first wavelength $\lambda_1$.

20. The system of claim 19, where the first group comprises a diagnostic group for producing imaging light showing a position of the first group in said medium, and the second group comprises a reaction-stimulating group producing a photostimulated reaction in said medium.

21. The system of claim 1, further comprising a recipient of the ultraviolet emission which is linked to the up-converter particle by a chemical moiety.

22. The system of claim 1, further comprising
   a secondary agent disposed in the medium,
   wherein the secondary agent comprises a photoactivatable polymer and the second wavelength $\lambda_2$ crosslinks the polymer or interacts with a surface of the polymer to produce a hydrophilic surface.

23. The system of claim 1, further comprising
   a recipient disposed in the medium in proximity to the up-converter particle which, upon activation by ultraviolet light of the second wavelength $\lambda_2$, generates said photostimulated reaction to produce a physical or biological change in the medium.

24. The system of claim 23, wherein the up-converter particle comprises a dielectric material including elements having energy states for absorption of the first wavelength $\lambda_1$ and recombination states for emission of the second wavelength $\lambda_2$.

25. The system of claim 23, wherein the up-converter particle comprises at least one of:
a dielectric or semiconductor configured to generated said wavelength $\lambda_2$; or
multiple dielectrics or semiconductors respectively configured to emit at different wavelengths for $\lambda_2$.

26. The system of claim 25, wherein the metallic structure comprises at least one of a spherical or elliptical shell covering at least a part of said dielectric or semiconductor.

27. The system of claim 23, wherein said metallic structure comprises at least one of Au, Ag, Cu, Ni, Pt, Pd, Co, Ru, Rh, Al, Ga, or alloys or layers thereof.

28. The system of claim 23, wherein the up-converter particle comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

29. The system of claim 28, wherein the up-converter particle includes a dopant including at least one of Er, Eu, Yb, Tm, Nd, Tb, Ce, Y, U, Pr, La, Gd and other rare-earth species or a combination thereof.

30. The system of claim 29, wherein the dopant has a concentration of 0.01%-50% by mol concentration.

31. The system of claim 23, wherein the up-converter particle comprises a plurality of particles including at least one of a first group which exhibits a visible emission upon interaction with the first wavelength $\lambda_1$ and a second group which exhibits said ultraviolet light upon interaction with the first wavelength $\lambda_1$.

32. The system of claim 31, wherein:
the first group comprises a diagnostic group for producing imaging light showing a position of the first group in said medium; and
the second group comprises a reaction-stimulating group producing said photostimulated reaction in said medium.

33. The system of claim 23, further comprising an X-ray down-converter particle disposed in the medium, said X-ray down-converter particle includes at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er3^+$; ZnS:$Mn^{2+}$; ZnS:Mn, $Er^{3+}$, alkali lead silicate including compositions of $SiO_2$, $B_2O_3$, $Na_2O$, $K_2O$, PbO, MgO, or Ag, and combinations or alloys or layers thereof.

34. The system of claim 23, wherein the recipient is linked to the up-converter particle by a chemical moiety.

35. The system of claim 34, wherein a length of the chemical moiety increases a reactivity of the second wavelength $\lambda_2$ with the recipient.

36. The system of claim 23, where the recipient comprises a photoactivatable drug.

37. The system of claim 23, wherein the recipient comprises at least one of a laser dye, a fluorophore, a lumophore, or a phosphor.

38. The system of claim 23, further comprising a bioreceptor linked to the up-converter particle and including at least one of antibody probes, DNA probes, and enzyme probes, and combinations thereof.

39. The system of claim 23, further comprising a secondary agent linked to the up-converter particle and including at least one of secondary emitters, cytotoxic agents, magnetic resonance imaging (MRI) agents, positron emission tomography (PET) agents, radiological imaging agents, or photodynamic therapy (PDT) agents.

40. The system of claim 23, further comprising:
an X-ray source for irradiating the medium to irradiate an X-ray down-converter particle included in the medium and having a down conversion capability to produce down converted light.

41. The system of claim 40, wherein the recipient comprises a pharmaceutical compound disposed in a malignant tumor.

42. The system of claim 41, further comprising an infrared source, wherein the infrared source transmits light through the living body into the malignant tumor.

43. The system of claim 42, further comprising:
a fiber optic inserted into the living body, wherein the infrared source transmits light through the fiber optic to the malignant tumor.

44. A system for energy upconversion inside a medium to induce a biological change in the medium, comprising:
an up-converter particle disposed in the medium and configured, upon exposure to a first wavelength $\lambda_1$ of radiation, to generate a second wavelength $\lambda_2$ of radiation having a higher energy than the first wavelength $\lambda_1$;
a photoactivatable drug in a vicinity of the up-converter particle,
wherein
the second wavelength $\lambda_2$ of radiation comprises ultraviolet light generated within the medium surrounding the up-converter particle, and
said ultraviolet light from the up-converter particle produces said biological change to an entity in the medium by activation of the photoactivatable drug with said ultraviolet light generated within the medium.

45. The system of claim 44, wherein the photoactivatable drug comprises at least one of a psoralen, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones, and porphycene, rubyrin, rosarin, hexaphyrin, sapphyrin, chlorophyl, chlorin, phthalocynine, porphyrazine, bacteriochlorophyl, pheophytin, texaphyrin macrocyclic-based component, or a metalated derivative thereof.

46. The system of claim 44, further comprising a recipient of the ultraviolet emission which comprises at least one of a laser dye, a fluorophore, a lumophore, or a phosphor.

47. The system of claim 46, wherein the laser dye comprises at least one of p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2,7-dichlorofluorescein, rhodamine 65, and rhodamin 19 perchlorate, rhodamine b, and derivatives thereof.

48. The system of claim 44, further comprising a bioreceptor linked to the up-converter particle and including at least one of antibody probes, DNA probes, and enzyme probes, and combinations thereof.

49. The system of claim 44, further comprising a secondary agent linked to the up-converter particle and including at least one of secondary emitters, cytotoxic agents, magnetic resonance imaging (MRI) agents, positron emission tomography (PET) agents, radiological imaging agents, or photodynamic therapy (PDT) agents.

50. The system of claim 44, further comprising:
an X-ray source for irradiating the medium to irradiate an X-ray down-converter particle included in the medium and having a down conversion capability to produce down converted light.

51. The system of claim 50, wherein:
said down converted light is ultraviolet light.

52. The system of claim 44, wherein the ultraviolet light is generated in proximity of a pharmaceutical compound disposed inside a living body and activated by the ultraviolet light.

53. The system of claim 52, wherein the pharmaceutical compound is disposed in or nearby a malignant tumor to treat the malignant tumor.

54. The system of claim 44, wherein said first wavelength $\lambda_1$ is in the range of 700-1100 nanometers.

55. The system of claim 44, wherein said first wavelength $\lambda_1$ is in the range of 1300-1550 nm.

56. The system of claim 44, further comprising at least one down converter particle including at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er3+$; ZnS:$Mn^{2+}$; ZnS:Mn, $Er^{3+}$, alkali lead silicate including compositions of $SiO_2$, $B_2O_3$, $Na_2O$, $K_2O$, PbO, MgO, or Ag, and combinations or alloys or layers thereof.

57. A system for energy upconversion inside a medium, comprising:
an up-converter particle disposed in the medium and configured, upon exposure to a first wavelength $\lambda_1$ of radiation, to generate a second wavelength $\lambda_2$ of radiation having a higher energy than the first wavelength $\lambda_1$; and
a metallic structure disposed in relation to the particle and inside the medium,
wherein
the second wavelength $\lambda_2$ of radiation comprises ultraviolet emission generated within the medium surrounding the particle and the metallic structure, and
said ultraviolet emission produces a biological change to an entity in the medium, wherein the second wavelength $\lambda_2$ sterilizes a pathogen inside the medium.

58. A readable article comprising:
a medium containing identification information;
an upconverter particle included in or on the surface of the medium; and
said up-converter particle configured, upon exposure to a first wavelength $\lambda_1$ of radiation, to emit a second wavelength $\lambda_2$ of radiation having a higher energy than the first wavelength $\lambda_1$,
wherein said second wavelength $\lambda_2$ is visible light, and
said visible light has an intensity permitting human observation of the identification information.

59. The article of claim 58, further comprising:
a metallic structure disposed in relation to the up-converter particle,
wherein a physical characteristic of the metallic structure is set to a value where a surface plasmon resonance in the metallic structure resonates at a frequency which provides spectral overlap with either the first wavelength $\lambda_1$ or the second wavelength $\lambda_2$.

60. The article of claim 58, wherein the up-converter particle comprises a plurality of particles including at least one of a first group which exhibits a visible emission upon interaction with the first wavelength $\lambda_1$ and a second group which exhibits infrared emission upon interaction with the first wavelength $\lambda_1$.

61. The article of claim 60, wherein the first group comprises a part of a visible tag on the object, and the second group comprises a part of an invisible tag on the object.

62. The article of claim 58, wherein the up-converter particle comprises a plurality of particles including at least one of a first group which exhibits a visible emission upon interaction with the first wavelength $\lambda_1$ and a second group which exhibits ultraviolet emission upon interaction with the first wavelength $\lambda_1$.

63. The article of claim 62, where the first group comprises a part of a visible tag on the object, and the second group comprises a part of an invisible tag on the object.

64. The article of claim 58, wherein the medium comprises at least one of a paper product, a plastic product, and a glass product.

65. The article of claim 58, where the medium comprises at least one of a security tag or a bar code.

66. A system for energy upconversion inside a medium, comprising:
an up-converter particle disposed in the medium and configured, upon exposure to a first wavelength $\lambda_1$ of radiation, to generate a second wavelength $\lambda_2$ of radiation having a higher energy than the first wavelength $\lambda_1$; and
wherein
the second wavelength $\lambda_2$ of radiation comprises ultraviolet emission generated within the medium surrounding the up-converter particle, and
said ultraviolet emission produces a change in biological activity of an entity in the medium.

67. The system of claim 66, wherein:
the up-converter particle comprises a dielectric particle; and
the dielectric particle comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

68. The system of claim 66, wherein the up-converter particle comprises an alloy of two or more dielectric materials, an alloy of two or more glasses, or an alloy of two or more semiconductors.

69. The system of claim 66, wherein the up-converter particle comprises a nanoparticle having a size less than 1000 nm.

70. The system of claim 66, wherein the up-converter particle comprises an alloy of two or more materials, wherein the alloy has a composition between the two or materials set to a compositional value where excitation of the alloy at the first wavelength $\lambda_1$ produces emission at the second wavelength $\lambda_2$.

71. The system of claim 70, wherein the alloy comprises at least one of:
a zinc sulfide and zinc selenide alloy; or
a zinc sulfide and cadmium sulfide alloy.

72. The system of claim 66, wherein the up-converter particle comprises at least one of:
a dielectric or semiconductor configured to generated said wavelength $\lambda_2$; or multiple dielectrics or semiconductors respectively configured to emit at different wavelengths for $\lambda_2$.

73. The system of claim 66, wherein the metallic structure comprises at least one of:
a metallic shell comprises at least one of a spherical shell, an oblate shell, a crescent shell, or a multilayer shell.

74. The system of claim 66, wherein the up-converter particle comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

75. The system of claim 74, wherein the up-converter particle comprises a dopant including at least one of Er, Eu, Yb, Tm, Nd, Tb, Ce, Y, U, Pr, La, Gd and other rare-earth species or a combination thereof.

76. The system of claim 44, wherein the photoactivatable drug is linked to the up-converter particle by a chemical moiety.

* * * * *